US011065295B1

(12) United States Patent
Pond

(10) Patent No.: US 11,065,295 B1
(45) Date of Patent: Jul. 20, 2021

(54) COMPOSITIONS AND METHODS FOR NUTRITIONAL SUPPLEMENTS

(71) Applicant: DailyColors Health Inc., Sebastopol, CA (US)

(72) Inventor: Hartley Pond, Sebastopol, CA (US)

(73) Assignee: DAILYCOLORS HEALTH INC., Sebastopol, CA (US)

( * ) Notice: Subject to any disclaimer, the term of this patent is extended or adjusted under 35 U.S.C. 154(b) by 0 days.

(21) Appl. No.: 17/167,998

(22) Filed: Feb. 4, 2021

Related U.S. Application Data

(60) Provisional application No. 63/086,207, filed on Oct. 1, 2020, provisional application No. 63/010,183, filed on Apr. 15, 2020, provisional application No. 62/970,615, filed on Feb. 5, 2020.

(51) Int. Cl.
| | |
|---|---|
| *A61K 36/00* | (2006.01) |
| *A61K 36/9068* | (2006.01) |
| *A23L 33/00* | (2016.01) |
| *A23L 33/105* | (2016.01) |
| *A61K 45/06* | (2006.01) |
| *A61K 36/752* | (2006.01) |
| *A61K 9/14* | (2006.01) |
| *A61K 36/45* | (2006.01) |
| *A61K 36/81* | (2006.01) |
| *A61K 36/21* | (2006.01) |
| *A61K 9/00* | (2006.01) |
| *A61K 36/23* | (2006.01) |

(52) U.S. Cl.
CPC ........ *A61K 36/9068* (2013.01); *A23L 33/105* (2016.08); *A23L 33/30* (2016.08); *A61K 9/0053* (2013.01); *A61K 9/14* (2013.01); *A61K 36/21* (2013.01); *A61K 36/23* (2013.01); *A61K 36/45* (2013.01); *A61K 36/752* (2013.01); *A61K 36/81* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2015/0190450 | A1* | 7/2015 | Chang | A23L 33/10 424/443 |
| 2018/0078649 | A1* | 3/2018 | Zu | A61K 31/704 |
| 2018/0318323 | A1 | 11/2018 | Roman et al. | |

FOREIGN PATENT DOCUMENTS

| | | |
|---|---|---|
| CN | 108541953 A | 9/2018 |
| KR | 1020090078939 A | 7/2009 |
| KR | 1020180020718 A | 2/2018 |
| WO | 2019092896 A1 | 5/2019 |

OTHER PUBLICATIONS

Ahmad et al., Assessment of Risk Factors and Biomarkers Associated With Risk of Cardiovascular Disease Among Women Consuming a Mediterranean Diet Dec. 7, 2018; 1(8); 14 pgs.
Allard et al., "The ectonucleotidases CD39 and CD73: novel checkpoint inhibitor targets," Immunol Rev., Mar. 2017; 276(1):121-144.
Anhe et al., "Triggering Akkermansia with dietary polyphenols: a new weapon to combat the metabolic syndrome?" Gut Microbes, 2016; 7(2):146-153.
Antonioli et al., "CD39 and CD73 in immunity and inflammation," Trends Mol Med., Jun. 2013; 19(6):355-367.
Biagi et al., "Gut Microbiota and Extreme Longevity," Current Biology, Jun. 6, 2016; 26:1480-1485.
Billingsley et al., "The antioxidant potential of Mediterranean diet in patients at high cardiovascular risk: an in-depth review of the PREDIMED," Nutrition and Diabetes, 2018; 8:13; 8 pgs.
Bose et al., "Targeting the JAK/STAT Signaling Pathway Using Phytocompounds for Cancer Prevention and Therapy," Cells, 2020; 9,1451; 40 pgs.
Caldwell et al., "Arginase: A Multifaceted Enzyme Important in Health and Disease," Physiol. Rev., 2018; 98:641-665.
Cham et al., "Immunotherapeutic Blockade of CD47 Inhibitory Signaling Enhances Innate and Adaptive Immune Responses to Viral Infection," Cell Reports, 2020; 31, 107494; 14 pgs.
Chini et al., "The NADase CD38 is induced by factors secreted from senescent cells providing a potential link between senescence and age-related cellular NAD+ decline," Biochem Biophys Res Commun., May 28, 2019; 513 (2):486-493.
Chini et al., "The Pharamacology of CD38/NADase: An emerging target for cancer and aging diseases," Trends Pharmacol Sci., Apr. 2018; 39(4):424-436.
Crooke et al., "Low expression of CD39 and CD73 genes in centenarians compared with octogenarians," Immunity & Ageing; 2017; 14:11; 5 pgs.
Fytexia, OXXYNEA Information Sheet, retrieved from the internet on Oct. 24, 2019, 4 pgs. www.fytexia.com—www.oxxynea.com.
Gomez-Pinilla et al., "Natural mood foods: The actions of polyphenols against psychiatric and cognitive disorders," May 2012; 15(3):127-133.
Goncalves et al., "Chapter 6: Phenolic Compounds—Biological Activity: Inhibitory Properties of Phenolic Compounds Against Enzymes Linked with Human Diseases," Intech Open Science, 2017, pp. 99-118.
Gonzalez de Mejia et al., "The Colors of Health: Chemistry, Bioactivity, and Market Demand for Colorful Foods and Natural Food Sources of Colorants," Annu. Rev. Food Sci. Technol., 2020; 15:47; 11:10.1-10.38.

(Continued)

*Primary Examiner* — Qiuwen Mi
(74) *Attorney, Agent, or Firm* — Umberg Zipser LLP

(57) ABSTRACT

Compositions and methods are presented in which a plurality of chemically distinct polyphenols inhibit multiple enzymes in pathways associated with health and healthy ageing. Preferred compositions are derived from colored plant materials that are commonly found in the Mediterranean diet and provide the biochemical basis for the health benefits of the Mediterranean diet. Notably, the enzyme inhibition observed with the combined polyphenols was synergistic with respect to not one but a significant number of enzymes in the pathways associated with health and healthy ageing, thus providing an amplified desirable effect.

14 Claims, 35 Drawing Sheets

(56) References Cited

OTHER PUBLICATIONS

Gu et al., "Mediterranean Diet, Inflammatory and Metabolic Biomarkers, and Risk of Alzheimer's Disease," J Alzheimers Dis., 2010; 22(2):483-492.
Hogan et al., "The Multi-faceted Ecto-enzyme CD38: Roles in Immunomodulation, Cancer, Aging, and Metabolic Diseases," Frontiers in Immunology, May 2019; 10, Art. 1187; 12 pgs.
Jobs, et al., "Association Between Serum Cathepsin S and Mortality in Older Adults," JAMA, Sep. 14, 2011; 306 (10):1113-1121.
Koelsch, Gerald, "BACE1 Function and Inhibition: Implications of Intervention in the Amyloid Pathway of Alzheimer's Disease Pathology," Molecules, 2017; 22, 1723; 20 pgs.
Lahoz et al., "Relationship of the Adherence to a Mediterranean Diet and Its Main Components with CRP Levels in the Spanish Population," Nutrients, 2018; 10, 379; 9 pgs.
Marttila et al., "Aging-associated increase in indoleamine 2,3-dioxygenase (IDO) activity appears to be unrelated to the transcription of the IDO1 or IDO2 genes in peripheral blood mononuclear cells," Immunity & Ageing, 2011; 8:9; 4 pgs.
Masi et al., "Aging Modulates the Influence of Arginase on Endothelial Dysfunction in Obesity," Arterioscler Thromb Vasc Biol., 2018; 38:2474-2483.
Mushtaq et al., "Neuroprotective Mechanisms Mediated by CDK5 Inhibition," Curr Pharm Des., 2016; 22(5):527-534.
Prendergast et al. "Discovery of IDO1 inhibitors: from bench to bedside," Cancer Res., Dec. 15, 2017; 77 (24):6795-6811.
Schwartz et al., "JAK inhibition as a therapeutic strategy for immune and inflammatory diseases," Nat Rev Drug Discov., Dec. 28, 2017; 17(1):78; 41 pgs.
Sreekumar, et al., "Pomegranate Fruit as a Rich Source of Biologically Active Compounds," BioMed Research International, 2014; 12 pgs.
Sureda et al., "Adherence to the Mediterranean Diet and Inflammatory Markers," Nutrients, Jan. 10, 2018; 10, 62; 13 pgs.
Xu et al., "Perspective: Targeting the JAK/STAT pathway to fight age-related dysfunction," Pharmacol Res., Sep. 2016; 111:152-154.
Zhao et al., "What Else Can CD39 Tell Us?" Frontiers in Immunology, Jun. 2017; vol. 8; 10 pgs.
Beecher, Gary R., "Overview of Dietary Flavonoids: Nomenclature, Occurrence and Intake," The Journal of Nutrition, Oct. 2003; 133(10):3248S-3254S.
Huang et al., "Curcumin inhibits BACE1 expression through the interaction between ERBeta and NFkB signaling pathway in SH-SY5Y cells," Molecular and Cellular Biochemistry, 2020; 463:161-173.
Lakey-Beitia et al., "Polyphenols as Therapeutic Molecules in Alzheimer's Disease, Through Modulating Amyloid Pathways" Mol. Neurobiol., 2015; 51:466-479.

\* cited by examiner

COMPOSITIONS AND METHODS FOR NUTRITIONAL SUPPLEMENTS

This application claims priority to our U.S. Provisional Patent Applications with the Ser. No. 62/970,615, filed Feb. 5, 2020, the Ser. No. 63/010,183, filed Apr. 15, 2020, and the Ser. No. 63/086,207, filed Oct. 1, 2020, each of which is incorporated by reference herein.

FIELD OF THE INVENTION

The field of the invention is compositions and methods for nutritional supplements, especially as it relates polyphenols and polyphenol mixtures commonly associated with a diet rich in fruits and vegetables and their use in conditions, disorders, and diseases associated with various enzymes inhibited by such polyphenol mixtures.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

There is a considerable variety of vitamins and other isolated nutritional compounds, and alleged benefits of such compounds include, among numerous other effects, immune support, anti-inflammatory effects, anti-ageing effects, cardiac support, and digestive support. Unfortunately, there is only a rather small body of evidence that substantiates some aspects of these alleged benefits when these vitamins and other isolated nutritional compounds are ingested. Similarly, where the nutritional supplement is an extract or powdered form of a plant part, various benefits are advertised, but actual benefits are often poorly or even not at all proven. Moreover, isolated nutritional compounds as well as individual plant extracts and concentrates are generally not reflective of a healthy diet.

Notably, there are certain geographic and ethnographic diet types that are associated with overall health, longevity, and/or physical resilience, and such beneficial effects are indeed well documented and substantiated. For example, the Mediterranean diet is typically associated with lower cardiovascular risk factors (see e.g., *Nutrients* 2018, 10, 379; doi:10.3390/nu10030379), lower inflammatory and metabolic biomarkers, a reduction in risk of Alzheimer's disease (see e.g., *J Alzheimers Dis.* 2010; 22(2): 483-492.), and with a reduction in certain inflammatory markers (see e.g., *Nutrients* 2018, 10, 62; doi:10.3390/nu10010062). One common ingredient class found in such diets are polyphenols, and various studies have been published regarding specific benefits of individual dietary polyphenols (see e.g., Inhibitory Properties of Phenolic Compounds Against Enzymes Linked with Human Diseases: URL:dx.doi.org/10.5772/66844), and selected colored polyphenols (see e.g., *Annu. Rev. Food Sci. Technol.* 2020. 11:10.1-10.38). However, due to the complexity and large number of chemically distinct polyphenols, many studies only focus on single polyphenols and particular biochemical effects of such compounds or provide general epidemiological information without more detailed molecular characterization of the diets.

In an effort to supplement a diet with multiple polyphenols, various supplements are known. For example, Vital Reds (by Gundry MD) provides a commercially available concentrated polyphenol powder blend from a number of red colored plant materials to increase energy and improve digestion. Such blend advantageously includes a variety of chemically distinct polyphenols. However, the selection of plant materials used as a source of polyphenols is not reflective of common dietary intake. Similarly, Oxxynea by Fytexia, a commercially available mixture of grape, olive, pomegranate, green tea, grapefruit, bilberry, and orange extracts is offered as an antioxidant formulation to protect cells from oxidative stress (see e.g., Oxxynea by Fytexia). While beneficial to reduce oxidative stress, the source ingredients for such antioxidant formulation are once more not reflective of a common dietary intake. Surprisingly, despite the numerous beneficial components found in various dietary supplements, there is no supplement that is expected to provide the various benefits of a Mediterranean diet, and particularly the benefits of colored polyphenolic components in Mediterranean diet.

Thus, even though various nutritional supplements are known in the art, all or almost all of them suffer from various disadvantages. Consequently, there is a need to provide improved compositions and methods for nutritional supplements, and especially beneficial/synergistic combinations of polyphenols known to be associated with healthy diets such as the Mediterranean diet.

SUMMARY OF THE INVENTION

The inventor has now discovered various compositions and methods for specific combinations of polyphenols and/or polyphenol-rich materials (e.g., extracts and powders) commonly found in food items of the Mediterranean diet that exhibited, when combined, numerous benefits associated with the benefits of the Mediterranean diet. Indeed, the compositions and methods disclosed herein had substantial, and in some cases significant synergistic effect on a variety of molecular biomarkers associated with the benefits of the Mediterranean diet such as markers for ageing, senescence, inflammation, immune function, NAD/energy metabolism, and the gut microbiome.

In one aspect of the inventive subject matter, the inventor contemplates a nutritional composition that comprises a nutritionally acceptable carrier in combination with a plurality of chemically distinct polyphenols from plant materials having a red color, a green color, an orange-yellow color, and a purple-blue color. Preferably, the chemically distinct polyphenols from the plant materials are present as a synergistic combination with respect to inhibition of at least one biochemical marker selected from the group consisting of BACE1, CD38, CD73, CDK5, JAK1, JAK2, and JAK3.

For example, in some embodiments the red colored plant materials comprise at least one (or two, or three, or all of) of an apple extract, a pomegranate extract, a tomato powder, and a beet root powder, wherein the green colored plant materials comprise at least one (or two, or three, or all of) of an olive extract, a rosemary extract, a green coffee bean extract, and a kale powder, wherein the orange-yellow colored plant materials comprise at least one (or two, or three, or all of) of an onion extract, a ginger extract, a grapefruit extract, and a carrot powder, and wherein the purple-blue colored plant materials comprise at least one (or two, or three, or all of) of a grape extract, a blueberry extract, a currant powder, and an elderberry powder.

In further aspect of the inventive subject matter, the chemically distinct polyphenols further inhibit at least one additional biochemical marker selected from the group consisting of ARG-1, ARG-2, SIRT-1, CD39, IDO1, IDO2, NAMPT, PCSK9, CD47, and Cathepsin S. Moreover, contemplated compositions may further inhibit Keap/Nrf2 binding and/or ACE2/Spike binding.

Most typically, but not necessarily, the composition is formulated in single dosage units for oral administration (e.g., each containing between 50 and 1,000 mg of the composition), which may be formulated as a capsule, a gummy, or a powder. Where desired, the composition may further comprise a vitamin, a dietary trace element or mineral, a nicotinamide riboside, a probiotic, and/or a prebiotic.

Therefore, in another aspect of the inventive subject matter, the inventor contemplates a nutritional composition that includes a nutritionally acceptable carrier in combination with a plurality of chemically distinct polyphenol-containing plant materials having a red color, a green color, an orange-yellow color, and a purple-blue color. Most preferably, the red colored plant materials comprise an apple extract, a pomegranate extract, a tomato powder, and a beet root powder; the green colored plant materials comprise an olive extract, a rosemary extract, a green coffee bean extract, and a kale powder; the orange-yellow colored plant materials comprise an onion extract, a ginger extract, a grapefruit extract, and a carrot powder; and the purple-blue colored plant materials comprise a grape extract, a blueberry extract, a currant powder, and an elderberry powder. For example, the apple extract, the pomegranate extract, the olive extract, the rosemary extract, the green coffee bean extract, the onion extract, the ginger extract, the grapefruit extract, the grape extract, and the blueberry extract may be ethanol extracts or ethanol/water extracts.

In such compositions the combination of plant materials is a synergistic combination with respect to inhibition of at least one biochemical marker selected from the group consisting of BACE1, CD38, CD73, CDK5, JAK1, JAK2, and JAK3, and especially with respect to inhibition of BACE1, CD38, and CD73. Preferred compositions further inhibit at least one additional biochemical marker selected from the group consisting of ARG-1, ARG-2, SIRT-1, CD39, IDO1, IDO2, NAMPT, PCSK9, CD47, and Cathepsin S, and may also inhibit Keap/Nrf2 binding and/or ACE2/Spike binding.

As before, it is preferred (but not needed) that the composition is formulated in single dosage units for oral administration. Typically, the dosage unit contains between 50 and 1,000 mg of the composition, and is formulated as a capsule, a gummy, or a powder. Where desired, contemplated compositions may further comprise a vitamin, a dietary trace element or mineral, a nicotinamide riboside, a probiotic, and/or a prebiotic.

Among other uses, contemplated compositions will be effective to treat and/or reduce a symptom of inflammatory condition, a cardiovascular condition, a neurological condition, a metabolic condition, and a cancer.

Therefore, the inventor also contemplates a method of supporting health of an individual that comprises a step of administering the compositions presented herein. For example, the composition may be administered to thereby provide immune support, metabolic support, support longevity, support central nervous system (CNS) function, reduce an inflammatory response, reduce effects of cardiovascular disease, and reduce the rate of amyloid beta plaque formation.

In further examples of such methods, the composition is orally administered over at least 30 days, typically at a daily dose of between 50 and 1,000 mg. As noted earlier, contemplated compositions may further comprise a step of co-administering a vitamin, a dietary trace element or mineral, a nicotinamide riboside, a probiotic, and/or a prebiotic (which may be performed in the same dosage unit or individually).

In another aspect of the inventive subject matter the inventor also contemplates a method of reducing an NAD+ decrease (e.g., age-related NAD+ decrease) in an individual that includes a step of administering to the individual a synergistic combination of polyphenols from plant materials having a red color, a green color, an orange-yellow color, and a purple-blue color wherein the combination synergistically inhibits CD38. In some embodiments, the polyphenols are provided in from of the plant materials.

Preferably, the red colored plant materials are selected from the group consisting of an apple extract, a pomegranate extract, a tomato powder, and a beet root powder, wherein the green colored plant materials are selected from the group consisting of an olive extract, a rosemary extract, a green coffee bean extract, and a kale powder, wherein the orange-yellow colored plant materials are selected from the group consisting of an onion extract, a ginger extract, a grapefruit extract, and a carrot powder, and wherein the purple-blue colored plant materials are selected from the group consisting of a grape extract, a blueberry extract, a currant powder, and an elderberry powder.

In a further aspect of the inventive subject matter the inventor contemplates a method of supporting longevity of an individual that includes a step of administering to the individual a synergistic combination of polyphenols from plant materials having a red color, a green color, an orange-yellow color, and a purple-blue color wherein the combination synergistically inhibits CD73. In some embodiments, the polyphenols are provided in from of the plant materials.

Preferably, the red colored plant materials are selected from the group consisting of an apple extract, a pomegranate extract, a tomato powder, and a beet root powder, wherein the green colored plant materials are selected from the group consisting of an olive extract, a rosemary extract, a green coffee bean extract, and a kale powder, wherein the orange-yellow colored plant materials are selected from the group consisting of an onion extract, a ginger extract, a grapefruit extract, and a carrot powder, and wherein the purple-blue colored plant materials are selected from the group consisting of a grape extract, a blueberry extract, a currant powder, and an elderberry powder.

In yet another aspect of the inventive subject matter the inventor contemplates a method of supporting cognitive function of an individual that includes a step of administering a synergistic combination of polyphenols from plant materials having a red color, a green color, an orange-yellow color, and a purple-blue color wherein the combination synergistically inhibits BACE1. In some embodiments, the polyphenols are provided in from of the plant materials, and administration increases immune function to thereby support longevity and/or reduces the rate of amyloid beta plaque formation.

Preferably, the red colored plant materials are selected from the group consisting of an apple extract, a pomegranate extract, a tomato powder, and a beet root powder, wherein the green colored plant materials are selected from the group consisting of an olive extract, a rosemary extract, a green coffee bean extract, and a kale powder, wherein the orange-yellow colored plant materials are selected from the group consisting of an onion extract, a ginger extract, a grapefruit extract, and a carrot powder, and wherein the purple-blue colored plant materials are selected from the group consisting of a grape extract, a blueberry extract, a currant powder, and an elderberry powder.

In still another aspect of the inventive subject matter the inventor contemplates a method of supporting central nervous system (CNS) function in an individual that includes a step of administering a synergistic combination of polyphenols from plant materials having a red color, a green color, an orange-yellow color, and a purple-blue color wherein the combination synergistically inhibits CDK5. In some embodiments, the polyphenols are provided in from of the plant materials, and administration reduces age-related cognitive decline.

Preferably, the red colored plant materials are selected from the group consisting of an apple extract, a pomegranate extract, a tomato powder, and a beet root powder, wherein the green colored plant materials are selected from the group consisting of an olive extract, a rosemary extract, a green coffee bean extract, and a kale powder, wherein the orange-yellow colored plant materials are selected from the group consisting of an onion extract, a ginger extract, a grapefruit extract, and a carrot powder, and wherein the purple-blue colored plant materials are selected from the group consisting of a grape extract, a blueberry extract, a currant powder, and an elderberry powder.

In a further aspect of the inventive subject matter the inventor contemplates a method of supporting immune function in an individual that includes a step of administering a synergistic combination of polyphenols from plant materials having a red color, a green color, an orange-yellow color, and a purple-blue color wherein the combination synergistically inhibits at least one of JAK1, JAK2, and JAK3. In some embodiments, the polyphenols are provided in from of the plant materials, and administration reduces a symptom of rheumatoid arthritis, psoriasis, or inflammatory bowel disease.

Preferably, the red colored plant materials are selected from the group consisting of an apple extract, a pomegranate extract, a tomato powder, and a beet root powder, wherein the green colored plant materials are selected from the group consisting of an olive extract, a rosemary extract, a green coffee bean extract, and a kale powder, wherein the orange-yellow colored plant materials are selected from the group consisting of an onion extract, a ginger extract, a grapefruit extract, and a carrot powder, and wherein the purple-blue colored plant materials are selected from the group consisting of a grape extract, a blueberry extract, a currant powder, and an elderberry powder.

Additionally, the inventor also contemplates a method of inhibiting at least one of BACE1, CD38, CD73, CDK5, JAK1, JAK2, and JAK3 that includes a step of contacting at least one of the BACE1, the CD38, the CD73, the CDK5, the JAK1, the JAK2, and the JAK3 with a plurality of chemically distinct polyphenols from plant materials having a red color, a green color, an orange-yellow color, and a purple-blue color, wherein the chemically distinct polyphenols from the plant materials are a synergistic combination with respect to inhibition of at least one biochemical marker selected from the group consisting of the BACE1, the CD38, the CD73, the CDK5, the JAK1, the JAK2, and the JAK3. In some embodiments, the polyphenols are provided in from of the plant materials.

For example, the red colored plant materials are selected from the group consisting of an apple extract, a pomegranate extract, a tomato powder, and a beet root powder, wherein the green colored plant materials are selected from the group consisting of an olive extract, a rosemary extract, a green coffee bean extract, and a kale powder, wherein the orange-yellow colored plant materials are selected from the group consisting of an onion extract, a ginger extract, a grapefruit extract, and a carrot powder, and wherein the purple-blue colored plant materials are selected from the group consisting of a grape extract, a blueberry extract, a currant powder, and an elderberry powder.

Advantageously, the step of contacting is performed in vivo (e.g., oral administration to a mammal), and administration of the plurality of chemically distinct polyphenols provides immune support, metabolic support, support longevity, supports central nervous system (CNS) function, reduces an inflammatory response, reduces effects of cardiovascular disease, and/or reduces the rate of amyloid beta plaque formation.

Viewed from a different perspective, the inventor also contemplates a method of treating a condition that is associated with activity of at least one of BACE1, CD38, CD73, CDK5, JAK1, JAK2, JAK3, ARG-1, ARG-2, SIRT-1, CD39, IDO1, IDO2, NAMPT, PCSK9, CD47, and Cathepsin S in a mammal. Such method will typically include a step of administering to the mammal a plurality of chemically distinct polyphenols in an amount effective to inhibit at least one of the BACE1, the CD38, the CD73, the CDK5, the JAK1, the JAK2, the JAK3, the ARG-1, the ARG-2, the SIRT-1, the CD39, the IDO1, the IDO2, the NAMPT, the PCSK9, the CD47, and the Cathepsin S. In preferred embodiments, the chemically distinct polyphenols synergistically inhibit BACE1, CD38, CD73, CDK5, JAK1, JAK2, and/or JAK3.

For example, the condition may be an inflammatory condition, a cardiovascular condition, a neurological condition, a metabolic condition, and/or a cancer. Where desired, the plurality of chemically distinct polyphenols are from plant materials having a red color, a green color, an orange-yellow color, and a purple-blue color. For example, the red colored plant materials are selected from the group consisting of an apple extract, a pomegranate extract, a tomato powder, and a beet root powder, wherein the green colored plant materials are selected from the group consisting of an olive extract, a rosemary extract, a green coffee bean extract, and a kale powder, wherein the orange-yellow colored plant materials are selected from the group consisting of an onion extract, a ginger extract, a grapefruit extract, and a carrot powder, and wherein the purple-blue colored plant materials are selected from the group consisting of a grape extract, a blueberry extract, a currant powder, and an elderberry powder. It should also be appreciated that the polyphenols may be provided in from of the plant materials.

Moreover, it is contemplated that the plurality of chemically distinct polyphenols may be orally administered to the mammal, typically at a daily dosage of between 50 and 1,000 mg. Where desired, such methods may further comprise a step of co-administering to the mammal a vitamin, a dietary trace element or mineral, a nicotinamide riboside, a probiotic, and/or a prebiotic.

In still further contemplated embodiments, the chemically distinct polyphenols are administered in an amount effective to inhibit at least three (or at least five or at least ten or all)

of the BACE1, the CD38, the CD73, the CDK5, the JAK1, the JAK2, the JAK3, the ARG-1, the ARG-2, the SIRT-1, the CD39, the IDO1, the IDO2, the NAMPT, the PCSK9, the CD47, and the Cathepsin S.

Therefore, and viewed from a different perspective, the inventor also contemplates the use of a plurality of chemically distinct polyphenols to support healthy ageing. Moreover, it is contemplated that the plurality of chemically distinct polyphenols in such use further inhibit SIRT-1, IDO1, IDO2, NAMPT, PCSK9, CD47, Keap/Nrf2 binding, and/or ACE2/Spike binding, and/or that the chemically distinct polyphenols synergistically inhibit the BACE1, the CD38, the CD73, the CDK5, the JAK1, the JAK2, and/or the JAK3.

As before, it is preferred that the red colored plant materials are selected from the group consisting of an apple extract, a pomegranate extract, a tomato powder, and a beet root powder, wherein the green colored plant materials are selected from the group consisting of an olive extract, a rosemary extract, a green coffee bean extract, and a kale powder, wherein the orange-yellow colored plant materials are selected from the group consisting of an onion extract, a ginger extract, a grapefruit extract, and a carrot powder, and wherein the purple-blue colored plant materials are selected from the group consisting of a grape extract, a blueberry extract, a currant powder, and an elderberry powder.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
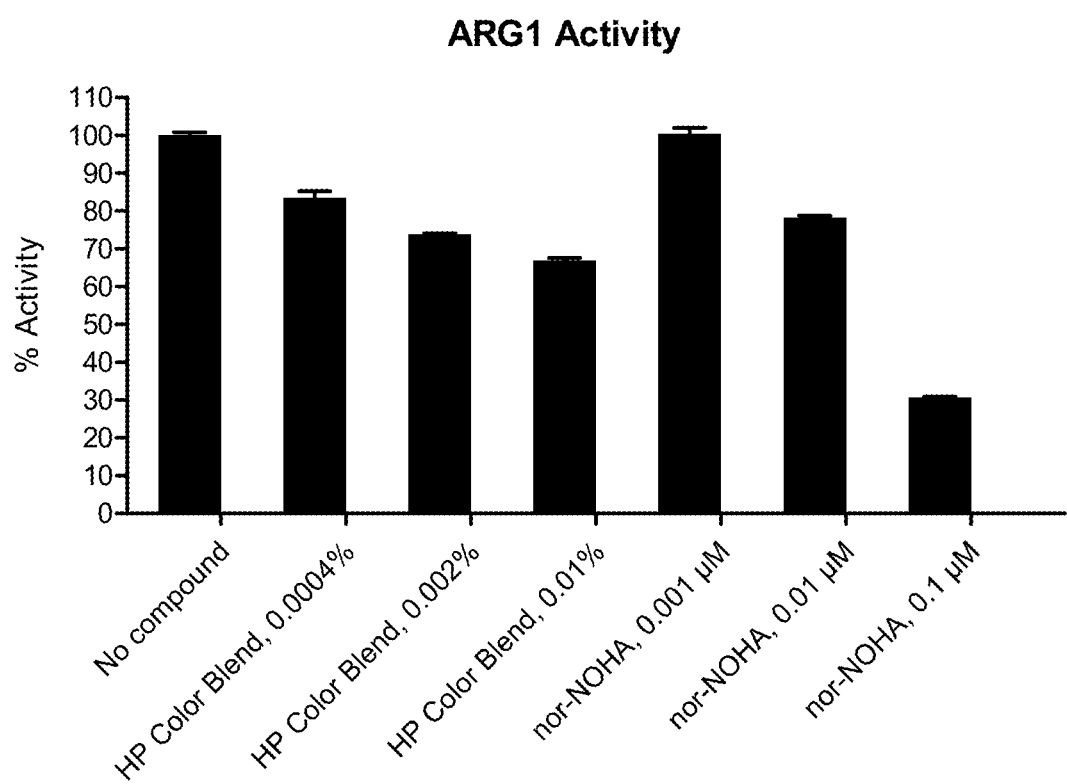
FIG. 1 is a graph depicting exemplary results for ARG-1 inhibition using a composition according to the inventive subject matter.

The inventor has discovered that specific combinations of polyphenol-containing materials (and polyphenols found therein) strongly modulated numerous biomarkers associated with the beneficial effects of the Mediterranean diet. In view of these findings, the inventor therefore contemplates various compositions for nutritional supplements and other nutritional products, compositions, and uses in medicinal food, and even use in medicine.

Most notably, the compositions presented herein had substantial and synergistic effects on a number of biomarkers associated with proper immune and CNS function, effective cellular metabolism, and longevity, and showed further significant effect on additional biomarkers associated with inflammatory responses, adverse effects of cardiovascular disease, and/or amyloid beta plaque formation. For example, the compositions and methods presented herein were demonstrated to have significant and beneficial effects on multiple enzymatic targets that are involved with numerous aspects of health and healthy ageing such as ARG-1, ARG-2, SIRT1, BACE1, Cathepsin S, CDK5, IDO1, IDO2, NAMPT, PCSK9, CD47, CD38, JAK1, JAK2, JAK3, CD39, and CD73, Keap/Nrf2. Viewed from a different perspective, it should be appreciated that the compositions presented herein are useful to beneficially affect multiple pathways associated with health and healthy ageing via inhibition of key signaling components and/or enzymes in these pathways. Remarkably, the observed modulation of these biomarkers using the compositions presented herein paralleled the profile of biomarkers in individuals that adhered to the Mediterranean diet and individuals with significant longevity.

For example, arginase 1 (ARG1) and arginase 2 (ARG2) are key enzymes in the urea cycle, cleaving L-arginine to form urea and L-ornithine. The urea cycle provides protection against excess ammonia, while L-ornithine is required for cell proliferation, collagen formation, and other important physiological functions. Notably, increases in arginase activity in mammals have been linked to dysfunction and pathologies of the cardiovascular system, kidney, and central nervous system, and also to dysfunction of the immune system and development of cancer. Two important aspects of the excessive activity of arginase may be involved in diseases. First, overly active arginase can reduce the supply of L-arginine needed for the production of nitric oxide (NO) by NO synthase. Second, excessive quantities of L-ornithine can lead to structural problems in the vasculature, neuronal toxicity, and abnormal growth of tumor cells (see e.g., *Physiol Rev* 98: 641-665, 2018). Furthermore, studies have demonstrated that increased formation of reactive oxygen species and key inflammatory mediators promote a pathological elevation of arginase activity. As such, inhibition of ARG1 and ARG2 is thought to beneficially counteract the adverse effects of arginase overactivity. As is shown on more detail below, contemplated compositions were effective in inhibiting ARG1 and ARG2 activity even at relatively low concentrations.

In another example, sirtuin1 (SIRT1) is a nuclear enzyme that deacetylates transcription factors that contribute to cellular regulation, and particularly to reaction to stressors. For example, SIRT1 deacetylates members of the PGC1-alpha/ERR-alpha complex, which are critical metabolic regulatory transcription factors, and deacetylates/deactivates the p53 protein, which is a key factor in many neoplastic diseases. SIRT1 was also demonstrated to play a role in activating T helper 17 cells, which contribute to autoimmune disease. As is shown in more detail below, contemplated compositions were effective in mildly inhibiting SIRT1 activity at relatively moderate concentrations.

In yet another example, beta-secretase 1 (BACE1) has been shown to be essential for the generation of β-amyloid in Alzheimer's disease and has also been reported to be associated with cognitive decline and decline in central nervous system (CNS) function (see e.g., *Molecules*. 2017 Oct. 13; 22(10):1723). Indeed, β-amyloid accumulation is a hallmark of ageing, and as such inhibitory compounds are thought to beneficially decelerate or even stop β-amyloid accumulation and as such preserve or maintain cognitive abilities and CNS function. As is described in more detail below, contemplated compositions have shown remarkable, strong, and even synergistic effect with regard to BACE 1 inhibition.

In yet another example, higher levels of Cathepsin S have been reported to be associated with higher risk of mortality and were in some studies also associated with higher risk of cardiovascular mortality (e.g., *JAMA*, Sep. 14, 2011-Vol 306, No. 10 1113). Other experimental studies have suggested that cathepsin S activity is involved in the development of cardiovascular disease via promotion of atherosclerotic plaques and destabilization of advanced plaques. Moreover, cathepsin S activity was also implicated in the development of cancer via stimulation of cancer cell migration and tumor angiogenesis, and higher levels of Cathepsin S activity was reported to be correlated with ageing of the brain. As such, reduced levels of Cathepsin S activity are believed to beneficially counteract these risks. Notably, contemplated compositions have shown remarkable and strong inhibitory effect with regard to BACE 1 inhibition.

Likewise, cyclin-dependent kinase 5 (CDK5) has been found to be essential to proper CNS function and its role in peripheral tissue and disease is growing. For example, acute CDK5 inhibition has a high potential therapeutic value to prevent neuronal injury in the events of stroke or brain injury, or during high-risk surgeries, such as neurovascular or cardiovascular surgeries, or potentially during prolonged, complicated labors. Pharmacological inhibition of CDK5 has been shown to protect neurons under a range of different stressful conditions and ageing (see e.g., *Curr Pharm Des*. 2016; 22(5): 527-534). Once more, contemplated compositions have shown remarkable, strong, and synergistic inhibitory effect with regard to CDK5 inhibition.

In still other example, Janus kinases 1, 2, and 3 (JAK1, JAK2, JAK3) are implicated in the regulation of cell cycle and cancer, presumably via NF-kB activation (see e.g., *Cells* 2020, 9, 1451). Moreover, small-molecule drugs that inhibit Janus kinases (JAK1-3) were essential signaling mediators downstream of many proinflammatory cytokines and have gained traction as safe and efficacious options for immune-mediated disorders. Not surprisingly, inhibition of JAKs has emerged as leading potential treatment of inflammation-driven pathologies like rheumatoid arthritis, psoriasis, and inflammatory bowel disease, as well as cardiovascular disease. Notably, contemplated compositions have shown remarkable, strong, and synergistic inhibitory effect with regard to JAK1, JAK2, and JAK3 inhibition (especially at high concentrations).

In still further examples, inhibition of indoleamine 2,3-dioxygenase-1 (IDO1) has emerged as a new treatment strategy for immune support, and particularly in the reversion of tumor-mediated immune suppression (see e.g., *Cancer Res.* 2017 December 15; 77(24): 6795-6811). Similarly, indoleamine 2,3-dioxygenase-2 (IDO2) has been implicated more recently in cancer, inflammation and immune control, and significant resources have been expended to identify IDO2 specific inhibitors. Increases in IDO1 and IDO2 activity have also been observed as a function of ageing (e.g., *Immunity & Ageing* 2011, 8:9), along with age related increase in inflammation, autoimmune disorders and malignancies. Remarkably, and as is shown in more detail below, contemplated compositions have shown strong inhibitory effect with regard to IDO1 and IDO2 inhibition.

With respect to energy metabolism, NAMPT and CD38 are known to modulate NAD+ in cells and as such are thought to be essential in maintaining and supporting of cellular energy and proper metabolic function. Indeed, over-activity of CD38 has been reported to increase with senescence (see e.g., *Biochem Biophys Res Commun.* 2019 May 28; 513(2): 486-493), cancer and ageing diseases (e.g., *Trends Pharmacol Sci.* 2018 April; 39(4): 424-436), immunomodulation and metabolic diseases (see e.g., FIMMU May 2019, Vol. 10, Article 1187). On that backdrop, inhibition of CD38 is believed to reduce or even prevent diseases associated with CD38 overactivity. On the other hand, nicotinamide phosphoribosyltransferase (NAMPT) mediates the rate-limiting step of the NAD salvage pathway that maintains cellular bioenergetics and provides a necessary substrate for functions essential to cells, and especially rapidly proliferating cancer cells. Once more, contemplated compositions have shown strong and synergistic inhibitory effect with regard to CD38 inhibition, and strong inhibition with repsect to NAMPT activity.

Moreover, overactivity of CD39 and CD73 have been reported to contribute to immune suppression, suppression of checkpoint inhibition in tumors, and other aspect of immune regulation (see e.g., FIMMU June 2017, Volume 8, Article 727; Immunol Rev. 2017 March; 276(1): 121-144). In addition, centenarians showed a significantly lower expression of CD39 and CD73 as compared to younger individuals (here: octogenarians), suggesting that the levels of CD39 as well as CD73 mRNA could be a hallmark of successful human ageing. Viewed from a different perspective, aging is associated with a decline in immune function and so contributes to the increased susceptibility to infectious diseases and higher incidence of malignant disease. Therefore, lower levels of CD39 activity are thought to be directly associated with healthy aging and longevity. Remarkably, contemplated compositions had a significant and synergistic effect in the inhibition of CD73 and a profound inhibitory effect on the activity of CD39 as is shown in more detail below. Likewise, CD47 inhibition was shown to lead to stimulation of phagocytosis of cancer cells and CD47 blockade not only enhanced the function of innate immune cells but also linked to adaptive immune responses (see e.g., *Cell Reports* 31, 107494 Apr. 14, 2020). Notably, contemplated compositions had a significant inhibitory effect in the inhibition of CD47 as is shown in further detail below.

In yet other examples, proprotein convertase subtilisin/kexin type 9 (PCSK9) has been reported as a contributor to plasma cholesterol levels, and inhibitors targeting PCSK9 have reduced plasma cholesterol in human. Once more, and as shown in more detail below, contemplated compositions had a significant and synergistic effect in the inhibition of PCSK9.

Additionally, the Keap1-Nrf2 pathway is a major regulator of cytoprotective responses to endogenous and exogenous stresses caused by reactive oxygen species (ROS) and Nrf2 activates expression of a variety of genes encoding stress response proteins. Inhibitors of Keap1-Nrf2 binding are therefore thought to increase expression of stress response related proteins. Remarkably, and as shown in more detail below, contemplated compositions had a significant and effect in the inhibition of Keap1-Nrf2 binding (and as such increase availability of Nrf2).

Finally, the inventor also discovered that contemplated compositions also had inhibitory effect in ACE2-Spike protein binding, which is implicated in viral propagation of corona viruses, and especially Sars-CoV2. As will be readily appreciated, contemplated compositions may therefore provide at least some protective effect against corona viruses, and especially Sars-CoV2.

Based on his extensive research, the inventor has now discovered that specific blends of selected plant materials common in the Mediterranean diet can be prepared that mimic the benefits of the Mediterranean diet as evidenced in the modulation of biomarkers. Preferably, such blends are combinations of colored plant materials that belong to a number (e.g., at least two, at least three, or at least four) of different color groups, and particularly plant materials having a red color, green color, orange/yellow color, and/or purple/blue color. For example, in one embodiment of contemplated compositions, polyphenol-containing products/extracts were obtained from red colored source materials that included an apple extract, a pomegranate extract, tomato powder, and beet root; from green colored source materials that included an olive extract, rosemary extract, green coffee bean extract, and kale; from orange/yellow colored source materials that included an onion extract, a ginger extract, a grapefruit extract, and carrot; and from purple/blue colored source materials that included a grape extract, a blueberry extract, currant, and elderberry, and the particular ingredients and proportions are described in more detail below. Viewed from a different perspective, contemplated compositions will therefore include a large number of polyphenols that below to at least two, or at least three, or at least four different polyphenolic classes, including organic acids, phenolics, flavonols, flavanols, anthocyanins, chlorogenic acids, betacyanins, etc. As will be readily appreciated, the particular choice of a plant material will depend on the desired (polyphenolic) component in the plant material and its effect on a particular biological system and/or signaling pathway.

Of course, it should also be appreciated that the plant materials may be provided in various forms, including whole plant materials or portions thereof (e.g., root, fruit, leaves, etc.) in fresh or dried form, juices or macerates from plant materials or portions thereof in fresh or dried form, and aqueous or aqueous/alcoholic extracts and chromatographic fractions of the aforementioned plant materials. Still further, it should be noted that one or more polyphenols of the plant materials may even be provided as purified (natural isolated or synthetic) chemical entities, typically with a chemical purity of at least 90%, or at least 95%, or at least 98%, or at least 99%. However, it should be recognized that in most embodiments the plant materials will be complex mixtures to provide a combination of desired biological effects on a number of distinct molecular entities (e.g., enzymes, receptors, ion channels) where at least some of the biological effects (e.g., at least one, or at least two, or at least three, etc.) are synergistic. Moreover, it is contemplated that the biological effects on the particular molecular entities will also be complementary in biological function. Therefore, and based on the testing and desired targets as described in more detail below, it should be appreciated that the compositions of the inventive subject matter may be formulated to meet a particular need. However, in especially preferred aspects contemplated compositions will inhibit multiple targets (e.g., at least two, at least three, at least four, etc.) in multiple and distinct (e.g., at least two, at least three, at least four, etc.) signaling pathways.

Consequently, and viewed from a different perspective, it should be appreciated that the mechanism of action of contemplated compositions is not limited to a single specific function (e.g., antioxidant) or limited to a specific chemical category (e.g., vitamins), but in fact complementarily and synergistically provides multiple biological activities across distinct metabolic and signaling pathways. As such, contemplated compositions and methods target a variety of biological systems, including energy metabolism, immune function, neural and CNS function, cardiac function, inflammation, etc. Notably, and as is described in more detail below, the compositions contemplated herein also affected a number of biomarkers associated with longevity (e.g., in blue zone populations such as Mediterranean population, Okinawan population, etc.) In addition, it is contemplated that the plant materials will also provide a variety of micro-nutrients to assist or complement the functions of the polyphenols and other colored pigments present in the compositions.

Consequently, it should be appreciated that the compositions contemplated herein may be advantageously used as a stand-alone product to support various aspects of health and healthy ageing such as support of proper immune function, support to reduce inflammation, support of normal NAD+ levels, support of cardiac health. In this context, it should be noted that the term "support" when used in conjunction with a physiological function or condition is intended to mean prevent decline of one or more components or activities of the component(s) associated with the physiological function or condition, at least partially reverse decline of one or more components or activities of the component(s) associated with the physiological function or condition, maintain normal function of one or more components or activities of the component(s) associated with the physiological function or condition, prevent abnormal overactivity (or over-expression) of one or more components associated with the physiological function or condition, and/or at least partially reverse abnormal overactivity (or over-expression) of one or more components associated with the physiological function or condition. Alternatively, the compositions contemplated herein may also be combined with other nutritional supplements and/or vitamins to provide beneficial effects otherwise not obtainable with such supplements or vitamins. In this context, it should be appreciated that most, if not all of the biomarkers tested herein were not substantially modulated by multivitamin compositions as is shown in more detail below. Thus, it should be recognized that the compositions resented herein present a new and different class of health support with a variety of beneficial effects that reach beyond the benefits of a multivitamin formulation.

In further contemplated aspects of the inventive subject matter it should be appreciated that the compositions presented herein may be formulated in a variety of forms, and particularly preferred formulations include those in combination with a nutritionally or pharmaceutically acceptable carrier, most preferably for oral administration (however, parenteral administration is also expressly contemplated). Therefore, contemplated compositions can be formulated as solid or a liquid product. For example, where contemplated compositions are formulated as a solid product, suitable product forms include single dosage unit formulations such as capsules, tablets, and powders, while other solid formulations include snack bars, gummies, or other edible products onto which the composition is coated (e.g., onto cereal) or into which the composition is mixed or layered (e.g., into chewing gum). In another examples, where contemplated compositions are formulated as a liquid product, suitable product forms include flavored and/or carbonated beverages (e.g., tea, juice), functional beverages (e.g., sports or energy drinks) or infusions, or liquid dairy product (e.g., yoghourt, kefir).

Therefore, contemplated compositions may be provided in bulk, as part of an edible or drinkable product, and/or provided in single dosage units for consumption. Most typically, the daily dosage for contemplated compositions (excluding the carrier) is preferably at least 10 mg, or at least 100 mg, or at least 200 mg, or at least 300 mg, or at least 400 mg, or at least 500 mg, or at least 750 mg, or at least 1,000 mg, or at least 1,500 mg. For example, suitable dosages will be between 10-100 mg, or between 100-200 mg, or between 200-400 mg, or between 300-600 mg, or between 400-800 mg, or between 600-1,000 mg, or between 1,000-2,000 mg.

As will be readily appreciated, contemplated compositions may further be combined with one or more additional ingredients to impart further desirable functionalities, and suitable additional ingredients include vitamins (e.g., single vitamins, or vitamin blends such as multivitamin blends), dietary trace elements or minerals (e.g., individual elements or minerals, or mixtures of multiple elements or minerals in various forms), various specialty compounds and mixtures (e.g., compositions comprising nicotinamide riboside, prebiotics, human milk oligosaccharides), and/or one or more probiotic microorganisms (e.g., *Lactobacillus* spec., *Bifidobacterium* spec., *Leukonostoc* spec., *Saccharomyces boulardii*, etc.).

Of course, it should be recognized that the compositions according to the inventive subject matter may be administered not only to a human, but also to other non-human mammals, and especially livestock and companion animals (e.g., dogs, cats, horses). Administration will typically be between once daily and three times daily (and in some cases even more) over a period of at least two days, three days, five days, 1 week, 2-4 weeks, 1-3 months, and even longer. Most typically, administration can be performed for a period sufficient to provide at least symptomatic relief of a condition (e.g., pain and swelling associated with inflammation, low energy level, frequent infections, etc.), or prophylactically to avoid or help reduce severity of a health condition.

Examples

Representative Composition:

Unless indicated otherwise, all tests were performed with a defined mixture of selected polyphenol-containing products/extracts common to the Mediterranean diet. The polyphenol-containing products/extracts were obtained from source materials characterized by color as follows: Red group: apple extract, pomegranate extract, tomato powder, and beet root; Green group: olive extract, rosemary extract, green coffee bean extract, and kale; Orange/yellow group: onion extract, ginger extract, grapefruit extract, and carrot; and Purple/blue group: grape extract, blueberry extract, currant, and elderberry. Corn starch, silica, and sunflower lecithin were used as processing aids. Relative proportions are shown in Table 1 below.

TABLE I

| Ingredient | Wt % | Part | Solvent | Standardized to | State |
|---|---|---|---|---|---|
| Grape Extract | 15.75 | Whole fruit | Ethanol | Min 50% total Proanthocyanidins | Powdered |
| Apple Extract | 10.00 | Whole fruit | Ethanol/Water | 70% Polyphenols | Powdered |
| Ginger Extract | 10.00 | Root | Ethanol/Water | 5% Gingerol | Powdered |
| Onion Extract | 10.00 | Root bulb | Ethanol/Water | 30% Quercetin | Powdered |
| Pomegranate Extract | 10.00 | Whole fruit | Ethanol | 40% Punicalagins | Powdered |
| Green Coffee Bean Extract | 7.50 | Seed | Ethanol/Water | 50% Chlorogenic Acids | Powdered |
| Rosemary Extract | 7.50 | Leaves | Ethanol/Water | 15% Rosmarinic Acid | Powdered |
| Olive Extract | 6.38 | Whole fruit | Water | 12% Hydroxytyrosol | Powdered |
| Maltodextrin | 3.19 | —/— | —/— | —/— | Powdered |
| Blueberry Extract | 2.50 | Whole fruit | Ethanol/Water | 12% Anthocyanins | Powdered |
| Grapefruit Extract | 2.50 | Whole fruit | Ethanol/Water | 90% Naringin | Powdered |
| Kale | 2.50 | Leaves | None | —/— | Powdered |
| Beet Root | 2.45 | Root | None | —/— | Powdered |
| Carrot | 2.45 | Root | None | —/— | Powdered |
| Black Currant | 2.43 | Whole fruit | None | —/— | Powdered |
| Elderberry | 2.43 | Whole fruit | None | —/— | Powdered |
| Tomato | 1.85 | Whole fruit | None | —/— | Powdered |
| Corn Starch | 0.31 | —/— | —/— | —/— | Powdered |
| Silica | 0.25 | —/— | —/— | —/— | Powdered |
| Sunflower Lecithin | 0.03 | —/— | —/— | —/— | Powdered |

Phytochemical HPLC/MS/MS analysis: An HPLC/MS compositional analysis of the exemplary composition above revealed the following ingredients and proportions where the columns in each of Tables 2-8 indicate the analyte ID (col. 1), chemical entity (col. 2), M-H (col. 3), RT (col. 4), peak intensity (col.5), and MS/MS fragments (col. 6):

TABLE 2

| | Organic acids | | | | |
|---|---|---|---|---|---|
| 1 | Citric acid | 191.0186 | 2.9 | 5.25E+08 | 102, 111, 129, 173 |
| 2 | Malic acid | 133.0130 | 2.2 | 1.26E+08 | 71, 89, 115 |

TABLE 2-continued

| | Organic acids | | | | |
|---|---|---|---|---|---|
| 3 | Glucaric acid | 209.0291 | 1.7 | 8.68E+08 | 133, 147, 191 |
| 4 | Gluconic acid | 195.0504 | 1.7 | 4.44E+08 | 99, 129, 159, 177 |
| 5 | hydroxy jasmonic acid-O-glucoside | 387.1668 | 22.3 | 2.23E+08 | 59, 163, 207 |
| 6 | Azelaic acid | 187.0968 | 28.3 | 1.56E+07 | 125, 169 |
| 5 | Arabinonic acid | 165.0395 | 1.7 | 1.96E+08 | 129, 147, 165 |

TABLE 3

| | Phenolics | | | | |
|---|---|---|---|---|---|
| 7 | Coumaric acid | 163.0389 | 24.3 | 9.19E+06 | 119, 147 |
| 8 | Coumaric aicd-derv | 295.0460 | 21.1 | 2.45E+06 | 119, 163 |
| 9 | Quinic acid-I | 191.0553 | 1.8 | 4.76E+08 | 173 |
| 10 | Quinic acid-II | 191.0553 | 20.1 | 2.40E+08 | 173 |
| 11 | Caffeic acid | 179.0341 | 21.4 | 1.54E+08 | 135 |
| 12 | Caffeic acid-hexose-I | 341.0869 | 16.6 | 5.02E+06 | 135, 161, 179 |
| 13 | Caffeic acid-hexose-II | 341.0869 | 18.5 | 1.28E+07 | 135, 161, 179 |
| 14 | Caffeic acid-hexose-III | 341.0869 | 19.6 | 1.02E+07 | 135, 179 |
| 15 | Caffeic acid-hexose-IV | 341.0869 | 20.0 | 1.61E+07 | 135, 161, 179 |
| 16 | Ferulic acid | 193.0498 | 25.6 | 4.32E+06 | 134.04, 149.06, 178.03 |
| 17 | Ferulic acid-hexose-I | 355.1028 | 21.7 | 1.97E+07 | 175 |
| 18 | Ferulic acid-hexose-I | 355.1028 | 22.5 | 5.63E+06 | |
| 19 | Ferulic acid-hexose-I | 355.1028 | 23.3 | 6.47E+06 | 134, 149, 175 |
| 20 | Ferulic acid-hexose-1 | 355.1028 | 24.9 | 3.24E+06 | 193 |
| 21 | Ferulic acid-hexose-I | 355.1028 | 25.9 | 4.32E+06 | 193 |
| 22 | 3,4-Dihydroxybenzoic acid | 153.0188 | 10.2 | 1.23E+07 | 109 |
| 23 | Gallic acid | 169.0132 | 5.3 | 6.41E+07 | 125 |
| 24 | Rosamric acid | 359.0772 | 28.8 | 1.18E+09 | 135, 131, 179, 197 |
| 25 | Rosamric acid dimer | 719.1618 | 28.8 | 5.48E+08 | 135, 161, 179, 197 |
| 26 | Salvianic acid A | 197.0447 | 9.2 | 7.12E+07 | 123, 135, 179, 180 |
| 27 | Ethyl gallate | 197.0449 | 24.3 | 1.83E+07 | 125, 151, 169 |
| 28 | Ellagic acid | 300.9994 | 25.8 | 1.20E+08 | 229, 257, 283 |
| 29 | Ellagic acid glucoside | 463.0529 | 22.9 | 5.69E+05 | 125, 169, 300.99, 463 |
| 30 | Galloyl-HHDP-glucoside | 633.0737 | 22.7 | 6.10E+07 | 125, 169, 193, 275, 300.99 |
| 31 | Digalloyl-HHDP-glucoside | 785.0867 | 22.3 | 1.92E+06 | 125, 169, 275, 300.99 |
| 32 | 3-Galloylquinic acid (Theogallin) | 343.0673 | 5.9 | 1.70E+06 | 169, 191 |

TABLE 3-continued

| | Phenolics | | | | |
|---|---|---|---|---|---|
| 33 | 3,4-Dihydroxybenzoic | 153.0183 | 10.2 | 1.23E+07 | 96, 109 |
| 34 | 3,4-Dihydroxybenzoic | 153.0545 | 10.3 | 3.62E+08 | 109, 123, 153.0182 |
| 35 | 2,4-Dihydroxybenzoic | 153.0183 | 23.8 | 8.71E+06 | 109 |
| 36 | 2-Hydroxybenzoic acid | 137.0232 | 15.0 | 1.10E+07 | 93 |

TABLE 4

| | Flavonoids | | | | |
|---|---|---|---|---|---|
| 37 | Naringenin | 271.0604 | 34.4 | 2.96E+07 | 119, 151, 227, 271 |
| 38 | Naringenin-glucoside | 433.1149 | 28.0 | 4.14E+06 | 151, 271 |
| 39 | Naringenin-rhamnoglucoside | 579.1722 | 27.5 | 1.13E+09 | 151, 271, 549 |
| 40 | Naringenin-rhamnoglucoside dimer | 1159.3540 | 27.5 | 5.66E+07 | 151, 271, 459 |
| 41 | Myricetin | 317.0503 | 29.0 | 1.09E+07 | 137, 151, 178 |
| 42 | Myricetin 3-rhamnoside | 463.0894 | 25.8 | 5.61E+06 | 316, 317 |
| 43 | Myricetin 3-glucoside I | 479.0839 | 24.3 | 4.59E+06 | 316, 317 |
| 44 | Myricetin 3-rhamnoside II | 479.0839 | 24.5 | 4.57E+06 | 316, 317 |
| 45 | Phloretin | 273.0769 | 34.5 | 2.41E+08 | 167 |
| 46 | Phloretin -glucoside | 435.1298 | 29.0 | 2.85E+08 | 167, 273 |
| 47 | Phloretin-arabinose-glucoside | 567.1733 | 27.5 | 3.28E+08 | 167, 273 |
| 48 | Phloretin-diglucoside | 597.1831 | 26.8 | 7.70E+06 | 167, 273 |
| 49 | Apigenin | 269.0460 | 34.4 | 4.46E+07 | 151 |
| 50 | Apigenin glucoside | 431.0985 | 27.8 | 1.36E+07 | 268, 269 |
| 51 | Apigenin rhamnoside glucoside | 577.1575 | 27.4 | 8.96E+07 | 269 |
| 52 | Apigenin rhamnoside glucoside der | 623.1635 | 27.4 | 7.88E+06 | 269, 577 |
| 53 | Apigenin rhamnoside glucoside dimer | 1155.3230 | 27.4 | 1.41E+06 | 269, 577 |
| 54 | Quercetin | 301.0348 | 32.1 | 1.89E+09 | 151, 179, 273, 301 |
| 55 | Quercetin dimer | 603.0795 | 32.1 | 3.94E+08 | 151, 178, 301 |
| 56 | Quercetin galactoside | 463.0874 | 24.6 | 1.00E+07 | 301 |
| 57 | Quercetin glucoside-1 | 463.0874 | 25.9 | 2.98E+07 | 151, 300, 301 |
| 58 | Quercetin glucoside-2 | 463.0874 | 26.1 | 7.16E+07 | 151, 300, 301 |
| 59 | Quercetin-diglucoside | 625.1400 | 23.8 | 8.83E+05 | 151, 178, 301, 463 |
| 60 | Quercetin-rutinoside or Rutin | 609.1478 | 25.5 | 3.37E+07 | 300, 301 |
| 61 | Luteolin | 285.0407 | 31.9 | 4.20E+07 | 133.03, 199.04, 217.05, 241 |
| 62 | Luteolin glucoside 1 | 447.0938 | 26.2 | 4.58E+06 | 284, 285 |
| 63 | Luteolin glucoside 2 | 447.0938 | 24.6 | 1.50E+07 | 284, 285 |
| 64 | Catechin-1 | 289.0704 | 20.2 | 5.97E+08 | 151, 179, 205, 245 |
| 65 | Catechin-2 | 289.0704 | 22.7 | 8.47E+08 | |
| 66 | Proanthocyanidin B1 | 577.1364 | 22.0 | 4.06E+08 | 125, 289, 407 |
| 67 | Proanthocyanidin B2 | 577.1364 | 18.9 | 2.14E+08 | 125, 289, 407 |
| 68 | Isorhamnetin | 315.0503 | 35.4 | 2.66E+08 | 300, 315 |
| 69 | Isorhamnetin glucoside | 477.1030 | 26.7 | 1.11E+08 | 119, 151, 299, 314, 315 |
| 70 | Isorhamnetin diglucoside-1 | 639.1563 | 27.4 | 1.11E+06 | 151, 285, 313, 315, 476, 477, 639 |
| 71 | Isorhamnetin-rhamnosyl-glucoside | 623.1939 | 26.1 | 6.63E+06 | 315 |
| 72 | Kaempferol | 285.0397 | 35.0 | 1.27E+08 | 125.02, 244, 257, 268 |
| 73 | Kaempferol glucoside-1 | 447.0938 | 26.9 | 4.02E+06 | |
| 74 | Kaempferol glucoside-2 | 447.0938 | 27.4 | 1.98E+07 | |
| 75 | Kaempferol glucoside-3 | 447.0938 | 27.6 | 1.04E+07 | |
| 76 | Kaempferol glucoside-4 | 447.0938 | 27.9 | 4.47E+06 | |
| 77 | Kaempferol-3-O-rutinoside | 593.1521 | 25.6 | 1.68E+07 | 285 |
| 78 | Kampferol 3-(6-glucosylglucoside) 7-rhamnoside | 755.2060 | 25.9 | 1.23E+06 | 285 |
| 79 | wogonin | 283.0616 | 41.2 | 1.42E+08 | 268,2 83 |

TABLE 5

| | Anthocyanin | | | | |
|---|---|---|---|---|---|
| 80 | Cyanidin-3-O-glucoside | 449.1073 | 21.1 | 1.67E+07 | 287 |
| 81 | Cyanidin derv | 463.0874 | 27.7 | 3.56E+05 | 287 |
| 82 | Cyanidin derv | 463.0874 | 29.1 | 1.97E+07 | 287 |
| 83 | Cyanidin-3-O-rutinoside | 595.1658 | 25.6 | 8.57E+05 | 287, 449 |
| 84 | Cyanidin 3-sambubioside | 581.1500 | 21.1 | 5.95E+06 | 287 |
| 85 | Pelargonidin | 271.0600 | 24.5 | 2.10E+06 | 271 |
| 86 | Pelargonidin-glucoside | 433.1131 | 27.9 | 7.85E+05 | 271 |
| 87 | Pelargonidin-glucoside derv | 639.1710 | 31.4 | 5.30E+05 | 175, 207, 271 |
| 88 | Malvidin | 331.0809 | 26.7 | 2.27E+06 | 316 |
| 89 | Malvidin arabinoside | 463.1237 | 23.0 | 8.98E+06 | 331 |
| 90 | Malvidin-feruloyl-arabinoside | 639.1710 | 28.1 | 7.34E+05 | 331 |
| 91 | Delphinidin | 303.0496 | 32.2 | 2.73E+07 | 303 |

TABLE 5-continued

| | Anthocyanin | | | |
|---|---|---|---|---|
| 92 | Delphinidin 3-glucoside | 465.1028 | 20.1 | 6.49E+06 303, 385 |
| 93 | Delphinidin 3-rutinoside | 611.1603 | 25.5 | 1.30E+06 303 |
| 94 | Delphinidin-3-arabinoside-1 | 435.0922 | 20.7 | 2.06E+06 303 |
| 95 | Petunidin | 317.0655 | 35.5 | 2.77E+06 317 |
| 96 | Petunidin 3-glucoside | 479.1186 | 26.7 | 1.32E+07 317 |
| 97 | Petunidin 3-rutinoside | 625.1765 | 26.1 | 5.63E+05 317 |
| 98 | Petunidin derv | 463.0874 | 26.9 | 4.03E+05 317 |
| 99 | Peonidin | 301.0709 | 34.8 | 1.63E+06 286 |
| 100 | Peonidin-glucoside-I | 463.1240 | 26.9 | 2.77E+06 301 |
| 101 | Peonidin-glucoside II | 463.1240 | 28.3 | 6.98E+06 301 |
| 102 | Peonidin-rutinoside | 609.1814 | 27.6 | 1.52E+06 301 |
| 103 | Peonidin-feruloyl-glucoside | 639.1710 | 31.7 | 1.88E+06 177, 301 |

TABLE 6

| | Chlorogenic acids | | | |
|---|---|---|---|---|
| 104 | 3-Caffeoylquinic acid | 353.0875 | 14.3 | 2.70E+08 135, 179, 191 |
| 105 | 5-Caffeoylquinic acid | 353.0875 | 20.1 | 8.52E+08 179, 191 |
| 106 | 4-Caffeoylquinic acid | 353.0875 | 21.1 | 5.09E+08 135, 173, 179, 191 |
| 107 | 3-Caffeoylquinic acid dimer | 707.1830 | 14.3 | 1.87E+07 135, 179, 191, 353 |
| 108 | 5-Caffeoylquinic acid dimer | 707.1833 | 20.1 | 9.23E+08 191, 353 |
| 109 | 4-Caffeoylquinic acid dimer | 707.1834 | 21.1 | 1.95E+08 135, 173, 179, 191, 353 |
| 110 | 3-Caffeoylshikimic acid | 335.0770 | 24.2 | 3.17E+07 135, 161, 173, 179 |
| 111 | 4-Caffeoylshikimic acid | 335.0770 | 24.5 | 1.62E+08 135, 161 |
| 112 | 5-Caffeoylshikimic acid | 335.0770 | 25.0 | 1.53E+08 161 |
| 113 | 3,4-Dicaffeoylshikimic acid | 497.1091 | 29.5 | 0 |
| 114 | 3,5-Dicaffeoylshikimic acid | 497.1091 | 32.0 | 9.10E+07 161, 179 335 |
| 115 | 4,5-Dicaffeoylshikimic acid | 497.1091 | 32.7 | 6.97E+06 135, 161, 179, 335 |
| 116 | 3-Feruloylquinic acid | 367.1032 | 20.7 | 1.13E+08 134, 193 |
| 117 | 5-Feruloylquinic acid | 367.1032 | 23.6 | 3.76E+08 163, 191 |
| 118 | 4-Feruloylquinic acid | 367.1035 | 23.8 | 1.66E+08 173, 193 |
| 119 | 3-Feruloylquinic acid dimer | 735.2144 | 20.7 | 7.14E+05 |
| 120 | 5-Feruloylquinic acid dimer | 735.2144 | 23.6 | 1.03E+08 173, 191, 367 |
| 121 | 4-Feruloylquinic acid dimer | 735.2144 | 23.8 | 4.17E+06 173, 193, 367 |
| 122 | 3-Coumaroylquinic acid | 337.0932 | 19.0 | 2.68E+07 119, 163 |
| 123 | 4-Coumaroylquinic acid | 337.0933 | 22.6 | 9.95E+07 191 |
| 124 | 5-Coumaroylquinic acid | 337.0933 | 23.0 | 4.09E+08 163, 173 |
| 125 | 3-Coumaroylquinic acid dimer | 675.1941 | 19.0 | 0 |
| 126 | 4-Coumaroylquinic acid dimer | 675.1941 | 22.6 | 3.00E+06 191 |
| 127 | 5-Coumaroylquinic acid dimer | 675.1941 | 23.0 | 1.53E+07 163, 173 |
| 128 | 3,4-Dicaffeoyl quinic acid | 515.1189 | 27.1 | 2.63E+08 135, 161, 173, 179, 191, 353 |
| 129 | 3,5-Dicaffeoyl quinic acid | 515.1190 | 27.6 | 1.79E+08 135, 179, 191, 353 |
| 130 | 4,5-Dicaffeoyl quinic acid | 515.1195 | 28.3 | 3.37E+08 135, 173, 179, 191, 353 |
| 131 | Valeroylquinic acid isomer-1 | 275.1135 | 14.9 | 2.70E+05 101, 173, 181 |
| 132 | Valeroylquinic acid isomer-2 | 275.1135 | 15.8 | 5.75E+05 101, 181, 191 |
| 133 | Valeroylquinic acid isomer-3 | 275.1135 | 21.0 | 1.17E+06 101, 173 |
| 134 | Valeroylquinic acid isomer-4 | 275.1135 | 21.4 | 2.26E+06 101, 173 |
| 135 | Valeroylquinic acid isomer-5 | 275.1135 | 23.2 | 3.27E+05 93, 101, 173, 181, 191 |
| 136 | Valeroylquinic acid isomer-6 | 275.1135 | 23.4 | 5.25E+05 101, 173 |
| 137 | Valeroylquinic acid isomer-7 | 275.1135 | 30.4 | 5.22E+06 93, 101, 173, 181, 191 |
| 138 | Valeroylquinic acid isomer-8 | 275.1135 | 30.6 | 1.18E+06 101 |
| 139 | Valeroylquinic acid isomer-9 | 275.1135 | 31.7 | 1.98E+06 101, 173 |
| 140 | Caffeoylvaleroylquinic acid isomer 1 | 437.1451 | 29.7 | 3.55E+06 161, 173, 179, 275 |
| 141 | Caffeoylvaleroylquinic acid isomer 2 | 437.1451 | 29.8 | 6.88E+06 161, 173, 179, 275 |
| 142 | Caffeoylvaleroylquinic acid isomer 3 | 437.1451 | 30.4 | 2.46E+06 161, 173, 179, 275 |
| 143 | Caffeoylvaleroylquinic acid isomer 4 | 437.1451 | 30.6 | 5.13E+06 173, 275 |
| 144 | Caffeoylvaleroylquinic acid isomer 5 | 437.1451 | 31.7 | 6.96E+06 173, 275 |
| 145 | Quinic acid-glucoside-R*-1 | 481.2442 | 24.8 | 3.81E+07 161, 197, 301 |
| 146 | Quinic acid-glucoside-R*-2 | 481.2442 | 25.3 | 1.22E+08 161, 197, 301 |
| 147 | Valeroylquinic acid glucoside-R*-1 | 565.3023 | 33.3 | 1.18E+07 301, 463, 481 |
| 148 | Valeroylquinic acid diglucoside-R*-1 | 727.3545 | 26.6 | 3.83E+06 161, 301, 323, 481, 643 |
| 149 | Valeroylquinic acid diglucoside-R*-2 | 727.3545 | 30.4 | 1.89E+06 205, 361, 625, 643 |
| 150 | Valeroylquinic acid diglucoside-R*-3 | 727.3545 | 30.8 | 3.05E+07 481, 523, 625, 643 |

TABLE 7

| | | Betacyanin | | |
|---|---|---|---|---|
| 151 | Betanin | 551.1517 | 15.6 | 2.19E+04 |
| 152 | Isobetanin | 551.1517 | 19.7 | 1.54E+04 |

TABLE 8

| | Amino acids, alkaloids & other compounds | | | | |
|---|---|---|---|---|---|
| 153 | Glycerophosphocholine | 258.1098 | 1.7 | 6.17E+07 | 104 |
| 154 | Adenosine | 268.1040 | 4.1 | 4.68E+06 | 136 |
| 155 | Phenylalanine | 166.0861 | 6.8 | 1.41E+07 | 120 |
| 156 | Tryptophan | 205.0973 | 14.5 | 6.28E+06 | 146, 188 |
| 157 | Tyrosine | 182.0812 | 3.7 | 9.16E+06 | 119, 123, 136, 147, 165 |
| 158 | Dopamine | 154.0858 | 2.7 | 8.64E+05 | 113, 137 |
| 159 | Trigonellin | 138.0548 | 1.8 | 2.05E+08 | 94 |
| 160 | Caffeine | 195.0875 | 20.1 | 4.94E+07 | 138 |
| 161 | Xanthine | 151.0256 | 3.1 | 7.74E+05 | 109 |

Biological activity of the composition was tested for inhibition of various target entities that are central to various pathways associated with health and healthy ageing, and exemplary activity results are presented below. More specifically, the inventor tested the composition for inhibitory activity of human ARG-1, ARG-2, SIRT1, BACE1, Cathepsin S, CDK5, IDOL IDO2, NAMPT, PCSK9, CD47, CD38, JAK1, JAK2, JAK3, CD39, and CD73, and for Keap/Nrf2 binding inhibition and ACE2-Spike binding inhibition.

ARG1 and ARG2:

In the following experiments, the inventor sought to determine whether the representative compositions had an effect on ARG1 and ARG2. Reagents used are shown in the Tables 9-10 below and tested as stated unless indicated otherwise (nor-NOHA is reference compound).

TABLE 9

| Compound | Form Supplied | Stock Conc. | Dissolving Solvent | Test Range |
|---|---|---|---|---|
| HP Color Blend lot#33890000X11020 | powder | 1% (w/v) | 70% EtOH | 0.0004, 0.002 and 0.01% |
| nor-NOHA* | powder | 10 mM | DMSO | 0.001, 0.01 and 0.1 µM |

TABLE 10

| Enzyme | Lot # | Concentration (ng/well) | Substrate |
|---|---|---|---|
| ARG1 | 150825 | 100 | Thioarginine (225 µM) |
| ARG2 | 160726-1 | 20 | Thioarginine (225 µM) |

Assay conditions: The assay was performed using human recombinant ARG1 or ARG2 as enzymes and thioarginine as substrate. The UV absorbance at 412 nm was correlated with the amount of reaction product of ARG1/ARG2. The test sample (HP Color Blend) was dissolved to 1% (w/v) with 70% (w/v) EtOH and filtered through 0.22 µm; nor-NOHA was dissolved in 100% (w/v) DMSO to 10 mM. 5 µl of 20× sample solutions were added to 90 µl of substrate, and reactions were started by the addition of 5 µl of 20×ARG1/ARG2 solutions. For the negative control (Blank), 5 µl of the assay buffer was added instead of the ARG1/ARG2. The resulting 100 µl reaction mixture contained the indicated amount of the samples, 225 µM thioarginine, the detection reagent, and 30 nM ARG1 or 5 nM ARG2 in 1× ARG Assay Buffer. All reactions were conducted at room temperature and incubated for 30 minutes, ensuring that all wells, containing either samples or controls, contained 0.7% (v/v) EtOH final concentration to discard any solvent effect. UV absorbance readings were done at times 0 and 30 minutes to get net values. Absorbance was measured using a Tecan Infinite M1000 microplate reader.

Data Analysis: Experiment was performed in duplicate at each concentration. The data were analyzed using the software GraphPad Prism. In the absence of the compound, the net absorbance ($A_t$) in each data set was defined as 100% activity. In the absence of ARG1/ARG2, the net absorbance ($A_b$) in each data set was defined as 0% activity. The percent activity in the presence of each compound was calculated according to the following equation: % activity=$[(A-A_b)/(A_t-A_b)]\times 100$, where A=the absorbance in the presence of the compound. The percent inhibition was calculated according to the following equation: % inhibition=100-% activity.

Figure 2:
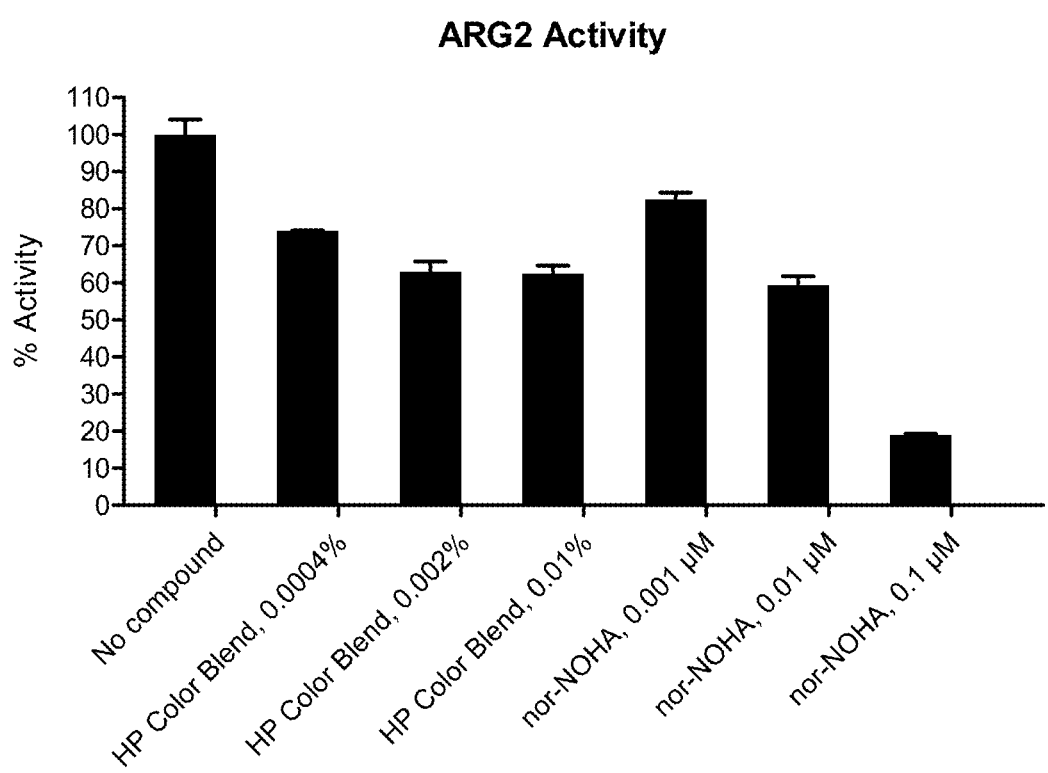
FIG. 2 is a graph depicting exemplary results for ARG-2 inhibition using a composition according to the inventive subject matter.

Results: Notably, significant inhibitory activity was found for both ARG-1 and ARG-2 across all tested concentrations as is shown in Tables 11-12 below. As can be readily seen from the results, inhibition relative to the reference inhibitor was significant and not specific towards one or the other of ARG-1 and ARG-2 as is also seen from Table 13. Results are also depicted in FIG. 1 and FIG. 2 for ARG-1 and ARG-2, respectively.

TABLE 11

| | Net absorbance | | Activity (%) | | ARG-1 Inhibition |
|---|---|---|---|---|---|
| Condition | Rep. 1 | Rep.2 | Rep. 1 | Rep.2 | (%) |
| No compound | 0.76 | 0.75 | 101 | 99 | |
| HP Color Blend, 0.0004% | 0.64 | 0.62 | 85 | 82 | 17 |
| HP Color Blend, 0.002% | 0.56 | 0.55 | 74 | 74 | 26 |
| HP Color Blend, 0.01% | 0.51 | 0.50 | 68 | 66 | 33 |
| nor-NOHA, 0.001 µM | 0.74 | 0.77 | 99 | 102 | 0 |
| nor-NOHA, 0.01 µM | 0.59 | 0.59 | 79 | 78 | 22 |
| nor-NOHA, 0.1 µM | 0.23 | 0.24 | 31 | 31 | 69 |
| Blank | 0.00 | 0.00 | | | |

TABLE 12

| | Net absorbance | | Activity (%) | | ARG-2 Inhibition |
|---|---|---|---|---|---|
| Condition | Rep. 1 | Rep.2 | Rep. 1 | Rep.2 | (%) |
| No compound | 1.01 | 0.93 | 104 | 96 | |
| HP Color Blend, 0.0004% | 0.72 | 0.72 | 74 | 74 | 26 |
| HP Color Blend, 0.002% | 0.59 | 0.64 | 60 | 66 | 37 |
| HP Color Blend, 0.01% | 0.63 | 0.59 | 65 | 60 | 38 |
| nor-NOHA, 0.001 µM | 0.78 | 0.82 | 81 | 84 | 17 |
| nor-NOHA, 0.01 µM | 0.56 | 0.60 | 57 | 62 | 41 |
| nor-NOHA, 0.1 µM | 0.19 | 0.19 | 19 | 19 | 81 |
| Blank | 0.00 | 0.00 | 0 | 0 | |

TABLE 13

| Condition | Inhibition (%) | |
|---|---|---|
| | ARG1 | ARG2 |
| HP Color Blend, 0.0004% | 17 | 26 |
| HP Color Blend, 0.002% | 26 | 37 |
| HP Color Blend, 0.01% | 33 | 38 |
| nor-NOHA, 0.001 µM | 0 | 17 |
| nor-NOHA, 0.01 µM | 22 | 41 |
| nor-NOHA, 0.1 µM | 69 | 81 |

SIRT1:

In the following experiments, the inventor sought to determine whether the representative compositions had an effect on SIRT1. Reagents used are shown in Tables 14-15 below and tested as stated unless indicated otherwise (Suramin was used as reference compound).

TABLE 14

| Compound I.D. | Compound Supplied | Stock Concentration | Dissolving Solvent | Test Range | Intermediate Dilution |
|---|---|---|---|---|---|
| HP Color Blend lot#33890000X11020 | Solid | 1% (w/v) | 70% EtOH | 0.0004%, 0.002%, 0.01% | 10 % DMSO in HDAC Assay Buffer |
| Suramin* | Solid | 10 mM | DMSO | 0.01 µM, 0.1 µM, 1 µM | 10 % DMSO in HDAC Assay Buffer |

TABLE 15

| Assay | Catalog # | Enzyme Lot # | Enzyme Used (ng)/Reaction | Substrate |
|---|---|---|---|---|
| SIRT1 | 50012 | 190710 | 550 | 10 µM HDAC Substrate 1 |

Assay Conditions: The sample was dissolved in 70% EtOH. The serial dilution of the compound was first performed in 70% EtOH with the highest concentration at 1%. Each intermediate compound dilution (in 70% EtOH) will then get directly diluted 10× fold into assay buffer for an intermediate dilution of 7% EtOH in HDAC assay buffer and 5 µl of the dilution was added to a 50 µl reaction so that the final concentration of EtOH is 0.7% in all of reactions.

The enzymatic reactions for the SIRT1 enzyme were conducted in duplicate at 37° C. for 30 minutes in a 50 µl mixture containing SIRT assay buffer, 5 µg BSA, an HDAC substrate (see 2.3.1), a SIRT enzyme, and a test compound. After enzymatic reactions, 50 µl of 2×SIRT Developer was added to each well for the SIRT enzymes and the plate was incubated at room temperature for an additional 15 minutes. Fluorescence intensity was measured at an excitation of 360 nm and an emission of 460 nm using a Tecan Infinite M1000 microplate reader.

Data Analysis: SIRT activity assays were performed in duplicates at each concentration. The fluorescent intensity data were analyzed using the computer software, Graphpad Prism. In the absence of the compound, the fluorescent intensity (Ft) in each data set was defined as 100% activity. In the absence of SIRT, the fluorescent intensity (Fb) in each data set was defined as 0% activity. The percent activity in the presence of each compound was calculated according to the following equation: % activity=$(F-F_b)/(F_t-F_b)$, where F=the fluorescent intensity in the presence of the compound.

Figure 3:
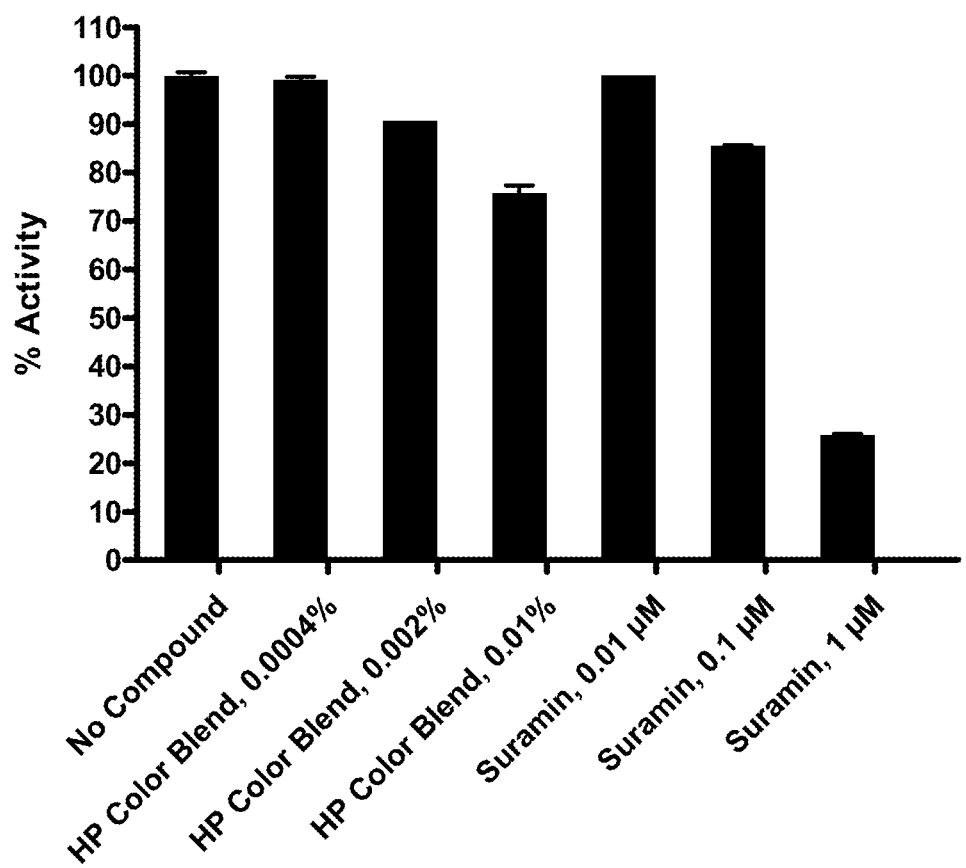
FIG. 3 is a graph depicting exemplary results for SIRT1 inhibition using a composition according to the inventive subject matter.

Results: The inhibitory results are shown in the table below. The percent inhibition of the compounds against SIRT1 are summarized. The reference compound and tested composition and HP Color Blend precipitated at the 0.01% intermediate dilution step. FIG. 3 depicts the results in graphic form, and Table 16 provides results in numerical format. As can be readily appreciated, the tested composition had noticeable SIRT1 inhibitory activity.

TABLE 16

| Compound I.D. | SIRT1 Activity (Fluorescence count) | | % Activity | | % Inhibition |
|---|---|---|---|---|---|
| | Repeat 1 | Repeat 2 | Repeat 1 | Repeat 2 | |
| No Compound | 2394 | 2429 | 99 | 101 | 0 |
| HP Color Blend, 0.0004% | 2407 | 2382 | 100 | 99 | 1 |
| HP Color Blend, 0.002% | 2199 | 2200 | 91 | 91 | 9 |
| HP Color Blend, 0.01% | 1821 | 1891 | 74 | 77 | 24 |
| Suramin, 0.01 µM | 2415 | 2415 | 100 | 100 | 0 |
| Suramin, 0.1 µM | 2074 | 2082 | 85 | 86 | 14 |
| Suramin, 1 µM | 710 | 702 | 26 | 26 | 74 |
| Background | 109 | 110 | | | |

Keap/Nrf2:

In a further set of experiments, the inventor investigated whether or not the tested composition was able to interfere with Keap1-Nrf2 binding, and exemplary results are provided below. Reagents used are shown in Table 17 below and tested as stated unless indicated otherwise (reference compound was LDEETGEFL-OH).

TABLE 17

| Compound I.D. | Compound Supplied | Stock Concentration | Dissolving Solvent | Test Range (%) | Intermediate Dilution |
|---|---|---|---|---|---|
| HP Color Blend lot#33890000X11020 | Powder | 1% | 70% Ethanol | 0.0004, 0.002, 0.01 | 7% Ethanol |
| Reference | Powder | 10 mM | DMSO | 0.1, 1, 10, 100 | 10% DMSO |

Assay Conditions: The test compound is diluted in 7% ethanol, and 5 µl of the dilution was added to a 50 µl reaction so that the final concentration of ethanol is 0.7%. The reference compound is diluted in 10% DMSO, and 5 µl of the dilution was added to a 50 µl reaction so that the final concentration of DMSO is 1%. The binding reactions were conducted at room temperature for 30 minutes in a 50 µl mixture containing 10 mM HEPES, pH7.4, 50 mM EDTA, 150 mM NaCl, 0.05% Tween20, 0.01% BSA, 100 nM Keap1, 5 nM fluorescence probe and the test compound. Fluorescence intensity was measured at an excitation of 475 nm and an emission of 520 nm using a Tecan Infinite M1000 microplate reader.

Data Analysis: All of binding assays were performed in 96-well plates in duplicate. Fluorescence intensity is converted to fluorescence anisotropy using the Tecan Magellan6 software. The fluorescence anisotropy data were analyzed using the computer software, Graphpad Prism. The fluorescence anisotropy ($F_{At}$) in the sample with Keap1 and the probe in each data set was defined as 100% activity. The fluorescence anisotropy ($F_{Ab}$) in the sample with a compound but without Keap1 in each data set was defined as 0% activity. The percent binding efficacy in the presence of the competitor compound was calculated according to the following equation $$\% \text{ Activity} = \frac{(F_A - F_{Ab})}{(F_{At} - F_{Ab})} \times 100\%$$

where $F_A$=the fluorescence anisotropy in the presence of the compound. The values of % binding were then plotted in a bar graph as shown in FIG. 4, and numerical results are shown in Table 18 below.

TABLE 18

| Compound | Background Fluorescent Polarization (mA) | | Binding Activity Fluorescent Polarization (mA) | | Percentage Activity | | Percentage Inhibition |
|---|---|---|---|---|---|---|---|
| | Repeat1 | Repeat2 | Repeat2 | Repeat2 | Repeat2 | Repeat2 | |
| No Compound | 18 | 14 | 38 | 40 | 96 | 104 | 0 |
| 0.0004% | 21 | 22 | 43 | 43 | 92 | 93 | 7 |
| 0.002% | 38 | 41 | 48 | 50 | 39 | 48 | 56 |
| 0.01% | 78 | 76 | 81 | 81 | 16 | 17 | 83 |

Figure 4:
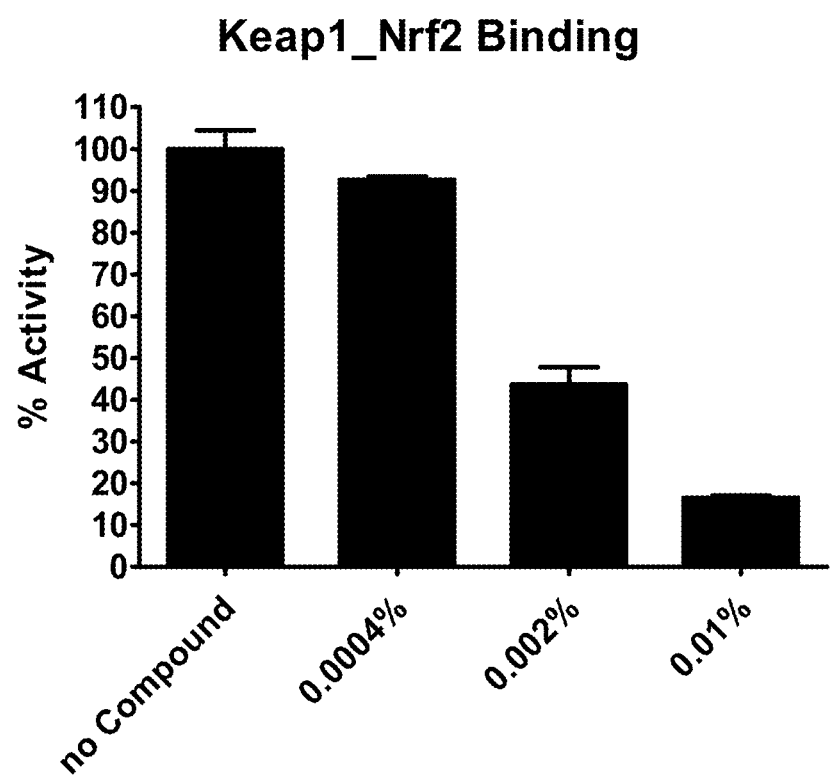
FIG. 4 is a graph depicting exemplary results for Keap1-Nrf2 binding inhibition using a composition according to the inventive subject matter.

As will be readily recognized from the results in the Table above and FIG. 4, the tested composition had appreciable inhibitory activity against Keap1-Nfr2 binding.

ACE2-Spike:

In this series of experiments, the inventor investigated whether contemplated compositions and fractions thereof could reduce binding of SARS-CoV2 spike protein to ACE2, and if vitamins would also have any effect.

Reagents used are shown in Tables 19-21 below and tested as stated unless indicated otherwise (* denotes reference compounds). In this series of experiments, the representative composition as described above was compared against individual color as indicated below and further against a multivitamin formulation as also indicated below. Table 19 denotes the representative composition, Table 20 denotes the color subfractions of the representative composition in which DC-5=Yellow Blend, DC-9=Purple Blend, DC-21-Green Blend, DC-13=Red Blend. Here, the red blend included Apple Extract, Pomegranate Extract, Tomato Powder, Beet; the green blend included Olive Extract, Rosemary Extract, Green Coffee Bean Extract, Kale; the orange/yellow blend included Onion Extract, Ginger Extract, Grapefruit Extract, Carrot; and the purple/blue blend included Grape, Blueberry Extract, Currant, Elderberry as also noted above. Table 21 denotes the multivitamin blend, and Table 22 denotes the ACE2/Spike reagents used.

TABLE 19

| Sample | Form Supplied | Stock Conc. | Dissolving Solvent | Test Range |
|---|---|---|---|---|
| HP Color Blend lot#33890000X11020 | Powder | 1% (w/v) | 70% EtOH | 0.0008, 0.004, 0.02 and 0.1% |
| Anti-ACE2* | Powder | 1.33 μM | PBS | 0.27 μM |
| Spike S1* | Solution | 5.6 μM | PBS | 0.01, 0.1 and 1 μM |

TABLE 20

| Sample | Form Supplied | Stock Conc. | Dissolving Solvent | Test Range |
|---|---|---|---|---|
| DC-5 | Solid | 1% (w/v) | 70% (v/v) EtOH | 0.0008, 0.004, 0.02 and 0.1% |
| DC-9 | Solid | 1% (w/v) | 70% (v/v) EtOH | 0.0008, 0.004, 0.02 and 0.1% |

TABLE 20-continued

| Sample | Form Supplied | Stock Conc. | Dissolving Solvent | Test Range |
|---|---|---|---|---|
| DC-13 | Solid | 1% (w/v) | 70% (v/v) EtOH | 0.0008, 0.004, 0.02 and 0.1% |
| DC-21 | Solid | 1% (w/v) | 70% (v/v) EtOH | 0.0008, 0.004, 0.02 and 0.1% |
| Anti-ACE2* | Solid | 13.3 μM | PBS | 0.27 μM |
| Spike S1* | Solution | 5.6 μM | PBS | 0.01, 0.1 and 1 μM |

TABLE 21

| Sample | Form Supplied | Stock Conc. | Dissolving Solvent | Test Range |
|---|---|---|---|---|
| DC-TIV-1.0 (Adult Centrum Vitamin) | Powder | 1% (w/v) | 70% (v/v) EtOH | 0.0008, 0.004, 0.02 and 0.1% |
| Anti-ACE2* | Powder | 13.3 μM | PBS | 0.27 μM |
| Spike S1* | Solution | 5.6 μM | PBS | 0.01, 0.1 and 1 μM |

TABLE 22

| Component | Catalog # | Lot # | Concentration |
|---|---|---|---|
| ACE2-His | 11003 | 131001 | 50 ng/well |
| Spike 51-Biotin | 100679 | 200326 | 40 nM |

Assay Conditions: Nickel plate was coated at room temperature for 1 hour with 50 μl of 1 μg/ml of ACE2-His and washed and blocked before starting the reaction. 10 μl of compound solutions were incubated with 20 μl of 1× Immune Buffer in ACE2-His-coated assay wells during 30 minutes before starting the reaction by the addition of 20 μl of 5 μg/ml Spike S1-Spike. Controls with the same concentration of solvent (EtOH) were included in the study. Reaction was progressed for 1 hour at room temperature. Then, wells were washed three times with 1× Immune Buffer and blocked with Blocking Buffer 2 for 10 minutes. 100 μl of Streptavidin-HRP was added to all wells and incubated for 1 hour. Lastly, plate was emptied, washed three times and blocked before the addition of 100 μl of freshly prepared HRP chemiluminescent substrates to every well. Immediately, the luminescence of the samples was measured in a BioTek Synergy 2 microplate reader.

Data Analysis: The luminescence data were analyzed and compared. In the absence of the compound, the intensity ($C_e$) in each data set was defined as 100% activity. In the absence of enzyme, the intensity ($C_0$) in each data set was defined as 0% activity. The percent activity in the presence of each compound was calculated according to the following equation: % activity=$(C-C_0)/(C_e-C_0)$, where C=the luminescence in the presence of the compound.

Figure 5:
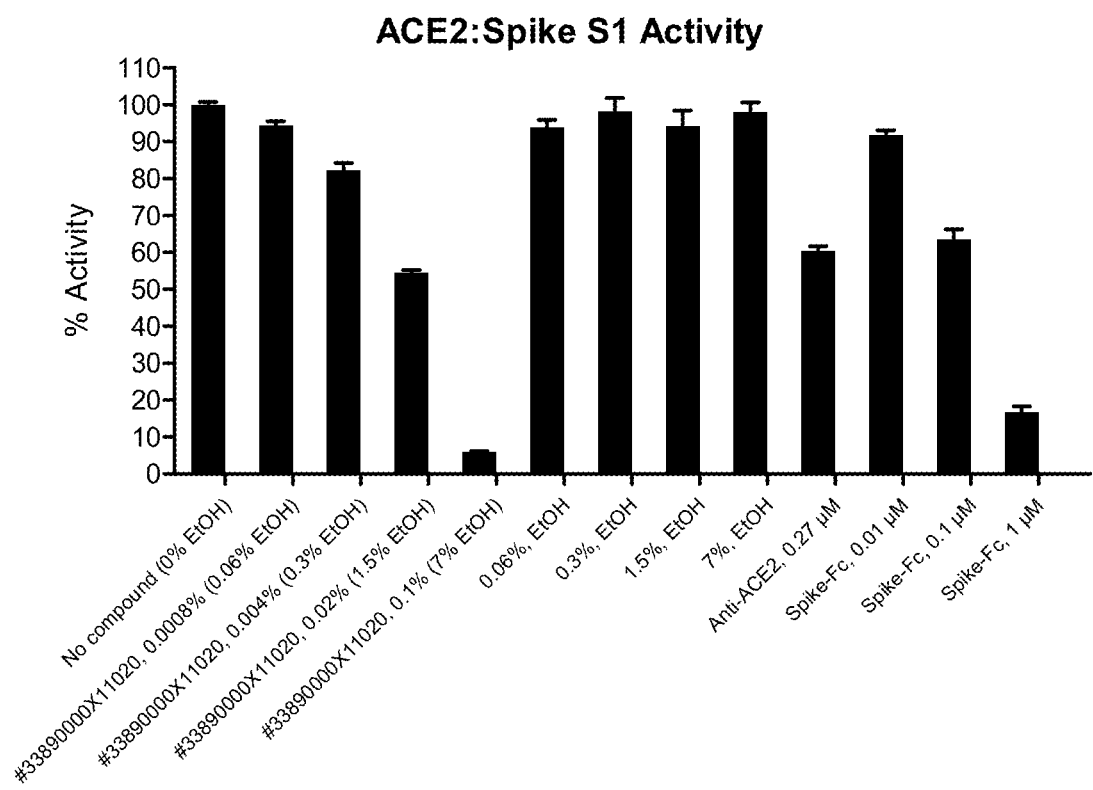
FIG. 5 is a graph depicting exemplary results for ACE2-Spike S1 binding inhibition using a composition according to the inventive subject matter.
Figure 6:
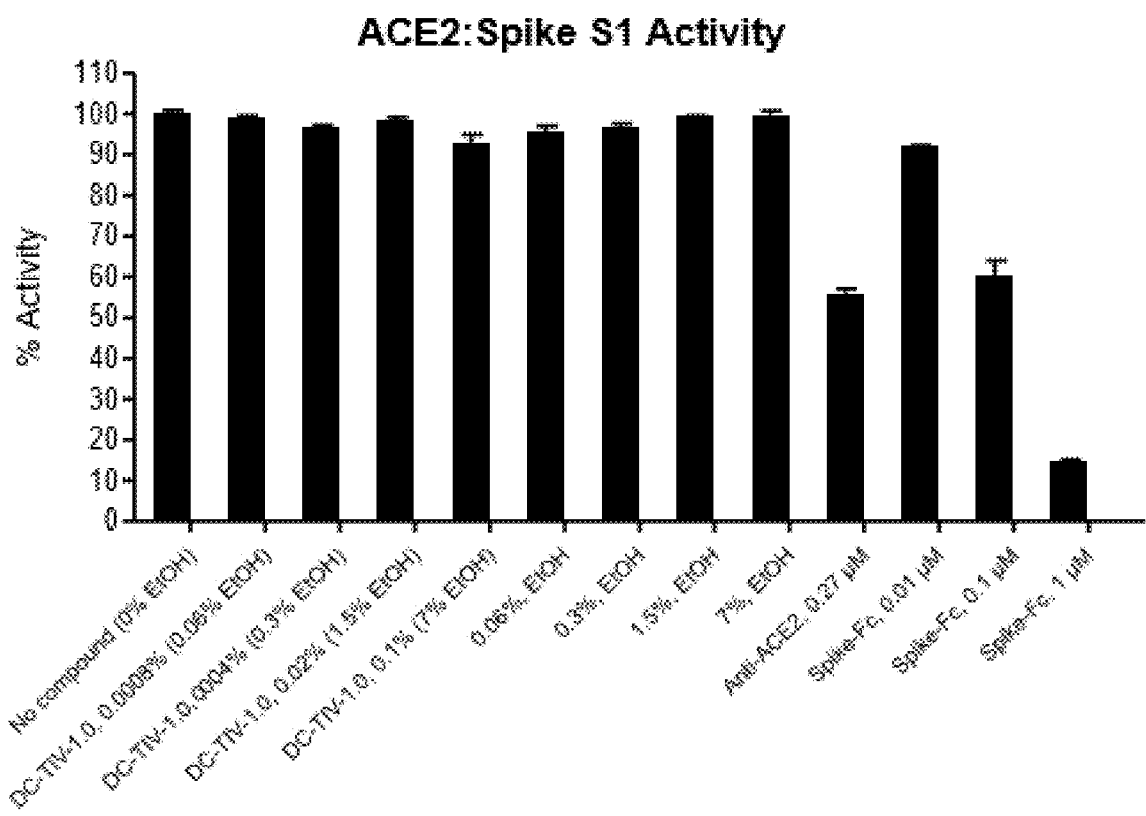
FIG. 6 is a graph depicting exemplary results for ACE2-Spike S1 binding inhibition using a multivitamin composition.
Figure 7:
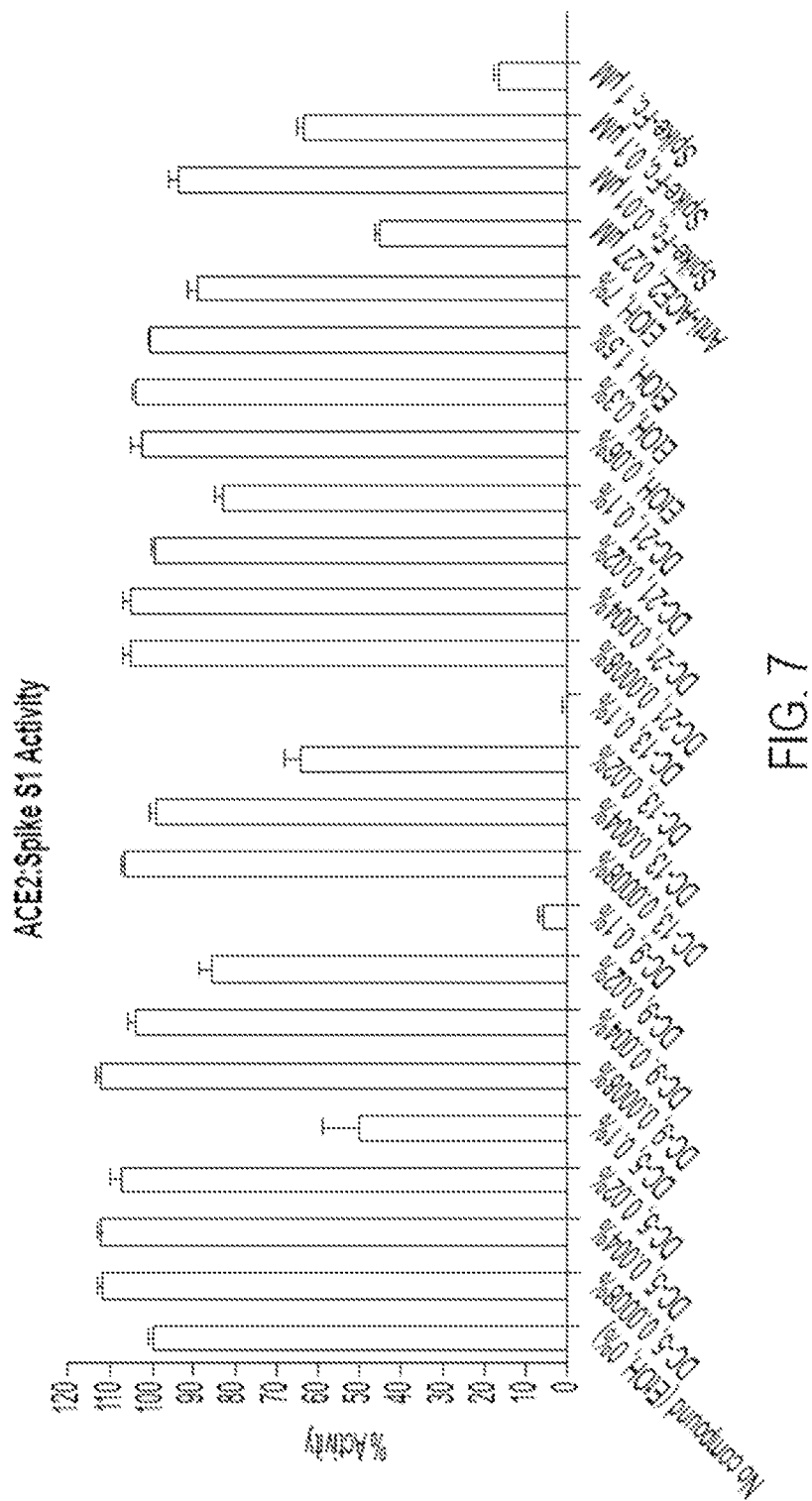
FIG. 7 is a graph depicting exemplary results for ACE2-Spike S1 binding inhibition using various further compositions according to the inventive subject matter.

Results for the representative composition are shown in Table 23 and FIG. 5, while results for the multivitamin formulation are shown in Table 24 and FIG. 6. Results for the colored blends are shown in Table 25 and FIG. 7. As can be readily seen from the data in Tables 23-25 and FIGS. 5-7, the representative composition showed synergistic inhibition of ACE2-Spike 51 binding, particularly at lower concentrations, whereas the multivitamin formulation had TABLE 27-continued

| Sample | Form Supplied | Stock Conc. | Dissolving Solvent | Test Range |
|---|---|---|---|---|
| DC-13 | Powder | 1% (w/v) | 70% EtOH | 0.0004, 0.002 and 0.01% |
| DC-21 | Powder | 1% (w/v) | 70% EtOH | 0.0004, 0.002 and 0.01% |
| DCH-TIV 1.0 | Powder | 1% (w/v) | 70% EtOH | 0.0004, 0.002 and 0.01% |
| Verubecestat* | Powder | 10 mM | 100% DMSO | 0.01, 0.1 and 1 μM |

TABLE 28

| Assay | Catalog # | Protein lot # | [E] (ng/well) | Substrate |
|---|---|---|---|---|
| BACE1 | 71657 | 170307 | 500 | 7.5 μM BACE1 FRET peptide substrate |

Assay Conditions: 80 μl of BACE1 was incubated with 10 μl of samples and reference compound for 10 minutes. Then, reaction was started by the addition of 10 μl of BACE1 FRET peptide substrate and product kinetics were measured for 1 hour in an Infinite M1000 microplate reader (Tecan). In Blank control wells, 80 μl of assay buffer was added instead of enzyme, all wells contained 0.7% (v/v) EtOH final assay concentration.

Data Analysis: All conditions were performed in duplicates at each concentration. The fluorescent intensity data was analyzed using Prism (GraphPad). In the absence of the compound (No compound control), the fluorescent intensity (Ft) in each data set was defined as 100% activity. In the absence of the enzyme (Blank control), the fluorescent intensity (Fb) in each data set was defined as 0% activity. The percent activity in the presence of each compound was calculated according to the following equation: % Activity=(F−Fb)/(Ft−Fb), where F=the fluorescent intensity in the presence of the compound. Fluorescence at initial time was subtracted to obtain net signal, measured in relative fluorescence units (RLU).

Figure 8:
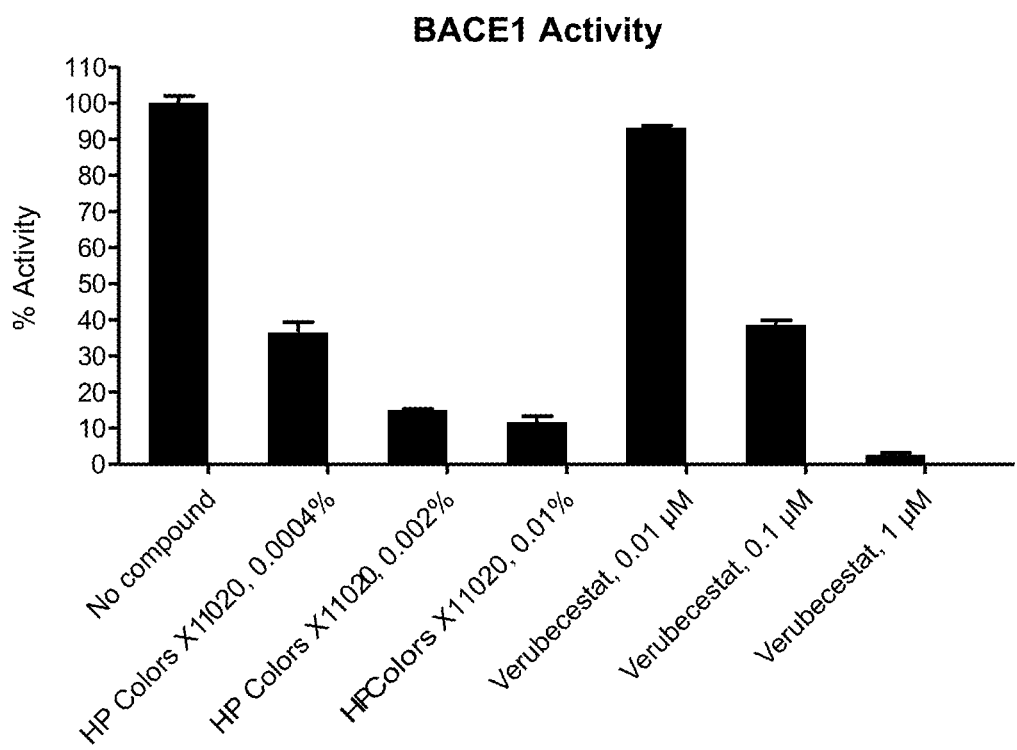
FIG. 8 is a graph depicting exemplary results for BACE1 inhibition using a composition according to the inventive subject matter.
Figure 9:
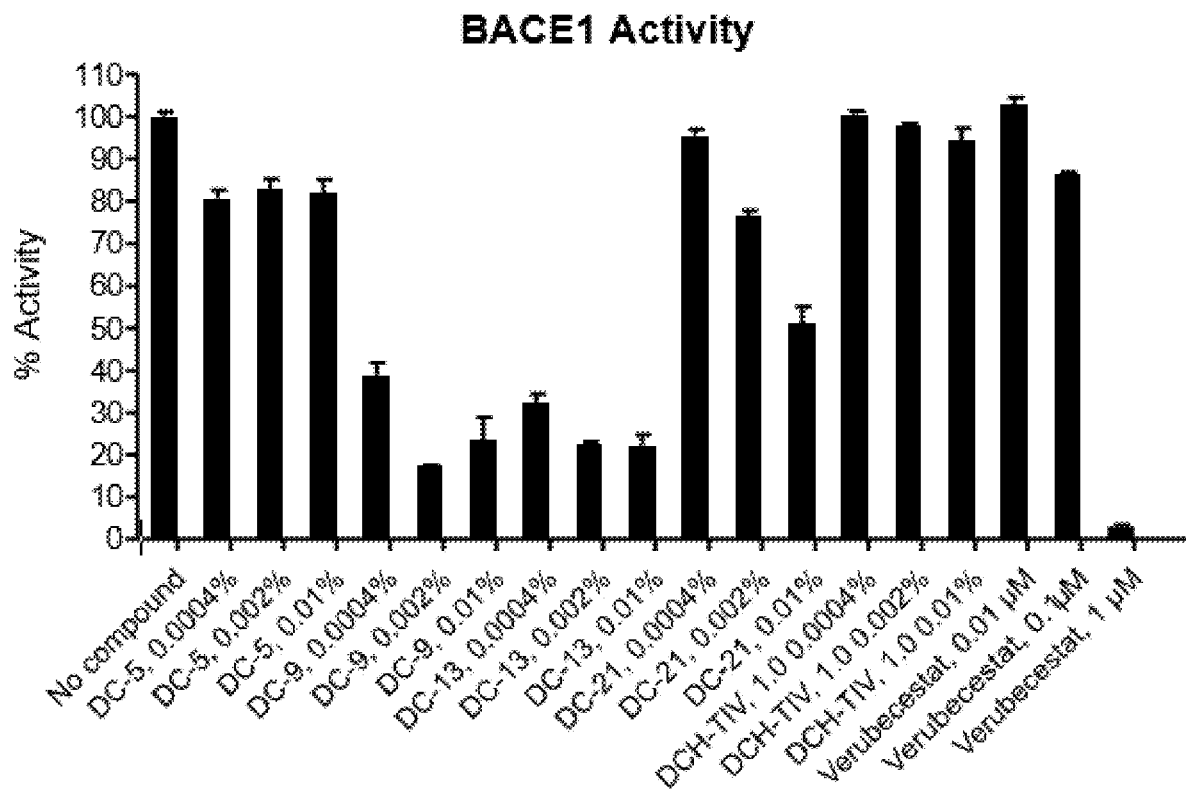
FIG. 9 is a graph depicting exemplary results for BACE1 inhibition using various further compositions according to the inventive subject matter and a multivitamin composition.

As can be seen form the data in Table 29 and FIG. 8, the representative composition had substantial inhibitory activity against BACE1 as tested. Remarkably, as can be seen from the data in Table 30 and FIG. 9, the colored fractions also provided significant inhibition of BACE1. Moreover, it is also evident from these data that the BACE1 inhibition is synergistic, while the tested multivitamin had substantially no inhibitory effect.

TABLE 29

| | Fluorescence (net RFU) | | Activity (%) | | Inh. |
|---|---|---|---|---|---|
| Condition | Rep. 1 | Rep. 2 | Rep. 1 | Rep. 2 | (%) |
| No compound | 419 | 403 | 102 | 98 | 0 |
| #33890000X11020, 0.0004% | 166 | 143 | 39 | 34 | 63 |
| #33890000X11020, 0.002% | 69 | 66 | 15 | 15 | 85 |
| #33890000X11020, 0.01% | 47 | 61 | 10 | 13 | 88 |
| Verubecestat, 0.01 μM | 381 | 386 | 93 | 94 | 7 |
| Verubecestat, 0.1 μM | 168 | 158 | 40 | 37 | 61 |
| Verubecestat, 1 μM | 16 | 20 | 2 | 3 | 97 |
| Blank | 8 | 6 | | | |

TABLE 30

| | Fluorescence (net RFU) | | Activity (%) | | Inh. |
|---|---|---|---|---|---|
| Condition | Rep. 1 | Rep. 2 | Rep. 1 | Rep. 2 | (%) |
| No compound | 779 | 795 | 99 | 101 | |
| DC-5, 0.0004% | 651 | 620 | 83 | 79 | 19 |
| DC-5, 0.002% | 671 | 636 | 85 | 81 | 17 |
| DC-5, 0.01% | 670 | 622 | 85 | 79 | 18 |
| DC-9, 0.0004% | 332 | 286 | 42 | 36 | 61 |
| DC-9, 0.002% | 138 | 142 | 17 | 18 | 83 |
| DC-9, 0.01% | 231 | 146 | 29 | 18 | 76 |
| DC-13, 0.0004% | 241 | 274 | 30 | 34 | 68 |
| DC-13, 0.002% | 184 | 176 | 23 | 22 | 78 |
| DC-13, 0.01% | 158 | 198 | 20 | 25 | 78 |
| DC-21, 0.0004% | 739 | 763 | 94 | 97 | 5 |
| DC-21, 0.002% | 592 | 613 | 75 | 78 | 24 |
| DC-21, 0.01% | 436 | 375 | 55 | 47 | 49 |
| DCH-TIV 1.0, 0.0004% | 797 | 784 | 101 | 100 | 0 |
| DCH-TIV 1.0, 0.002% | 767 | 774 | 97 | 98 | 2 |
| DCH-TIV 1.0, 0.01% | 765 | 721 | 97 | 92 | 6 |
| Verubecestat, 0.01 μM | 821 | 793 | 104 | 101 | 0 |
| Verubecestat, 0.1 μM | 684 | 676 | 87 | 86 | 14 |
| Verubecestat, 1 μM | 27 | 31 | 3 | 3 | 97 |
| Blank | 8 | 1 | | | |

Cathepsin S:

In yet another set of experiments, the inventor sought to determine whether the representative compositions and fractions thereof as well as a multivitamin mix had an effect on the activity of recombinant human Cathepsin S using an in vitro enzymatic assay.

Reagents used are shown in Tables 31-33 below and tested as stated unless indicated otherwise (*E-64 was used as reference compound). Here, the designations and ingredients of D5, D9, D13, and D21 are as noted above.

TABLE 31

| Sample | Form Supplied | Stock Conc. | Dissolving Solvent | Test Range |
|---|---|---|---|---|
| HP Color Blend lot#33890000X11020 | Powder | 1% (w/v) | 70% EtOH | 0.004, 0.02 and 0.1% |
| E-64 | Solution | 1 mM | DMSO | 1, 10 and 100 nM |

TABLE 32

| Sample | Form Supplied | Stock Conc. | Dissolving Solvent | Test Range |
|---|---|---|---|---|
| D5 | Powder | 1% (w/v) | 70% EtOH | 0.0004, 0.002 and 0.01% |
| D9 | Powder | 1% (w/v) | 70% EtOH | 0.0004, 0.002 and 0.01% |
| D13 | Powder | 1% (w/v) | 70% EtOH | 0.0004, 0.002 and 0.01% |
| D21 | Powder | 1% (w/v) | 70% EtOH | 0.0004, 0.002 and 0.01% |
| E-64 | Solution | 1 mM | DMSO | 1, 10 and 100 nM |

TABLE 33

| Sample | Form Supplied | Stock Conc. | Dissolving Solvent | Test Range |
|---|---|---|---|---|
| DCH-TIV-0.5 | Powder | 1% (w/v) | 70% EtOH | 0.004, 0.02 and 0.1% |
| DCH-TIV-1.0 (Adult Centrum Multivitamin) | Powder | 1% (w/v) | 70% EtOH | 0.004, 0.02 and 0.1% |
| E-64* | Solution | 1 mM | DMSO | 0.001, 0.01 and 0.1 μM |

Assay Conditions: Cathepsin S was activated by diluting the concentrated storage stock into the acidic assay buffer for 30 minutes at room temperature. Then, 5 µl of the sample or reference inhibitor was added to 20 µl of enzyme solution and pre-incubated for 30 minutes. The enzymatic reactions were started by the addition of 25 µl of the fluorogenic substrate, for a total reaction volume of 50 µl. Reaction time was 60 minutes, and then fluorescence intensity at an excitation of 360 nm and an emission of 460 nm was read using a Tecan Infinite M1000 microplate reader.

Data Analysis: Enzyme activity assays were performed in duplicates at each concentration. The fluorescence intensity data were analyzed and compared. In the absence of the compound, the intensity in each data set was defined as 100% (Ce) activity. In the absence of enzyme, the intensity in each data set was defined as 0% (C0) activity. The percent activity in the presence of each compound was calculated according to the following equation: % activity=(C−C0)/(Ce−C0), where C=the intensity in the presence of the compound (all percent activities below zero were shown zero in the table). Compound fluorescence was removed by subtracting fluorescence at reaction time=0.

Figure 10:
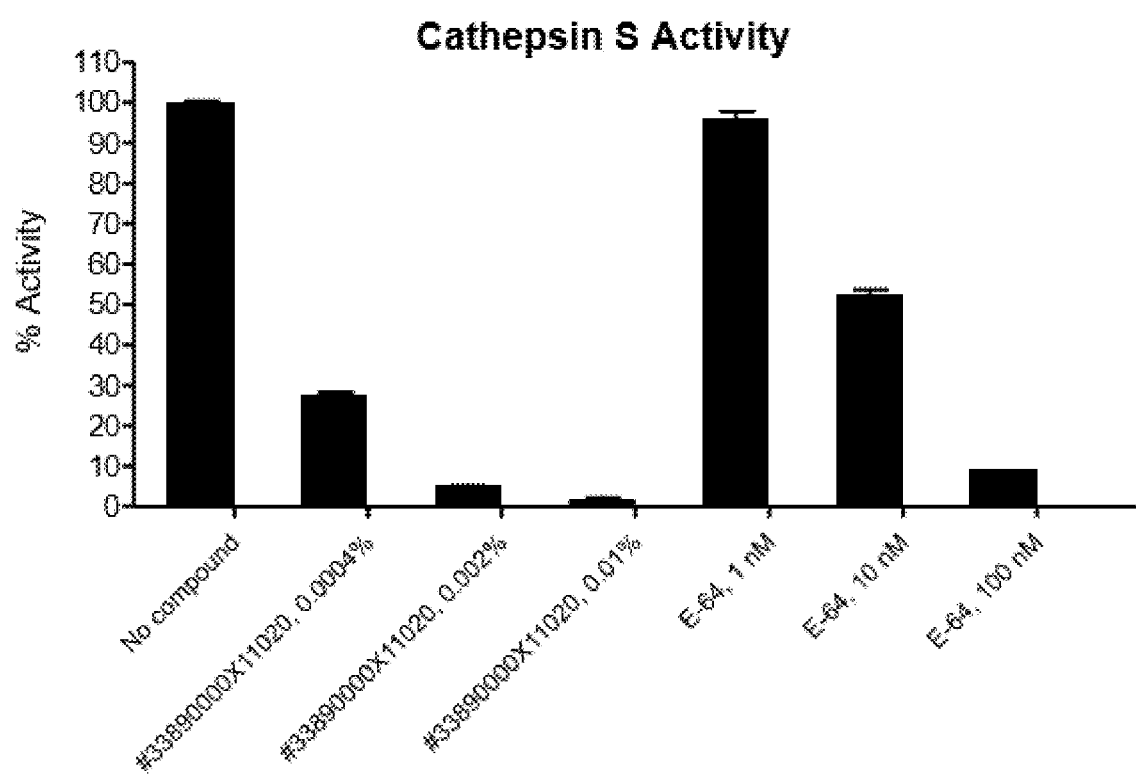
FIG. 10 is a graph depicting exemplary results for Cathepsin S inhibition using a composition according to the inventive subject matter.
Figure 11:
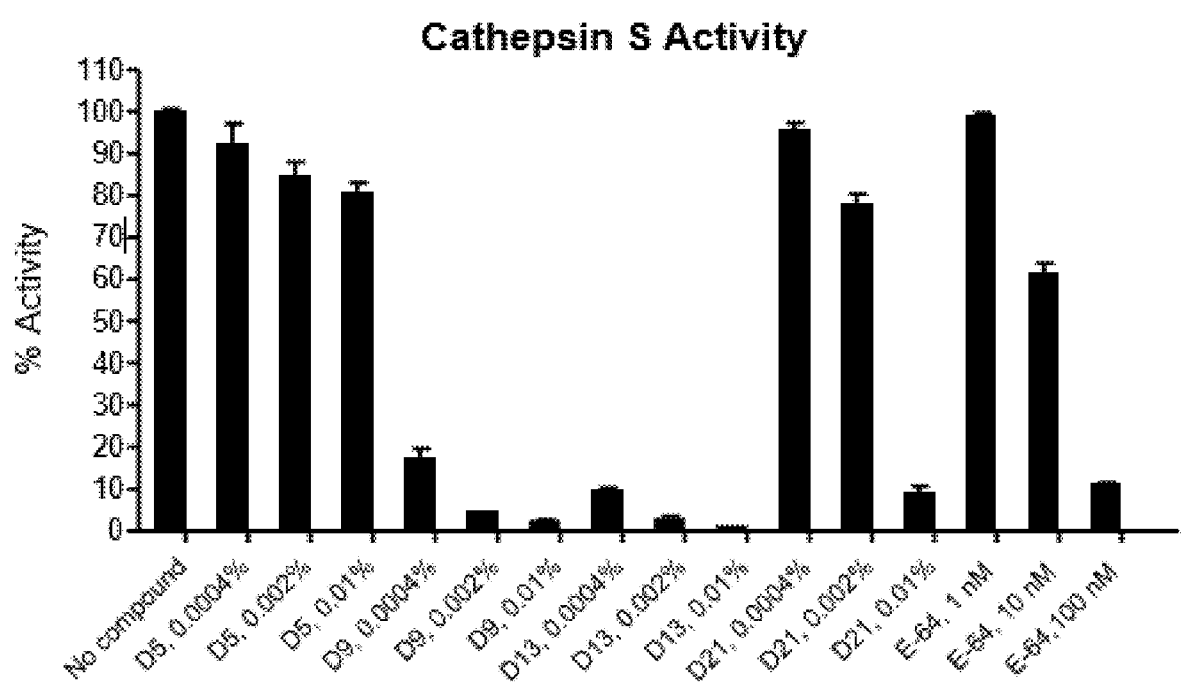
FIG. 11 is a graph depicting exemplary results for Cathepsin S inhibition using various further compositions according to the inventive subject matter.
Figure 12:
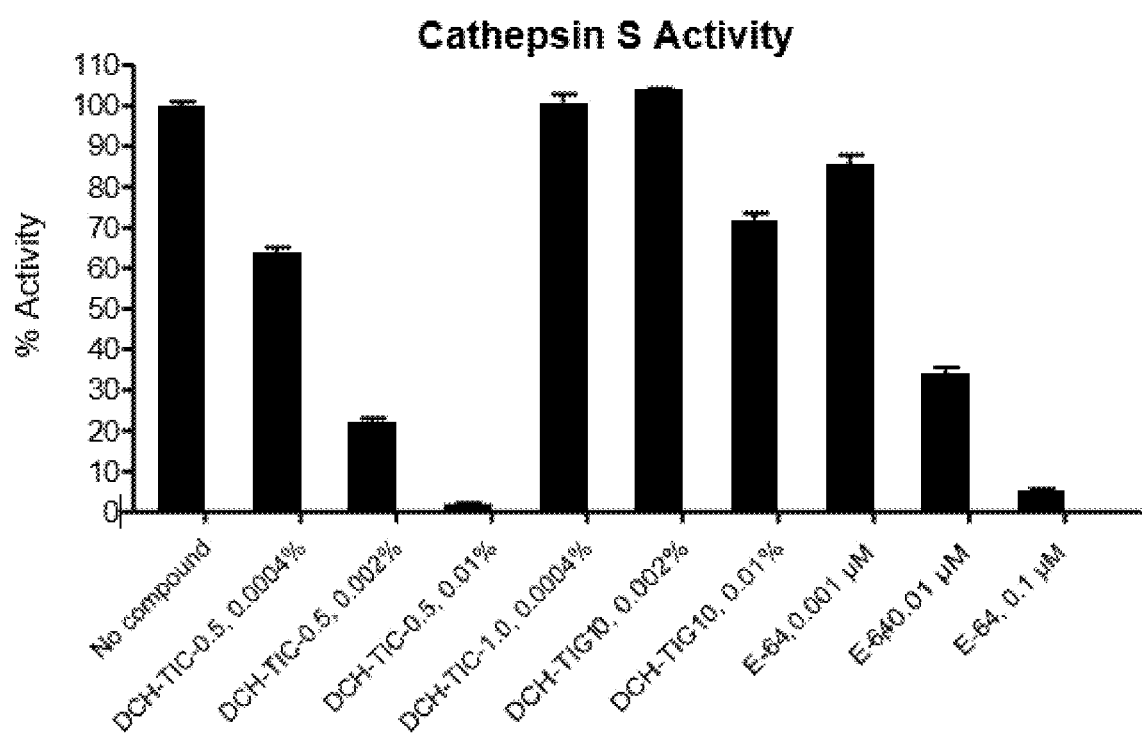
FIG. 12 is a graph depicting exemplary results for Cathepsin S inhibition using a composition according to the inventive subject matter and a multivitamin composition.

The results for the above tests are shown in Tables 34-36, with Table 34 and FIG. 10 showing results for the representative composition, Table 35 and FIG. 11 showing results for the various colored fractions, and Table 36 and FIG. 12 showing results for the multivitamin mixture (DCH-TIC-0.5 is representative composition; DCH-TIC-1.0 is Centrum multivitamin mix). As can be readily seen form the results, the representative composition as well as colored blends D9 and D13 had significant inhibition of Cathepsin S, whereas the multivitamin mix had comparably no substantial effect.

TABLE 34

| Condition | Net Signal (Fluorescence counts) | | Activity (%) | | Inhibition (%) |
|---|---|---|---|---|---|
| | Repeat 1 | Repeat 2 | Repeat 1 | Repeat 2 | |
| No compound | 10117 | 10153 | 100 | 100 | |
| #33890000X11020, 0.0004% | 2866 | 2790 | 28 | 27 | 72 |
| #33890000X11020, 0.002% | 543 | 520 | 5 | 5 | 95 |
| #33890000X11020, 0.01% | 202 | 218 | 2 | 2 | 98 |
| E-64, 1 nM | 9894 | 9604 | 98 | 95 | 4 |
| E-64, 10 nM | 5170 | 5444 | 51 | 54 | 48 |
| E-64, 100 nM | 958 | 960 | 9 | 9 | 91 |
| Blank | 10 | 7 | | | |

TABLE 35

| Condition | Net Signal (Fluorescence counts) | | Activity (%) | | Inhibition (%) |
|---|---|---|---|---|---|
| | Repeat 1 | Repeat 2 | Repeat 1 | Repeat 2 | |
| No compound | 9022 | 8921 | 101 | 99 | |
| D5, 0.0004% | 7844 | 8711 | 87 | 97 | 8 |
| D5, 0.002% | 7888 | 7297 | 88 | 81 | 15 |
| D5, 0.01% | 7040 | 7451 | 78 | 83 | 19 |
| D9, 0.0004% | 1377 | 1759 | 15 | 20 | 83 |
| D9, 0.002% | 447 | 446 | 5 | 5 | 95 |
| D9, 0.01% | 222 | 238 | 2 | 3 | 97 |
| D13, 0.0004% | 883 | 914 | 10 | 10 | 90 |
| D13, 0.002% | 271 | 314 | 3 | 3 | 97 |
| D13, 0.01% | 128 | 131 | 1 | 1 | 99 |
| D21, 0.0004% | 8732 | 8446 | 97 | 94 | 4 |
| D21, 0.002% | 7211 | 6789 | 80 | 76 | 22 |
| D21, 0.01% | 956 | 736 | 11 | 8 | 91 |
| E-64, 1 nM | 8864 | 8931 | 99 | 100 | 1 |

TABLE 35-continued

| Condition | Net Signal (Fluorescence counts) | | Activity (%) | | Inhibition (%) |
|---|---|---|---|---|---|
| | Repeat 1 | Repeat 2 | Repeat 1 | Repeat 2 | |
| E-64, 10 nM | 5727 | 5326 | 64 | 59 | 38 |
| E-64, 100 nM | 1009 | 1033 | 11 | 12 | 89 |
| Blank | 0 | 0 | | | |

TABLE 36

| Condition | Net Signal (Fluorescence counts) | | Activity (%) | | Inhibition (%) |
|---|---|---|---|---|---|
| | Repeat 1 | Repeat 2 | Repeat 1 | Repeat 2 | |
| No compound | 60213 | 59191 | 101 | 99 | 0 |
| DCH-TIC-0.5, 0.0004% | 37364 | 38895 | 63 | 65 | 36 |
| DCH-TIC-0.5, 0.002% | 13816 | 12919 | 23 | 22 | 78 |
| DCH-TIC-0.5, 0.01% | 1258 | 1445 | 2 | 2 | 98 |
| DCH-TIC-1.0, 0.0004% | 61364 | 58864 | 103 | 99 | 0 |
| DCH-TIC-1.0, 0.002% | 61972 | 62138 | 104 | 104 | 0 |
| DCH-TIC-1.0, 0.1% | 41515 | 43925 | 69 | 74 | 28 |
| E-64, 0.001 µM | 52418 | 49644 | 88 | 83 | 15 |
| E-64, 0.01 µM | 21262 | 19656 | 36 | 33 | 66 |
| E-64, 0.1 µM | 3091 | 3478 | 5 | 6 | 95 |
| Blank | 37 | 114 | | | |

CDK5:

In a further set of experiments, the inventor sought to determine whether the representative compositions and fractions thereof as well as a multivitamin mix had an effect on the enzymatic activities of recombinant human CDK5/p25 using an in vitro enzymatic assay.

Reagents used are shown in Tables 37-39 below and tested as stated unless indicated otherwise (Dinaciclib was used as reference compound). Here, the designations and ingredients of D5, D9, D13, and D21 are as noted above.

TABLE 37

| Compound I.D. | Compound Supplied | Stock Concentration | Dissolving Solvent | Test Range | Intermediate Dilution |
|---|---|---|---|---|---|
| HP Colors X11020 | Solution | 1% | 70% Ethanol | 0.01%, 0.002%, 0.0004% | Water |
| Dinaciclib | Solution | 10 mM | DMSO | 0.002 µM, 0.02 µM, 0.2 µM | 10% DMSO (aq) |

TABLE 38

| Compound I.D. | Compound Supplied | Stock Concentration | Dissolving Solvent | Test Range | Intermediate Dilution |
|---|---|---|---|---|---|
| DC-5 | Solution | 1% | 70% Ethanol | 0.01%, 0.002%, 0.0004% | Water |
| DC-9 | Solution | 1% | 70% Ethanol | 0.01%, 0.002%, 0.0004% | Water |
| DC-13 | Solution | 1% | 70% Ethanol | 0.01%, 0.002%, 0.0004% | Water |
| DC-21 | Solution | 1% | 70% Ethanol | 0.01%, 0.002%, 0.0004% | Water |

TABLE 38-continued

| Compound I.D. | Compound Supplied | Stock Concentration | Dissolving Solvent | Test Range | Intermediate Dilution |
|---|---|---|---|---|---|
| DCH-TIV 1.0 (Adult Centrum Multivitamin) | Solution | 1% | 70% Ethanol | 0.01%, 0.002%, 0.0004% | Water |
| Dinaciclib | Solution | 10 mM | DMSO | 0.002 μM, 0.02 μM, 0.2 μM | 10% DMSO (aq) |

TABLE 39

| Assay | Catalog # (Lot #) | Enzyme Used/ Reaction (ng) | Substrate |
|---|---|---|---|
| CDK5/p25 | 40105 (130618-2) | 10 | 0.1 mg/ml CDK Substrate Peptide 1 10 μM ATP |

Assay Conditions: The assay was performed using Kinase-Glo Plus luminescence kinase assay kit (Promega). It measures kinase activity by quantitating the amount of ATP remaining in solution following a kinase reaction. The luminescent signal from the assay is correlated with the amount of ATP present and is inversely correlated with the amount of kinase activity. The reference compound was diluted to 10% DMSO and 5 μl of the dilution was added to a 50 μl reaction so that the final concentration of DMSO is 1% in all of reactions. The test compound was diluted in water and 5 μl of the dilution was added to a 50 μl reaction. All of the enzymatic reactions were conducted at 30° C. for 45 minutes. The 50 μl reaction mixture contains 40 mM Tris, pH 7.4, 10 mM MgCl2, 0.1 mg/ml BSA, 1 mM DTT, 10 μM ATP, Kinase substrate and the enzyme. After the enzymatic reaction, 50 μl of Kinase-Glo Plus Luminescence kinase assay solution (Promega) was added to each reaction and incubated for 15 minutes, on the plate, at room temperature. Luminescence signal was measured using a BioTek Synergy 2 microplate reader.

Data Analysis: Kinase activity assays were performed in duplicate at each concentration. The luminescence data were analyzed using the computer software, Graphpad Prism. The difference between luminescence intensities in the absence of Kinase (Lut) and in the presence of Kinase (Luc) was defined as 100% activity (Lut–Luc). Using luminescence signal (Lu) in the presence of the compound, % activity was calculated as: % activity={(Lut–Lu)/(Lut–Luc)}×100%, where Lu=the luminescence intensity in the presence of the compound (all percent activities below zero were shown zero in the table).

Figure 13:
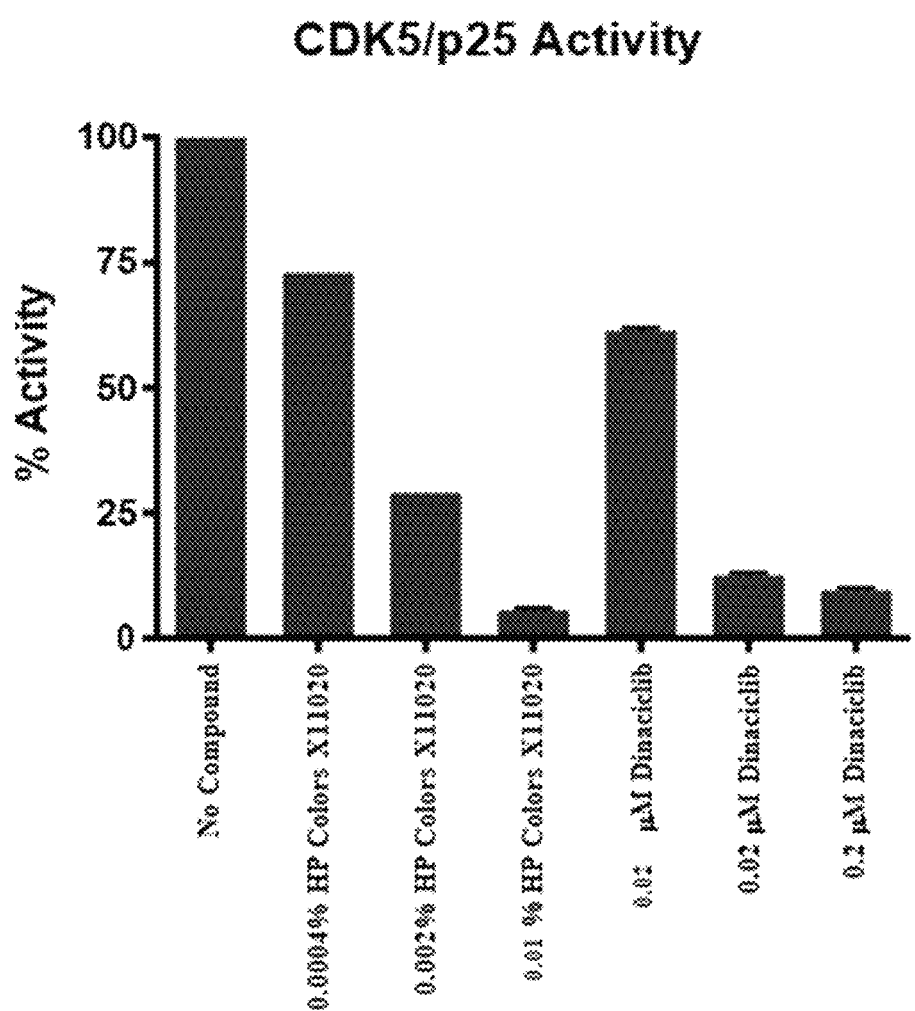
FIG. 13 is a graph depicting exemplary results for CDK5/p25 binding inhibition using a composition according to the inventive subject matter.
Figure 14:
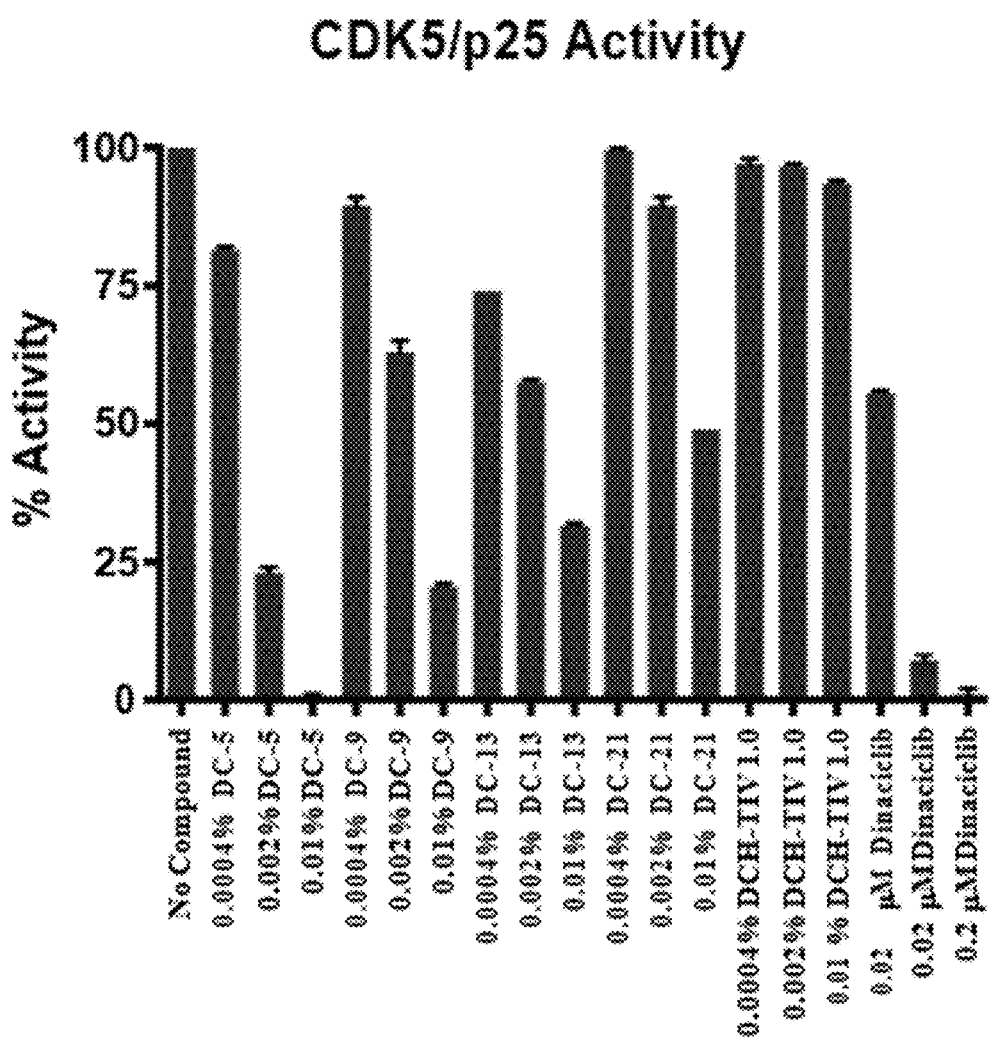
FIG. 14 is a graph depicting exemplary results for CDK5/p25 binding inhibition using various further compositions according to the inventive subject matter and a multivitamin composition.

The results for the above tests are shown in Tables 40-42, with Table 40 and FIG. 13 showing results for the representative composition, Table 41 and FIG. 14 showing results for the various colored fractions and the multivitamin mixture (here denoted as DCH-TIV 1.0). As can be readily taken from the data presented, the representative composition and the fractions thereof had significant inhibitory effect on CDK5, whereas the multivitamin mix had substantially no appreciable inhibitory effect as compared to the representative composition. Moreover, and at least at medium and low concentrations, the CDK5 inhibition had an at least moderate synergistic effect in the representative composition.

TABLE 40

| Compounds | Kinase Activity Luminescence | | % Activity | | % Inhibition |
|---|---|---|---|---|---|
| | Repeat1 | Repeat2 | Repeat1 | Repeat2 | |
| No Compound | 21499 | 21364 | 100 | 100 | |
| HP Colors X11020, 0.0004% | 26178 | 26281 | 73 | 73 | 27 |
| HP Colors X11020, 0.002% | 33942 | 33967 | 29 | 29 | 71 |
| HP Colors X11020, 0.01% | 38055 | 38177 | 6 | 5 | 94 |
| Dinaciclib, 0.002 μM | 28384 | 28205 | 61 | 62 | 39 |
| Dinaciclib, 0.02 μM | 36896 | 36850 | 12 | 13 | 87 |
| Dinaciclib, 0.2 μM | 37268 | 37490 | 10 | 9 | 90 |
| Background | 38991 | 39210 | | | |

TABLE 41

| Compounds | Kinase Activity Luminescence | | % Activity | | % Inhibition |
|---|---|---|---|---|---|
| | Repeat1 | Repeat2 | Repeat1 | Repeat2 | |
| No Compound | 20187 | 20295 | 100 | 100 | |
| 0.0004% DC-5 | 23997 | 23914 | 81 | 82 | 19 |
| 0.002% DC-5 | 35968 | 35411 | 22 | 24 | 77 |
| 0.01% DC-5 | 40138 | 40324 | 1 | 0 | 100 |
| 0.0004% DC-9 | 22139 | 22596 | 91 | 88 | 11 |
| 0.002% DC-9 | 27328 | 27981 | 65 | 61 | 37 |
| 0.01% DC-9 | 36274 | 36077 | 20 | 21 | 79 |
| 0.0004% DC-13 | 25412 | 25396 | 74 | 74 | 26 |
| 0.002% DC-13 | 28786 | 28580 | 57 | 58 | 42 |
| 0.01% DC-13 | 33831 | 33995 | 32 | 31 | 68 |
| 0.0004% DC-21 | 20168 | 20357 | 100 | 99 | 0 |
| 0.002% DC-21 | 22651 | 22070 | 88 | 91 | 11 |
| 0.01% DC-21 | 30462 | 30543 | 49 | 49 | 51 |
| 0.0004% DCH-TIV 1.0 | 20553 | 20979 | 98 | 96 | 3 |
| 0.002% DCH-TIV 1.0 | 20929 | 21076 | 97 | 96 | 4 |
| 0.01% DCH-TIV 1.0 | 21472 | 21736 | 94 | 93 | 7 |
| Dinaciclib, 0.002 μM | 29310 | 29124 | 55 | 56 | 45 |
| Dinaciclib, 0.02 μM | 38603 | 39041 | 8 | 6 | 93 |
| Dinaciclib, 0.2 μM | 40248 | 39973 | 0 | 2 | 99 |
| Background | 40474 | 40099 | | | |

IDO1/IDO2:

In a further set of experiments, the inventor sought to determine whether the representative compositions had an effect on the enzymatic activities of recombinant human IDO1 and/or IDO2 using an UV absorbance assay.

Reagents used are shown in Tables 42-43 below and tested as stated unless indicated otherwise.

TABLE 42

| Compound I.D. | Compound Supplied | Stock Concentration (mM) | Solvent | Test concentration | Intermediate Dilution |
|---|---|---|---|---|---|
| DailyColors Blend Lot #33890000X11020 | Liquid | 1% (w/v) | 70% EtOH | 0.01%, 0.002% 0.0004% | 20% DMSO |
| INCB024360* | Liquid | 0.05 | DMSO | 0.01, 0.1, 1, 10 μM | 20% DMSO |

TABLE 43

| Assay | Catalog # | Lot # | Enzyme concentration (nM) | Substrate |
|---|---|---|---|---|
| IDO1 | 71182 | 180305-B | 40 | L-Tryptophan (4 mM) |
| IDO2 | 71194 | 160519-C | 400 | L-Tryptophan (4 mM) |

Assay Conditions: The assay was performed measuring UV absorbance using recombinant IDO and L-Tryptophan as substrate. The UV absorbance at 321 nm is correlated with the amount of N-formylkynurenine, reaction product of IDO. The compounds (see 2.2) were diluted in 20% DMSO and 10 µl of the dilution was added to a 200 µl reaction so that the final concentration of DMSO was 1% in all reactions. All of the reactions were conducted at room temperature. The 200 µl reaction mixture in IDO Assay Buffer contained 400 nM IDO1 or IDO2, the indicated amount of the inhibitor, tryptophan, and the coupled reaction components. The reaction mixture incubated was for 180 min prior to reading the UV absorbance. For the negative control (blank), 10 µl of the assay buffer was added instead of the IDO enzyme. Absorbance was measured using a Tecan Infinite M1000 plate reader.

Data Analysis: The experiments were performed in duplicate at each concentration. The data were analyzed using the computer software GraphPad Prism. In the absence of the compound, the absorbance signal (At) in each data set was defined as 100% activity. In the absence of the IDO, the absorbance signal (Ab) in each data set was defined as 0% activity. The percent activity in the presence of each compound was calculated according to the following equation: % activity=[(A−Ab)/(At −Ab)]×100, where A=the absorbance signal in the presence of the compound. The percent inhibition was calculated according to the following equation: % inhibition=100−% activity.

Figure 15:
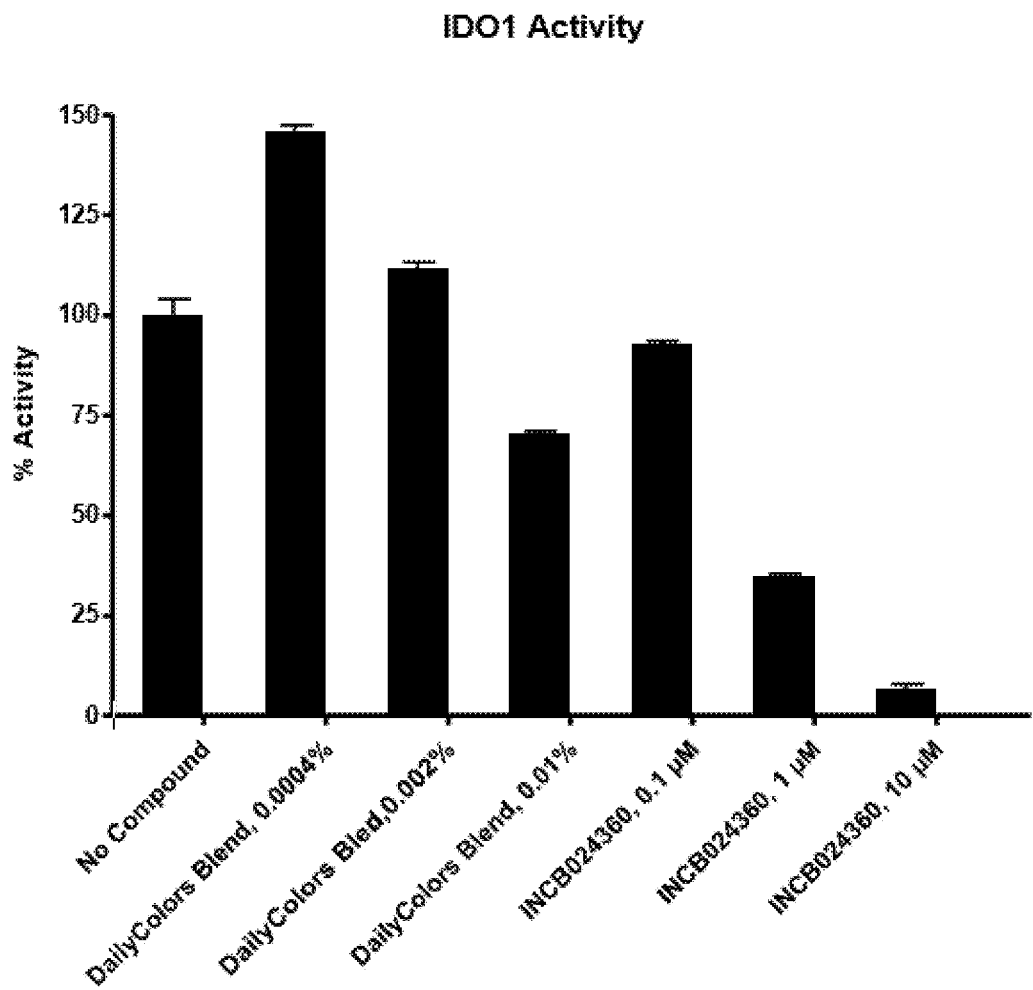
FIG. 15 is a graph depicting exemplary results for IDO1 inhibition using a composition according to the inventive subject matter.
Figure 16:
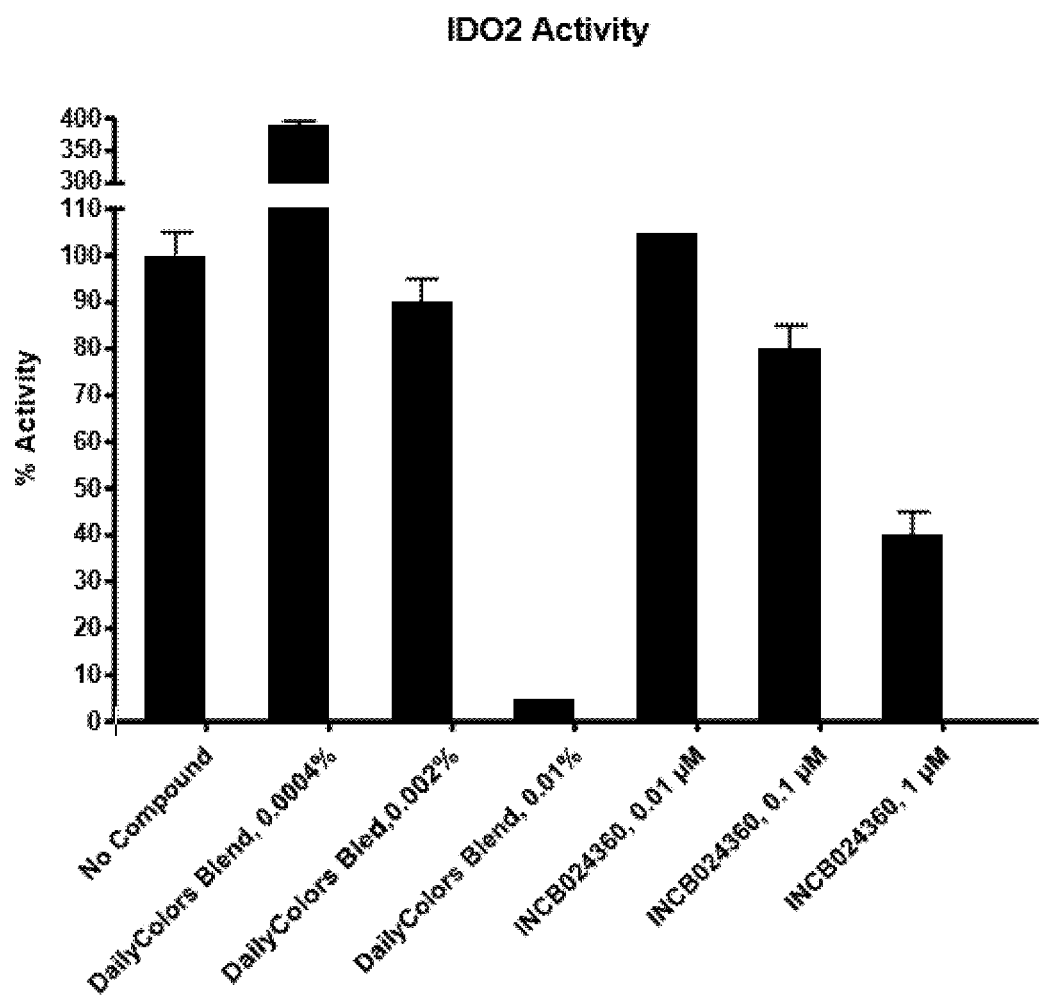
FIG. 16 is a graph depicting exemplary results for IDO2 inhibition using a composition according to the inventive subject matter.

The results for the above tests are shown in Tables 44-45, with Table 44 and FIG. 15 showing results for the representative composition on inhibition of IDO1, and Table 45 and FIG. 16 showing results for the representative composition on inhibition of IDO2. As can be readily taken from the data presented, the representative composition had inhibitory effect on IDO1 at higher concentrations and significant inhibitory effect on IDO2 at higher and moderate concentrations.

TABLE 44

| Compound I.D. | Absorbance (net) | | Activity (%) | | % Inhibition |
|---|---|---|---|---|---|
| | Repeat 1 | Repeat 2 | Repeat 1 | Repeat 2 | |
| No Compound | 0.82 | 0.76 | 104 | 96 | 0 |
| DailyColors Blend, 0.0004% | 1.13 | 1.15 | 145 | 147 | 0 |
| DailyColors Blend, 0.002% | 0.87 | 0.89 | 111 | 113 | 0 |
| DailyColors Blend, 0.01% | 0.57 | 0.56 | 71 | 70 | 30 |
| INCB024360, 0.1 µM | 0.73 | 0.74 | 92 | 93 | 7 |
| INCB024360, 1 µM | 0.29 | 0.30 | 34 | 36 | 65 |
| INCB024360, 10 µM | 0.07 | 0.09 | 5 | 8 | 93 |
| Blank | 0.03 | 0.03 | | | |

TABLE 45

| Compound I.D. | Absorbance (net) | | Activity (%) | | % Inhibition |
|---|---|---|---|---|---|
| | Repeat 1 | Repeat 2 | Repeat 1 | Repeat 2 | |
| No Compound | 0.17 | 0.16 | 105 | 95 | 0 |
| DailyColors Blend, 0.0004% | 0.46 | 0.45 | 395 | 385 | 0 |
| DailyColors Blend, 0.002% | 0.15 | 0.16 | 85 | 95 | 10 |
| DailyColors Blend, 0.01% | 0.07 | 0.07 | 5 | 5 | 95 |
| 1NCB024360, 0.01 µM | 0.17 | 0.17 | 105 | 105 | 0 |
| INCB024360, 0.1 µM | 0.14 | 0.15 | 75 | 85 | 20 |
| INCB024360, 1 µM | 0.10 | 0.11 | 35 | 45 | 60 |
| Blank | 0.06 | 0.07 | | | |

NAMPT:

In still another set of experiments, the inventor sought to determine whether the representative compositions had an effect on the enzymatic activities of recombinant human NAMPT using an in vitro enzymatic assay.

Reagents used are shown in Tables 46-47 below and tested as stated unless indicated otherwise.

TABLE 46

| Compound I.D. | Compound Supplied | Stock Concentration | Dissolving Solvent | Test Range |
|---|---|---|---|---|
| HP Color Blend lot # 33890000X11020 | Powder | 1% (w/v) | 70% EtOH | 0.0004%, 0.002%, and 0.01 % |
| FK-866* | Powder | 10 mM | DMSO | 0.001 µM, 0.01 µM, and 0.1 µM |

TABLE 47

| Assay | Catalog # | Enzyme Lot # | Enzyme Used (ng)/Reaction | Substrate |
|---|---|---|---|---|
| NAMPT | 91004 | 171009-2 | 100 | Nicotinamide 20 µM/ Phosphoribosyl pyrophosphate 40 µM |

Assay Conditions: The control compound is dissolved in DMSO. The dilution of the compounds was first performed in 100% DMSO with the highest concentration at 0.01 mM. Each intermediate compound dilution (in 100% DMSO) will then get directly diluted 10× fold into assay buffer for an intermediate dilution of 10% DMSO in assay buffer and 5 µl of the dilution was added to a 50 µl reaction so that the final concentration of DMSO is 1% in the reactions of the control compound and NAMPT only. For NAMPT, the compounds (see 2.2) were preincubated with NAMPT enzyme (see 2.3.1) in for 30 minutes. All of the enzymatic reactions were conducted in duplicate at 30° C. for 120 minutes by adding the substrate mixture containing in a 50 µl mixture containing 50 mM Tris-HCl, pH 8.0, 12.5 mM MgCl2, 20 µM nicotinamide, 40 µM PRPP, 20 µM ATP, 30 µg/mL of alcohol dehydrogenase, 10 µg/mL of NMNAT, 1.5% alcohol, 1 mM DTT, 0.02% BSA, 0.01% Tween 20. The final concentration of DMSO in all reactions was 1%. Fluorescence intensity was measured at an excitation of 340 nm and an emission of 460 nm using a Tecan Infinite M1000 microplate reader.

Data Analysis: NAMPT activity assays were performed in duplicates at each concentration. The fluorescent intensity data were analyzed using the computer software, GraphPad Prism. In the absence of the compound, the fluorescent intensity (Ft) in each data set was defined as 100% activity. In the absence of NAMPT, the fluorescent intensity (Fb) in each data set was defined as 0% activity. The percent activity in the presence of each compound was calculated according to the following equation: % activity=(F−Fb)/(Ft−Fb), where F=the fluorescent intensity in the presence of the compound. The values of percentage activity were plotted on a bar graph.

Figure 17:
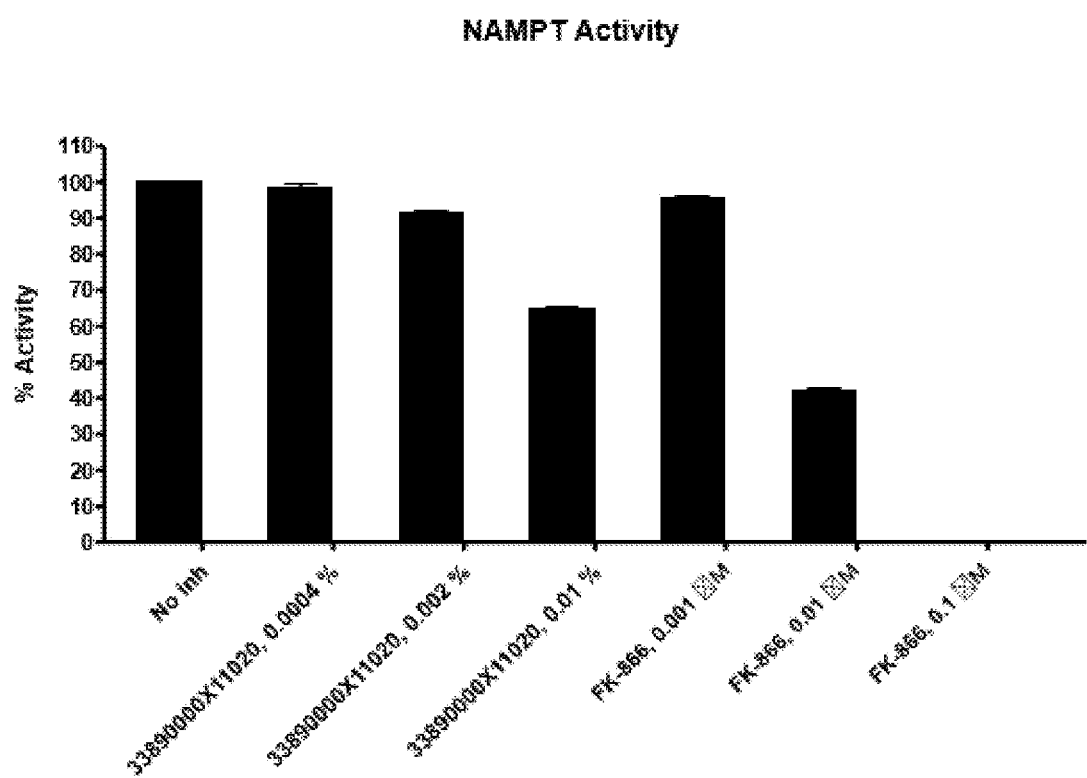
FIG. 17 is a graph depicting exemplary results for NAMPT inhibition using a composition according to the inventive subject matter.

Results for the above experiments are shown in Table 48 and FIG. 17. As will be readily appreciated, the representative composition had an inhibitory effect on NAMPT.

TABLE 48

| Compound | NAMPT Activity (Fluorescence Intensity) | | Background (Fluorescence count) | | % Activity | | |
|---|---|---|---|---|---|---|---|
| | Repeat 1 | Repeat 2 | Repeat 1 | Repeat 2 | Repeat 1 | Repeat 2 | % Inhibition |
| No Compound | 3507 | 3493 | 476 | 474 | 100 | 100 | 0 |
| 33890000X11020, 0.0004% | 3512 | 3494 | 508 | 516 | 99 | 99 | 1 |
| 33890000X11020, 0.002% | 3493 | 3515 | 737 | 715 | 91 | 92 | 8 |
| 33890000X11020, 0.01% | 3625 | 3633 | 1657 | 1646 | 65 | 65 | 35 |
| FK-866, 0.001 µM | 3328 | 3345 | 450 | 442 | 95 | 96 | 4 |
| FK-866, 0.01 µM | 1750 | 1766 | 454 | 461 | 42 | 43 | 57 |
| FK-866, 0.1 µM | 463 | 468 | 440 | 442 | 0 | 0 | 100 |
| Background | 452 | 460 | 438 | 442 | | | |

PCSK9:

In further experiments, the inventor sought to determine whether the representative compositions had an effect on binding of recombinant human PCSK9 and LDLR using an in vitro ELISA.

The reagents used are shown in Tables 49-50 below and tested as stated unless indicated otherwise (Anti-PCSK9 was used as a reference compound).

TABLE 49

| Sample | Form Supplied | Stock Conc. | Dissolving Solvent | Test Range |
|---|---|---|---|---|
| HP Color Blend lot#33890000X11020 | Powder | 1% (w/v) | 70% EtOH | 0.004, 0.02 and 0.1% |
| Anti-PCSK9* | Solution | 15 µM | DMSO | 0.1, 1 and 10 nM |

TABLE 50

| Assay | Catalog # | Lot # | Protein (ng/well) |
|---|---|---|---|
| PCSK9-Biotin | 71304 | 191212-1 | 100 |
| LDLR | 71205 | 190927-G | 50 |

Assay Conditions: 5 µl of sample or reference inhibitor was pre-incubated with 25 µl of 1×PCSK9 Assay Buffer in assay wells before starting the reaction by the addition of 20 µl of 2.5 ng/µl PCSK9-Biotin. Reaction was progressed for 2 hours at room temperature. Then, wells were washed three times with 1×PCSK9Assay Buffer and blocked with Blocking Buffer for 10 minutes. 100 µl of Streptavidin-HRP was added to all wells and incubated for 1 hour. Lastly, plate was emptied, washed three times and blocked before the addition of 100 µl of freshly prepared HRP chemiluminescent substrates to every well. Immediately, the luminescence of the samples was measured in a BioTek Synergy 2 microplate reader.

Data Analysis: Binding activity assays were performed in duplicates at each concentration. The luminescence signal was analyzed and compared. In the absence of the compound, the signal in each data set was defined as 100% (Ce) activity. In the absence of ligand (no LDLR), the signal in each data set was defined as 0% (C0) activity. The percent activity in the presence of each compound was calculated according to the following equation: % activity=(C−0)/(Ce−C0), where C=the intensity in the presence of the compound (all percent activities below zero were shown zero in the table). Compound fluorescence was removed by subtracting fluorescence at reaction time=0.

Figure 18:
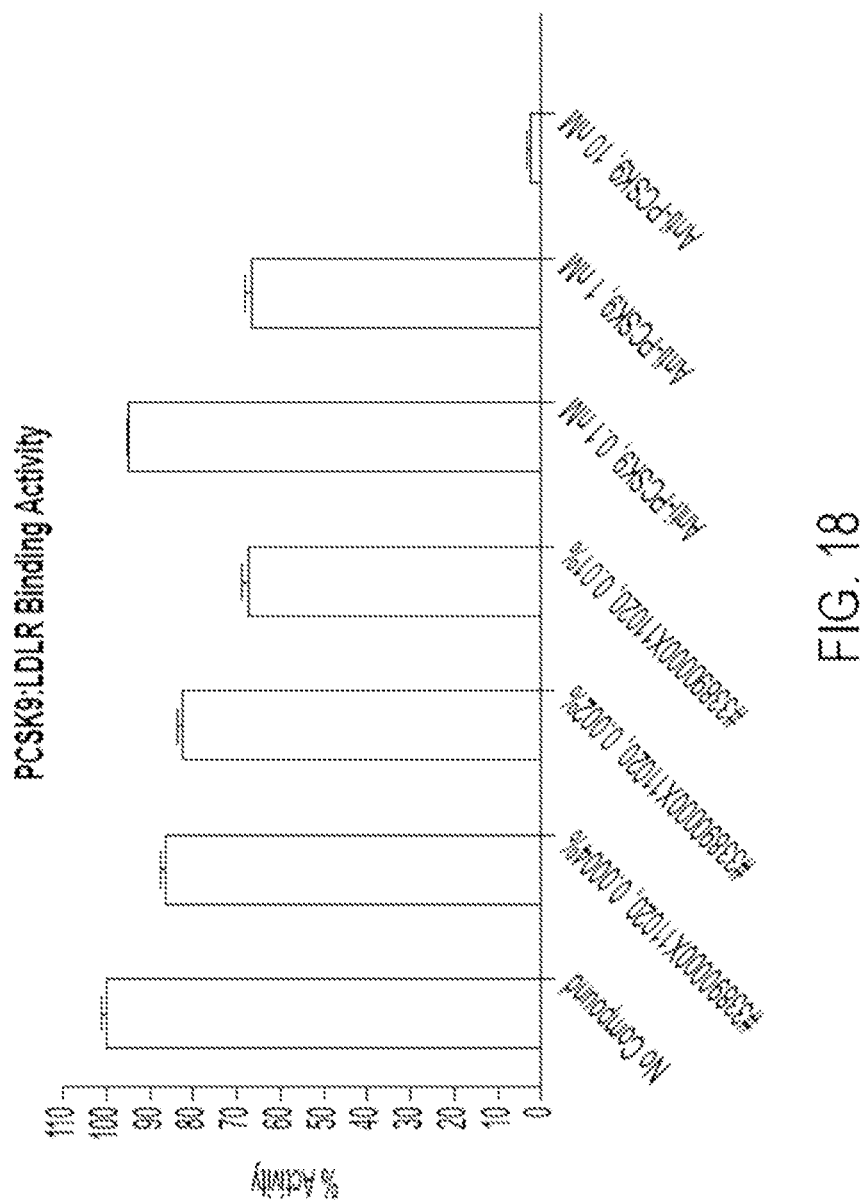
FIG. 18 is a graph depicting exemplary results for PCSK9:LDLR binding inhibition using a composition according to the inventive subject matter.

Results for the PCSK9 binding inhibition assay are shown in Table 51 and FIG. 18. As can be clearly seen form the data, the representative composition had significant inhibitory activity on binding of recombinant human PCSK9 and LDLR.

TABLE 51

| Condition | Signal (Luminescence counts) | | Activity (%) | | Inhibition (%) |
|---|---|---|---|---|---|
| | Repeat 1 | Repeat 2 | Repeat 1 | Repeat 2 | |
| No compound | 78139 | 77171 | 101 | 99 | |
| #33890000X11020, 0.0004% | 66611 | 67834 | 86 | 87 | 13 |
| #33890000X11020, 0.002% | 63124 | 64635 | 81 | 83 | 18 |
| #33890000X11020, 0.01% | 51675 | 53641 | 66 | 69 | 32 |
| Anti-PCSK9, 0.1 nM | 73367 | 73719 | 94 | 95 | 5 |
| Anti-PCSK9, 1 nM | 50528 | 52995 | 65 | 68 | 33 |
| Anti-PCSK9, 10 nM | 2614 | 2593 | 3 | 3 | 97 |
| Blank | 304 | 321 | | | |

CD47:

In additional experiments, the inventor further sought to determine whether the representative compositions had an effect on the binding activity of recombinant human CD47 (hCD47) with human SIRP-α (hSIRP-α) using an in vitro binding assay.

The reagents used are shown in Tables 52-53 below and tested as stated unless indicated otherwise (Anti-PCSK9 was used as a reference compound).

TABLE 52

| Compound I. D. | Compound Supplied | Stock Concentration | Test Range |
|---|---|---|---|
| DailyColors blend | Solution | 1% in 70% ethanol | 0.01, 0.002, 00004% |
| SIRP-α | Solution | 2.15 mg/ml | 0.05, 0.5, 5 µM |

TABLE 53

| Proteins | Catalog # (lot #) | Protein Reaction |
|---|---|---|
| hCD47, Fc fusion | 71177 (140429) | 100 ng |
| hSIRP-α, Biotin-labeled | 71138 (150604) | 600 ng |

Assay Conditions: CD47 was coated using 50 µL at 2 ng/µL at 4° C. overnight. After wash and block steps the test compounds were added to CD47-coated plate followed by addition of SIRP-α-biotin. Reaction was incubated for 2 h at room temperature. Binding was detected using HRP-conjugated Streptavidin.

Data Analysis: Binding assays were performed in duplicate at each concentration. The luminescence data were analyzed using the computer software, GraphPad Prism. Percent inhibition was determined by normalizing the data to signal from negative control wells (uncoated wells treated with the biotinylated ligand, set as 100% inhibition) and positive control wells (coated wells treated with the biotinylated ligand in the absence of any inhibitor, set as 0% inhibition).

Figure 19:
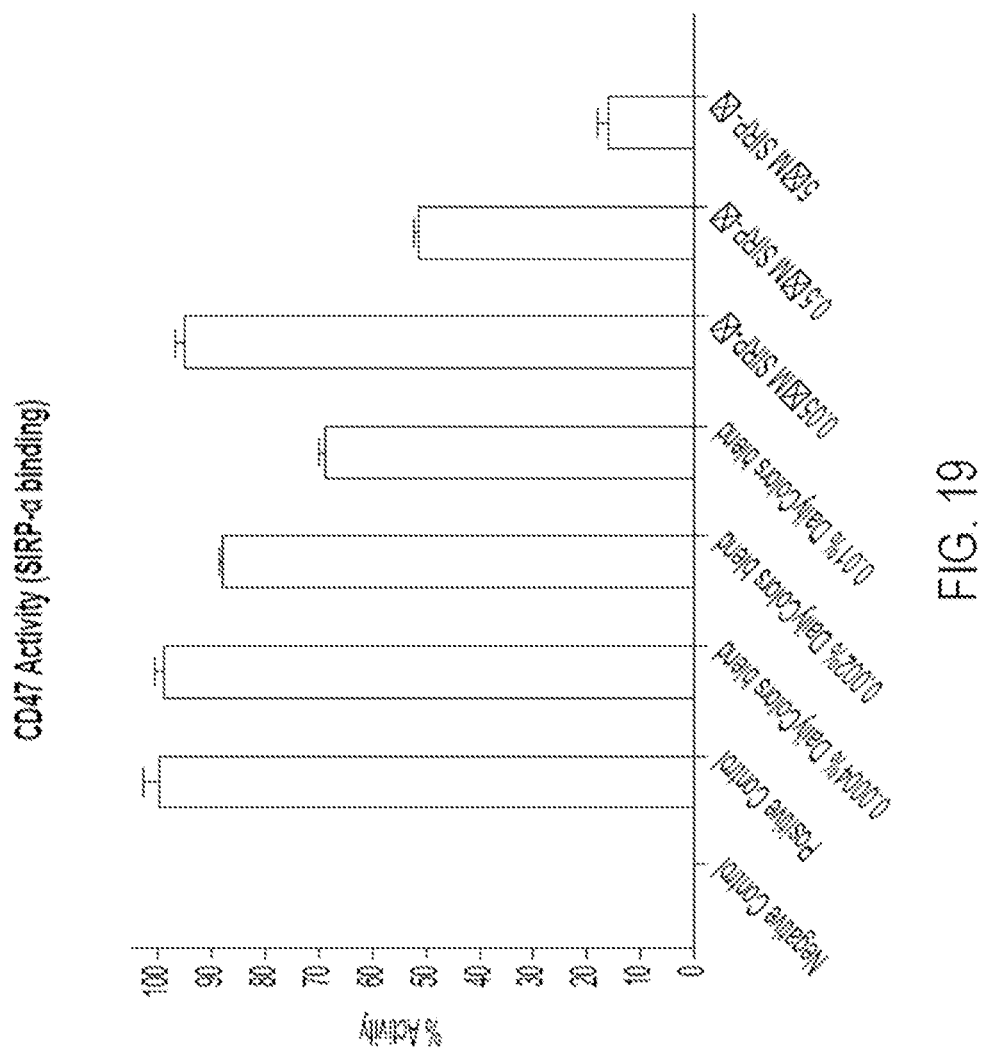
FIG. 19 is a graph depicting exemplary results for CD47 inhibition using a composition according to the inventive subject matter.

Results for the above experiment are listed in Table 54 and FIG. 19. Once more, it can be seen that the representative composition had significant inhibitory effect on the binding activity of recombinant human CD47 (hCD47) with human SIRP-α.

TABLE 54

| Compound | Luminescence | | Activity % | | Inhibition% |
|---|---|---|---|---|---|
| | Repeat 1 | Repeat 2 | Repeat 1 | Repeat 2 | |
| Negative Control | 92 | 94 | | | |
| Positive Control | 36937 | 38732 | 98 | 102 | 0 |
| 0.0004% DailyColors blend | 36685 | 38062 | 97 | 101 | 1 |
| 0.002% DailyColors blend | 33162 | 33355 | 88 | 88 | 12 |
| 0.01% DailyColors blend | 25830 | 26539 | 68 | 70 | 31 |
| 0.05 µM SIRP-α | 35347 | 36581 | 93 | 97 | 5 |
| 0.5 µM SIRP-α | 19746 | 19259 | 52 | 51 | 49 |
| 5 µM SIRP-α | 5310 | 6891 | 14 | 18 | 84 |

CD38:

In another set of experiments, the inventor sought to determine whether the representative compositions and fractions thereof as well as a multivitamin mix and other compounds known to affect NAD+ levels had an effect on the hydrolase enzymatic activity of recombinant human CD38 using an in vitro enzymatic assay.

Reagents used are shown in Tables 55-59 below and tested as stated unless indicated otherwise (*Apigenin was used as reference compound). Table 55 shows the representative composition, while Table 56 shows the colored fractions and multivitamin mix. Here, DC-5=Yellow Blend, DC-9=Purple Blend, DC-21-Green Blend, DC-13=Red Blend DCH-TIV 1.0 (Adult Centrum Multivitamins). The red blend included Apple Extract, Pomegranate Extract, Tomato Powder, Beet; the green blend included Olive Extract, Rosemary Extract, Green Coffee Bean Extract, Kale; the orange/yellow blend included Onion Extract, Ginger Extract, Grapefruit Extract, Carrot; and the purple/blue blend included Grape, Blueberry Extract, Currant, and Elderberry as listed above. Table 57 shows two compounds known to influence NAD+ levels: Commercially available "Elysium Health NAD" and "TrueNiagen", both containing nicotinamide riboside, while Table 58 shows the representative composition (DCH-TIV-0.5) and a multivitamin composition (DCH-TIV-1.0 (Adult Centrum Multivitamin)). Table 59 shows the enzyme and substrate used in this set of experiments.

TABLE 55

| Sample | Form Supplied | Stock Conc. | Dissolving Solvent | Test Range |
|---|---|---|---|---|
| HP Color Blend lot#33890000X11020 | Powder | 1% (w/v) | 70% EtOH | 0.004, 0.02 and 0.1% |
| Apigenin | Solution | 50 mM | DMSO | 1, 10 and 100 µM |

TABLE 56

| Sample | Form Supplied | Stock Conc. | Dissolving Solvent | Test Range |
|---|---|---|---|---|
| D5 | Powder | 1% (w/v) | 70% EtOH | 0.0004, 0.002 and 0.01% |
| D9 | Powder | 1% (w/v) | 70% EtOH | 0.0004, 0.002 and 0.01% |
| D13 | Powder | 1% (w/v) | 70% EtOH | 0.0004, 0.002 and 0.01% |
| D21 | Powder | 1% (w/v) | 70% EtOH | 0.0004, 0.002 and 0.01% |
| Apigenin | Solution | 50 mM | DMSO | 1, 10 and 100 µM |

TABLE 57

| Sample | Form Supplied | Stock Conc. | Dissolving Solvent | Test Range |
|---|---|---|---|---|
| DCH-ELY-1.0 (Elysium Health NAD) | Powder | 1% (w/y) | 70% EtOH | 0.0004, 0.002 and 0.01% |
| DCH-TN-1.0 (TruNiagen; nicotinamide riboside) | Powder | 1% (w/y) | 70% EtOH | 0.0004, 0.002 and 0.01% |
| Apigenin | Solution | 50 mM | DMSO | 1, 10 and 100 µM |

TABLE 58

| Sample | Form Supplied | Stock Conc. | Dissolving Solvent | Test Range |
|---|---|---|---|---|
| DCH-TIV-0.5 | Powder | 1% (w/v) | 70% EtOH | 0.004, 0.02 and 0.1% |
| DCH-TIV-1.0 (Adult Centrum Multivitamin) | Powder | 1% (w/v) | 70% EtOH | 0.004, 0.02 and 0.1% |
| Apigenin | Solution | 50 mM | DMSO | 1, 10 and 100 µM |

TABLE 59

| Assay | Catalog # | Enzyme Lot # | Enzyme Used (ng)/Reaction | Substrate |
|---|---|---|---|---|
| CD38 | 71277 | 170801-1 | 20 | 10 µM ε-NAD |

Assay Conditions: 10 µl of the sample or reference inhibitor was added to 20 µl of enzyme solution and pre-incubated for 30 minutes. The enzymatic reactions were started by the addition of 20 µl of the substrate ε-NAD+, for a total reaction volume of 50 µl. Reaction time was 10 minutes, and then fluorescence intensity at an excitation of 300 nm and an emission of 410 nm was read using a Tecan Infinite M1000 microplate reader.

Data Analysis: Enzyme activity assays were performed in duplicates at each concentration. The fluorescence intensity data were analyzed and compared. In the absence of the compound, the intensity in each data set was defined as 100% (Ce) activity. In the absence of enzyme, the intensity in each data set was defined as 0% (C0) activity. The percent activity in the presence of each compound was calculated according to the following equation: % activity=(C−C0)/(Ce−C0), where C=the intensity in the presence of the compound (all percent activities below zero were shown zero in the table). Compound fluorescence was removed by subtracting fluorescence at reaction time=0.

Figure 20:
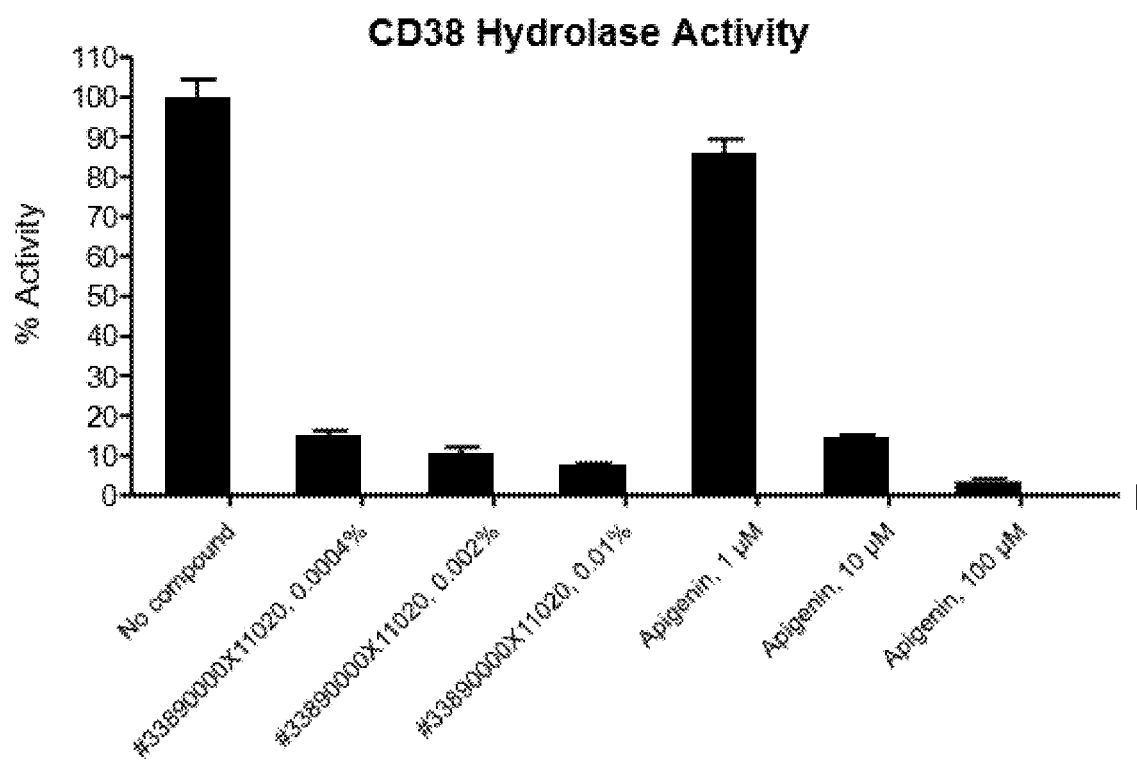
FIG. 20 is a graph depicting exemplary results for CD38 inhibition using a composition according to the inventive subject matter.
Figure 21:
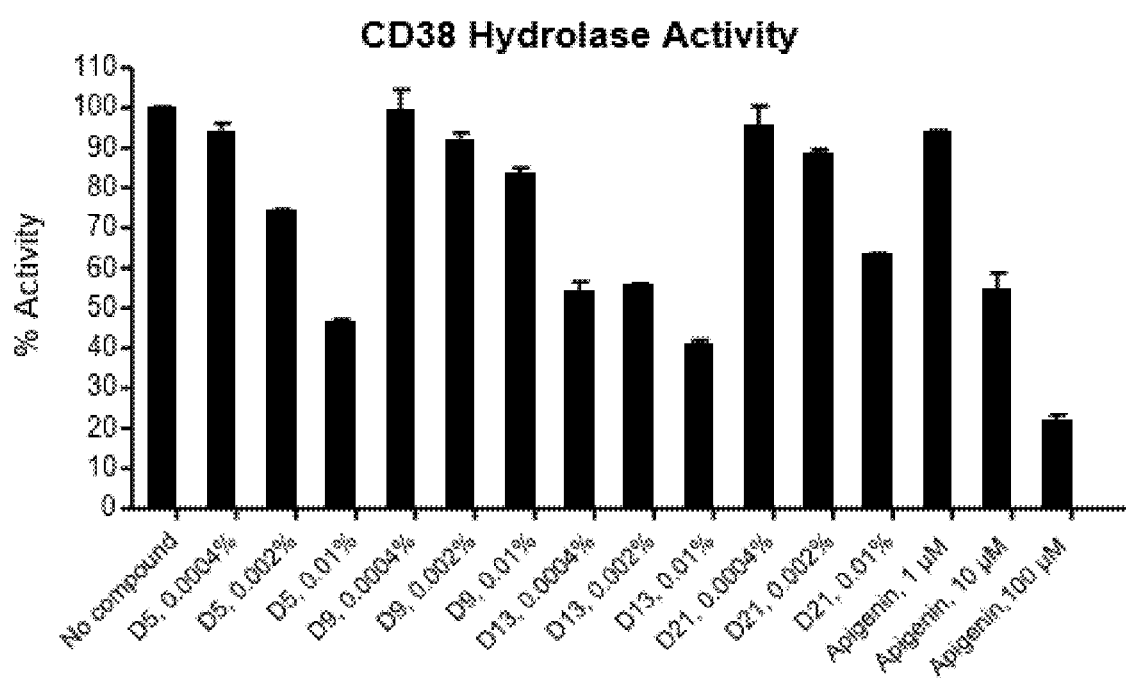
FIG. 21 is a graph depicting exemplary results for CD38 inhibition using further compositions according to the inventive subject matter.

The results for the above substrates are shown in Tables 60-63 and FIGS. 20-23. More specifically, Table 60 and FIG. 20 show the results where the representative composition was used for inhibition of CD38. As can be readily seen from the data, the representative composition exhibited remarkably strong inhibition. Table 61 and FIG. 21 show the results where the colored fractions of the representative composition was used for inhibition of CD38. Notably, here as well a strong inhibition was observed. Moreover, it should be noted that the colored fractions in the representative composition provided a strong synergistic effect with respect to CD38 inhibition.

Figure 22:
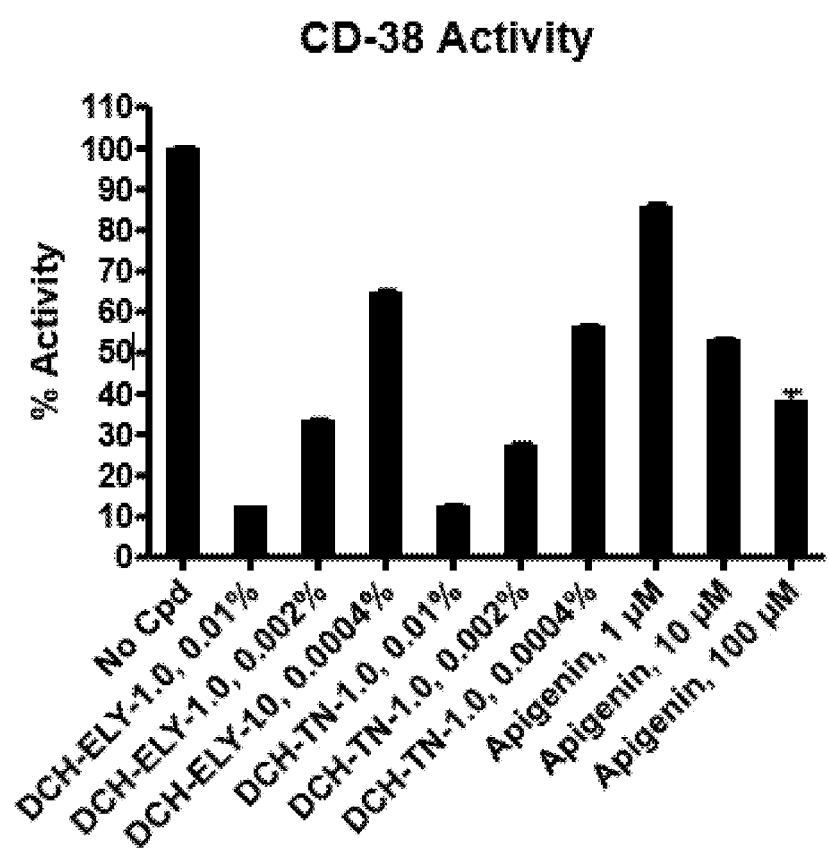
FIG. 22 is a graph depicting exemplary results for CD38 inhibition using known compositions containing nicotinamide riboside.
Figure 23:
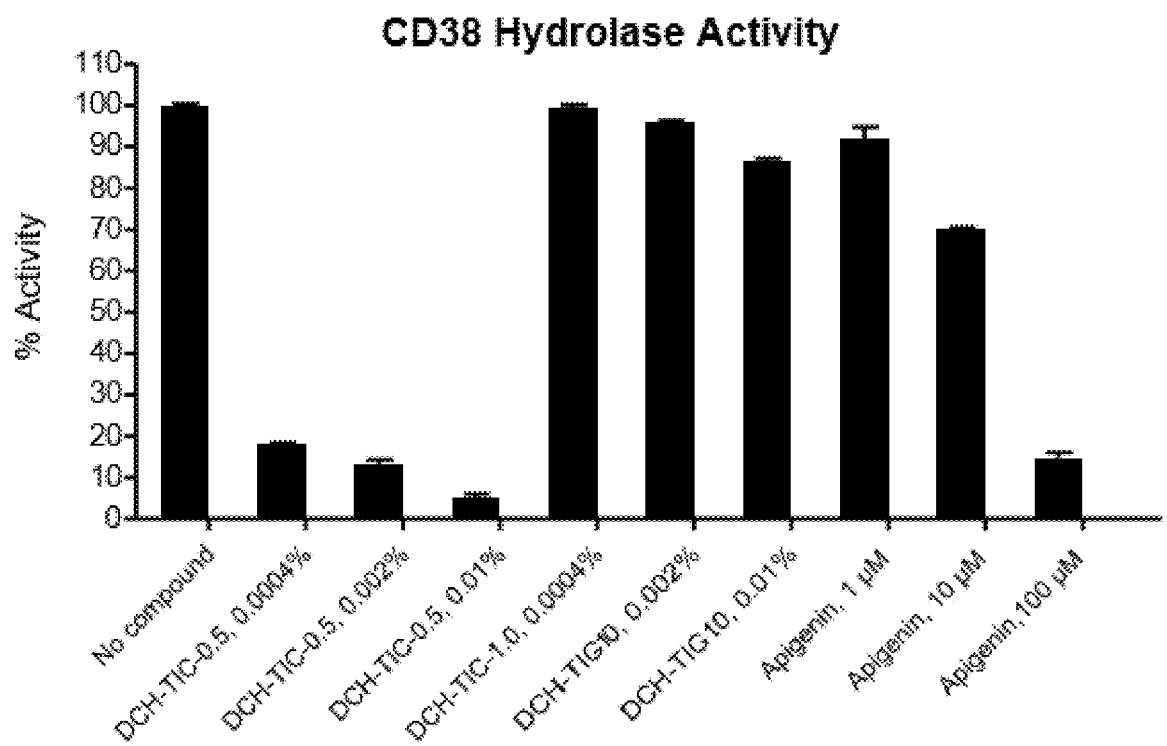
FIG. 23 is a graph depicting exemplary results for CD38 inhibition using a composition according to the inventive subject matter and a known multivitamin composition.

Table 62 and FIG. 22 show the results for corresponding experiments where the where the "Elysium Health NAD" and "TrueNiagen" (both containing nicotinamide riboside) were used for inhibition of CD38. Here, both formulations showed inhibition of CD38, however, not to the same extent as for the representative composition. In contrast, Table 63 and FIG. 23 show the results for corresponding experiments where a multivitamin composition was used to inhibit CD38. Here, a direct comparison is shown between the representative composition (DCH-TIV-0.5) and the multivitamin composition (DCH-TIV-1.0 in Table 63, DCH-TIG-1.0 in FIG. 23).

TABLE 60

| Condition | Net Signal (Fluorescence counts) | | Activity (%) | | Inhibition (%) |
|---|---|---|---|---|---|
| | Repeat 1 | Repeat 2 | Repeat 1 | Repeat 2 | |
| No compound | 4393 | 4027 | 104 | 96 | |
| #33890000X11020, 0.0004% | 603 | 694 | 14 | 16 | 85 |
| #33890000X11020, 0.002% | 411 | 516 | 10 | 12 | 89 |
| #33890000X11020, 0.01% | 346 | 311 | 8 | 7 | 92 |
| Apigenin, 1 µM | 3461 | 3761 | 82 | 89 | 14 |
| Apigenin, 10 µM | 647 | 618 | 15 | 14 | 85 |
| Apigenin, 100 µM | 185 | 135 | 4 | 3 | 96 |
| Blank | 3 | 19 | 0 | 0 | |

TABLE 61

| Condition | Net Signal (Fluorescence counts) | | Activity (%) | | Inhibition (%) |
|---|---|---|---|---|---|
| | Repeat 1 | Repeat 2 | Repeat 1 | Repeat 2 | |
| No compound | 9204 | 9171 | 100 | 100 | |
| D5, 0.0004% | 8528 | 8830 | 93 | 96 | 6 |
| D5, 0.002% | 6850 | 6811 | 74 | 74 | 26 |
| D5, 0.01% | 4253 | 4353 | 46 | 47 | 53 |
| D9, 0.0004% | 8679 | 9582 | 94 | 104 | 1 |
| D9, 0.002% | 8327 | 8618 | 91 | 94 | 8 |
| D9, 0.01% | 7801 | 7614 | 85 | 83 | 16 |
| D13, 0.0004% | 4811 | 5203 | 52 | 57 | 46 |
| D13, 0.002% | 5168 | 5154 | 56 | 56 | 44 |
| D13, 0.01% | 3876 | 3771 | 42 | 41 | 59 |
| D21, 0.0004% | 8340 | 9222 | 91 | 100 | 4 |
| D21, 0.002% | 8122 | 8226 | 88 | 90 | 11 |
| D21, 0.01% | 5853 | 5812 | 64 | 63 | 37 |
| Apigenin, 1 µM | 8650 | 8614 | 94 | 94 | 6 |

TABLE 61-continued

| Condition | Net Signal (Fluorescence counts) | | Activity (%) | | Inhibition (%) |
|---|---|---|---|---|---|
| | Repeat 1 | Repeat 2 | Repeat 1 | Repeat 2 | |
| Apigenin, 10 µM | 4670 | 5416 | 51 | 59 | 45 |
| Apigenin, 100 µM | 1979 | 2165 | 21 | 23 | 78 |
| Blank | 29 | 25 | | | |

TABLE 62

| Condition | Net Signal (Fluorescence counts) | | Activity (%) | | Inhibition (%) |
|---|---|---|---|---|---|
| | Repeat 1 | Repeat 2 | Repeat 1 | Repeat 2 | |
| No compound | 13504 | 13458 | 100 | 100 | 0 |
| DCH-ELY-1.0, 0.01% | 1736 | 1733 | 13 | 13 | 87 |
| DCH-ELY-1.0, 0.002% | 4571 | 4564 | 34 | 34 | 66 |
| DCH-ELY-1.0, 0.0004% | 8806 | 8767 | 65 | 65 | 35 |
| DCH-TN-1.0, 0.01% | 1742 | 1722 | 13 | 13 | 87 |
| DCH-TN-1.0, 0.002% | 3776 | 3716 | 28 | 27 | 72 |
| DCH-TN-1.0, 0.0004% | 7650 | 7587 | 57 | 56 | 44 |
| Apigenin, 1 µM | 11531 | 11647 | 86 | 86 | 14 |
| Apigenin, 10 µM | 7118 | 7228 | 53 | 54 | 47 |
| Apigenin, 100 µM | 5012 | 5473 | 37 | 40 | 61 |
| Blank | 30 | 29 | | | |

TABLE 63

| Condition | Net Signal (Fluorescence counts) | | Activity (%) | | Inhibition (%) |
|---|---|---|---|---|---|
| | Repeat 1 | Repeat 2 | Repeat 1 | Repeat 2 | |
| No compound | 4383 | 4355 | 100 | 100 | 0 |
| DCH-TIV-0.5, 0.0004% | 838 | 810 | 18 | 18 | 82 |
| DCH-TIV-0.5, 0.002% | 653 | 541 | 14 | 12 | 87 |
| DCH-TIV-0.5, 0.01% | 240 | 296 | 5 | 6 | 95 |
| DCH-TIV-1.0, 0.0004% | 4371 | 4320 | 100 | 99 | 1 |
| DCH-TIV-1.0, 0.002% | 4168 | 4209 | 95 | 96 | 4 |
| DCH-TIV-1.0, 0.01% | 3812 | 3744 | 87 | 86 | 14 |
| Apigenin, 1 µM | 4138 | 3883 | 95 | 89 | 8 |
| Apigenin, 10 µM | 3091 | 3057 | 70 | 70 | 30 |
| Apigenin, 100 µM | 632 | 728 | 14 | 16 | 85 |
| Blank | 52 | 23 | | | |

JAK1/JAK2/JAK3:

In further experiments, the inventor sought to determine whether the representative compositions and fractions thereof had an effect on the enzymatic activities of the recombinant human kinases JAK1, JAK2, and JAK3 using an in vitro enzymatic assay.

Reagents used are shown in Tables 64-66 below and tested as stated unless indicated otherwise (*Apigenin was used as reference compound). Table 64 shows the representative composition, while Table 65 shows the colored fractions. Here, DC-5=Yellow Blend, DC-9=Purple Blend, DC-21-Green Blend, DC-13=Red Blend. The red blend included Apple Extract, Pomegranate Extract, Tomato Powder, Beet; the green blend included Olive Extract, Rosemary Extract, Green Coffee Bean Extract, Kale; the orange/yellow blend included Onion Extract, Ginger Extract, Grapefruit Extract, Carrot; and the purple/blue blend included Grape, Blueberry Extract, Currant, and Elderberry as listed above. Staurosporine was used as a reference compound. Table 66 lists the enzymes and substrates used in the assays.

TABLE 64

| Compound I.D. | Compound Supplied | Stock Concentration | Dissolving Solvent | Test Range | Intermediate Dilution |
|---|---|---|---|---|---|
| DailyColors Blend Lot #33890000X11020 | solution | 1% (w/v) | 70% EtOH | 0.01%, 0.002%, 0.0004% | Water |
| Staurosporine | solution | 1 mM | DMSO | 0.001 µM, 0.01 µM, 0.1 µM | 10 % DMSO (aq) |

TABLE 65

| Compound I.D. | Compound Supplied | Stock Concentration | Dissolving Solvent | Test Range | Intermediate Dilution |
|---|---|---|---|---|---|
| DC-5 | solution | 1% (w/v) | 70% EtOH | 0.01%, 0.002%, 0.0004% | Water |
| DC-9 | solution | 1% (w/v) | 70% EtOH | 0.01%, 0.002%, 0.0004% | Water |
| DC-13 | solution | 1% (w/v) | 70% EtOH | 0.01%, 0.002%, 0.0004% | Water |
| DC-21 | solution | 1% (w/v) | 70% EtOH | 0.01%, 0.002%, 0.0004% | Water |
| Staurosporine | solution | 1 mM | DMSO | 30 nM-3 µM | 10 % DMSO (aq) |

TABLE 66

| Assay | Catalog # (Lot #) | Enzyme Used (ng)/Reaction | Substrate |
|---|---|---|---|
| Jak 1 | 40449 (190919-3) | 100 | 0.1 mg/ml, IRS1-tide/ 10 µM ATP |
| Jak 2 | 40450 (190603-G) | 50 | 0.2 mg/ml Poly (Glu, Tyr)/ 10 µM ATP |
| Jak 3 | 40452 (150921-B2) | 10 | 0.2 mg/ml Poly (Glu, Tyr)/ 10 µM ATP |

Assay Conditions: The assay was performed using Kinase-Glo Plus luminescence kinase assay kit (Promega). It measures kinase activity by quantitating the amount of ATP remaining in solution following a kinase reaction. The luminescent signal from the assay is correlated with the amount of ATP present and is inversely correlated with the amount of kinase activity. The reference compound was diluted as noted. The compound was diluted in water and 5 µl of the dilution was added to a 50 µl reaction. All of the enzymatic reactions were conducted at 30° C. for 45 minutes. The 50 µl reaction mixture contains 40 mM Tris, pH 7.4, 10 mM MgCl2, 0.1 mg/ml BSA, 1 mM DTT, 10 µM ATP, Kinase substrate and the respective enzyme. After the enzymatic reaction, 50 µl of Kinase-Glo Plus Luminescence kinase assay solution (Promega) was added to each reaction and incubate the plate for 15 minutes at room temperature. Luminescence signal was measured using a BioTek Synergy 2 microplate reader.

Data Analysis: Kinase activity assays were performed in duplicate at each concentration. The luminescence data were analyzed using the computer software, GraphPad Prism. The difference between luminescence intensities in the absence of Kinase (Lut) and in the presence of Kinase (Luc) was defined as 100% activity (Lut−Luc). Using luminescence signal (Lu) in the presence of the compound, % activity was calculated as: % activity={(Lut−Lu)/(Lut−Luc)}×100%, where Lu=the luminescence intensity in the presence of the compound (all percent activities below zero were shown zero in the table).

Figure 24:
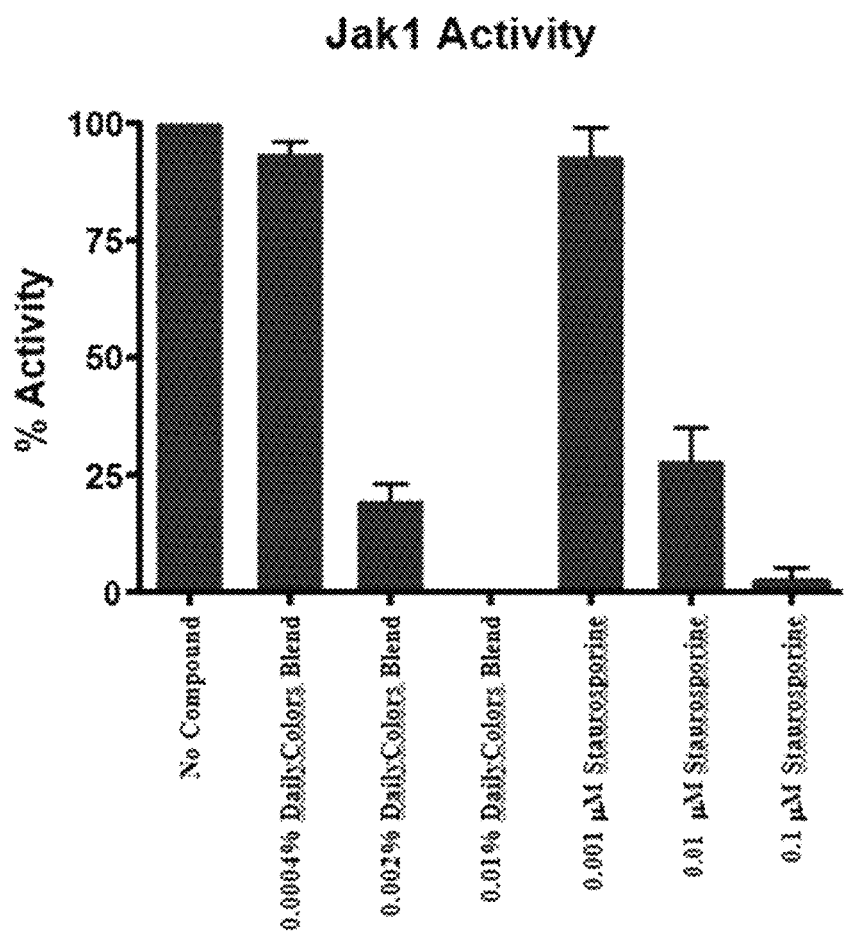
FIG. 24 is a graph depicting exemplary results for JAK1 inhibition using a composition according to the inventive subject matter.
Figure 25:
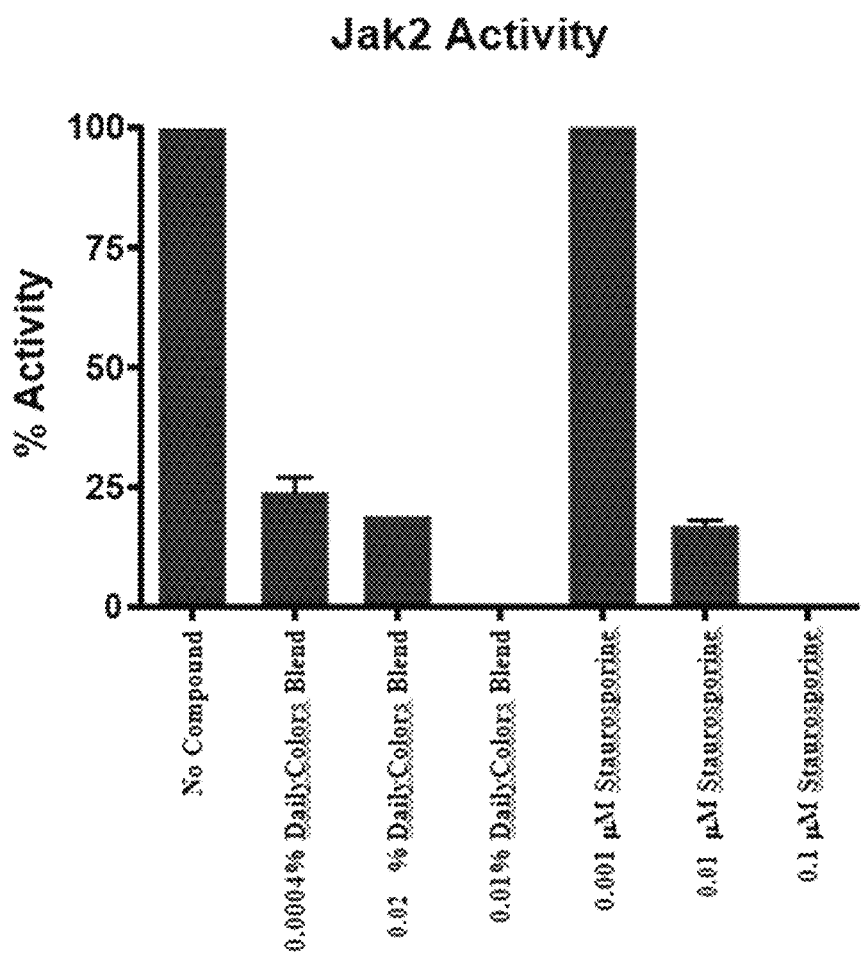
FIG. 25 is a graph depicting exemplary results for JAK2 inhibition using a composition according to the inventive subject matter.
Figure 26:
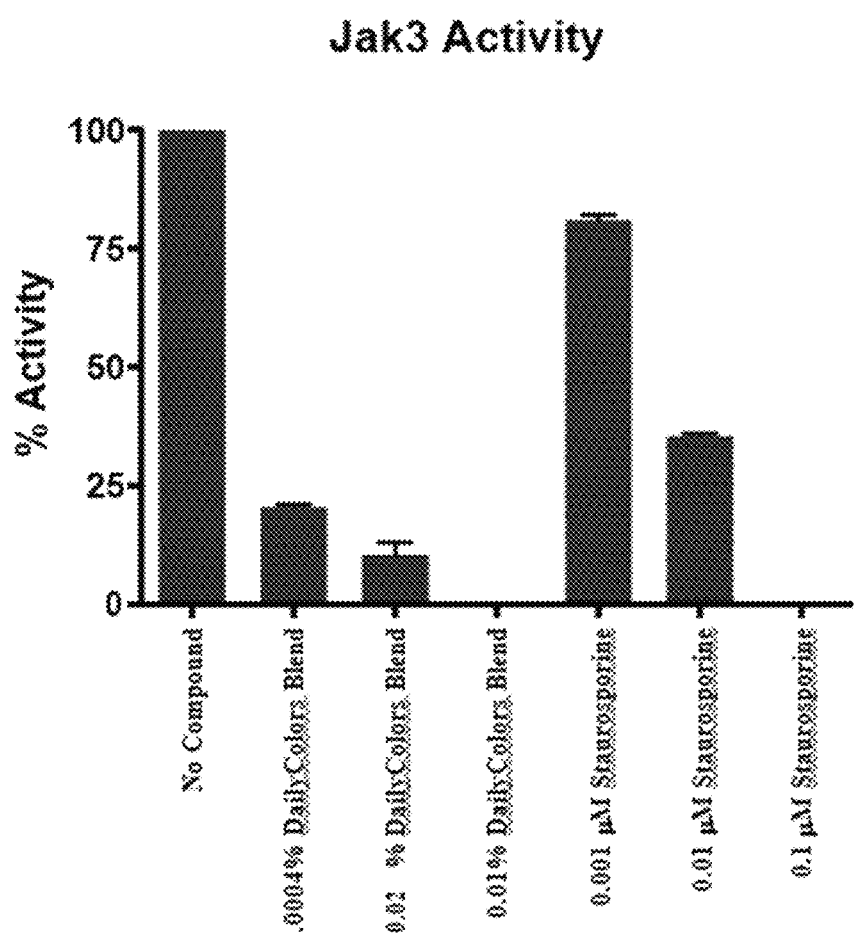
FIG. 26 is a graph depicting exemplary results for JAK3 inhibition using a composition according to the inventive subject matter.

The results for inhibition using the representative composition are shown in Tables 67-69 and FIGS. 24-26. Table 67 and FIG. 24 show results for JAK1 inhibition using the representative composition. Table 68 and FIG. 25 show results for JAK2 inhibition using the representative composition. Table 69 and FIG. 26 show results for JAK3 inhibition using the representative composition. As can be readily taken from these results, the inhibition of all three tested JAK kinases was significant and substantial, matching or exceeding the inhibition provided by the reference compound.

TABLE 67

| Compounds | Kinase Activity Luminescence | | % Activity | | % Inhibition |
|---|---|---|---|---|---|
| | Repeat1 | Repeat2 | Repeat1 | Repeat2 | |
| No Compound | 24012 | 26135 | 107 | 93 | |
| 0.0004% DailyColors Blend | 25706 | 26483 | 96 | 91 | 6 |
| 0.002% DailyColors Blend | 37313 | 38359 | 23 | 16 | 81 |
| 0.01% DailyColors Blend | 42256 | 42457 | 0 | 0 | 100 |
| 0.001 µM Staurosporine | 25176 | 27054 | 99 | 87 | 7 |
| 0.01 µM Staurosporine | 37642 | 35358 | 21 | 35 | 72 |
| 0.1 µM Staurosporine | 40161 | 40781 | 5 | 1 | 97 |
| Background | 40868 | 40953 | | | |

TABLE 68

| Compounds | Kinase Activity Luminescence | | % Activity | | % Inhibition |
|---|---|---|---|---|---|
| | Repeat1 | Repeat2 | Repeat1 | Repeat2 | |
| No Compound | 20027 | 20151 | 100 | 100 | |
| 0.0004% DailyColors Blend | 35932 | 34651 | 21 | 27 | 76 |
| 0.002% DailyColors Blend | 36319 | 36342 | 19 | 19 | 81 |
| 0.01% DailyColors Blend | 41665 | 40587 | 0 | 0 | 100 |
| 0.001 µM Staurosporine | 19100 | 20922 | 105 | 96 | 0 |
| 0.01 µM Staurosporine | 36988 | 36554 | 16 | 18 | 83 |
| 0.1 µM Staurosporine | 42700 | 40639 | 0 | 0 | 100 |
| Background | 40021 | 40218 | | | |

TABLE 69

| Compounds | Kinase Activity Luminescence | | % Activity | | % Inhibition |
|---|---|---|---|---|---|
| | Repeat1 | Repeat2 | Repeat1 | Repeat2 | |
| No Compound | 18990 | 20947 | 100 | 95 | |
| 0.0004% DailyColors Blend | 35140 | 35074 | 20 | 21 | 79 |
| 0.002% DailyColors Blend | 36502 | 37407 | 13 | 8 | 89 |
| 0.01% DailyColors Blend | 39437 | 41388 | 0 | 0 | 100 |
| 0.001 µM Staurosporine | 23814 | 23348 | 80 | 82 | 19 |
| 0.01 µM Staurosporine | 32137 | 32417 | 36 | 35 | 65 |
| 0.1 µM Staurosporine | 39970 | 40121 | 0 | 0 | 100 |
| Background | 38815 | 39237 | | | |

Figure 27:
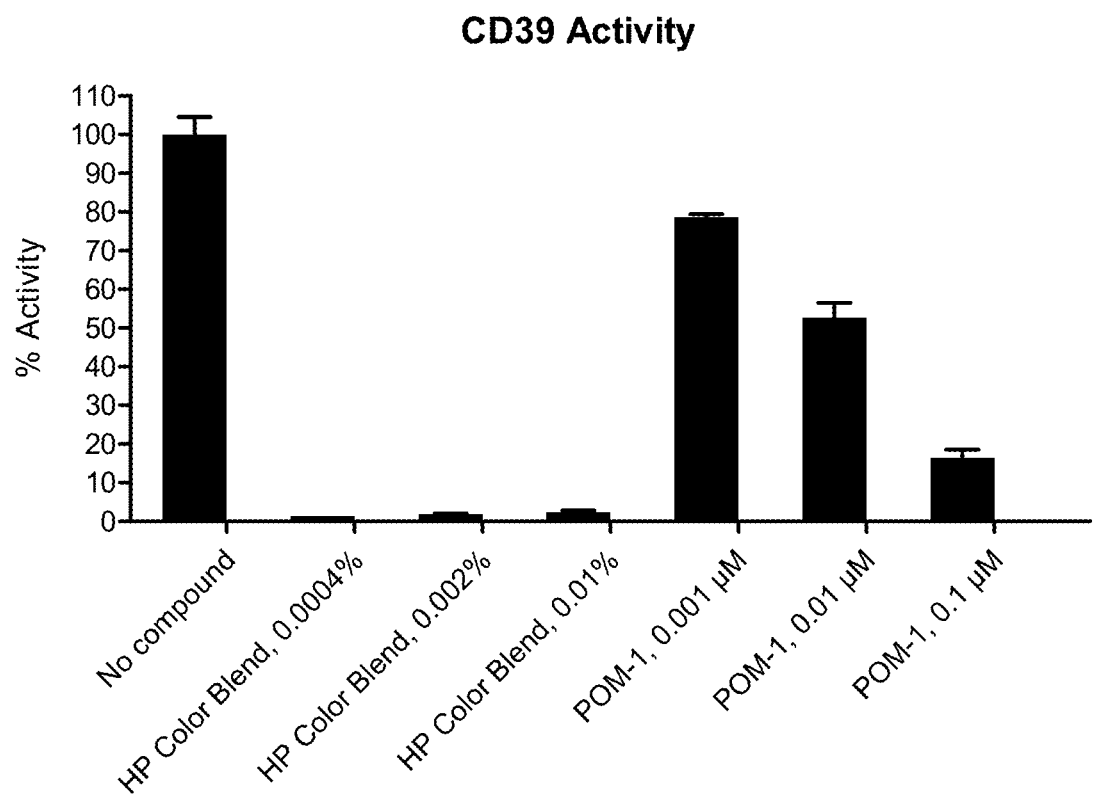
FIG. 27 is a graph depicting exemplary results for CD39 inhibition using a composition according to the inventive subject matter.
Figure 28:
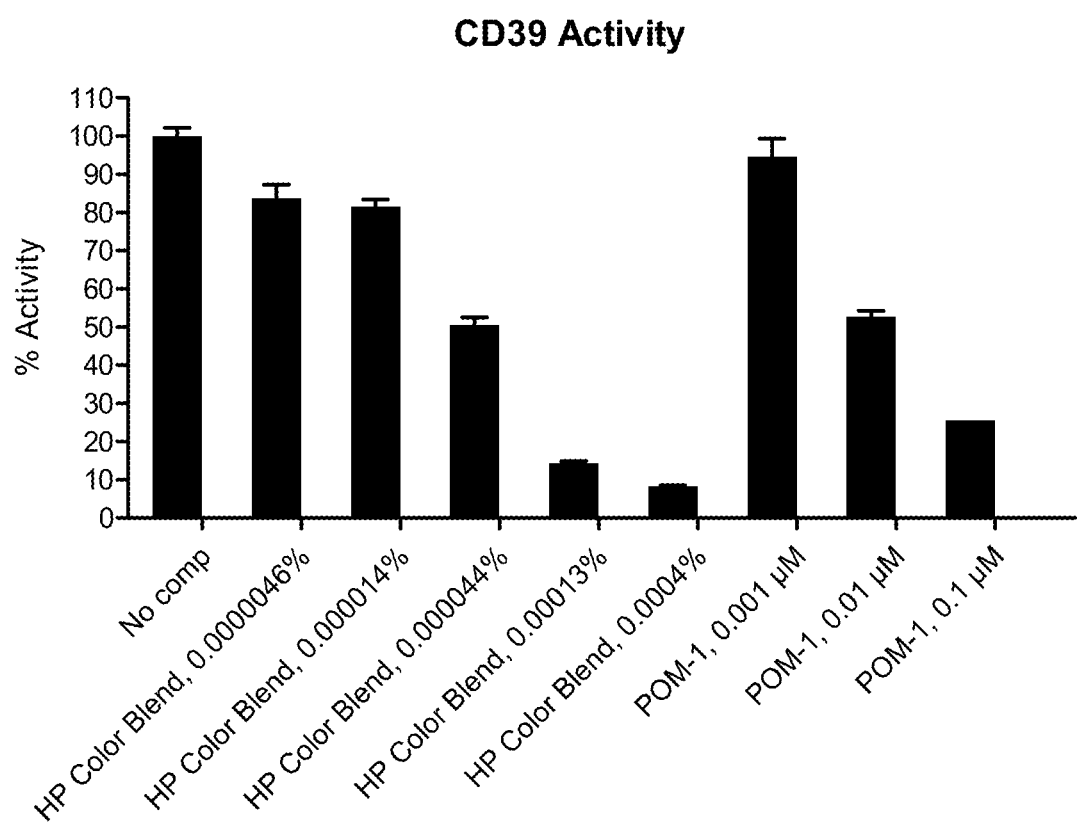
FIG. 28 is a graph depicting exemplary results for CD39 inhibition using a composition at low concentrations according to the inventive subject matter.
Figure 29:
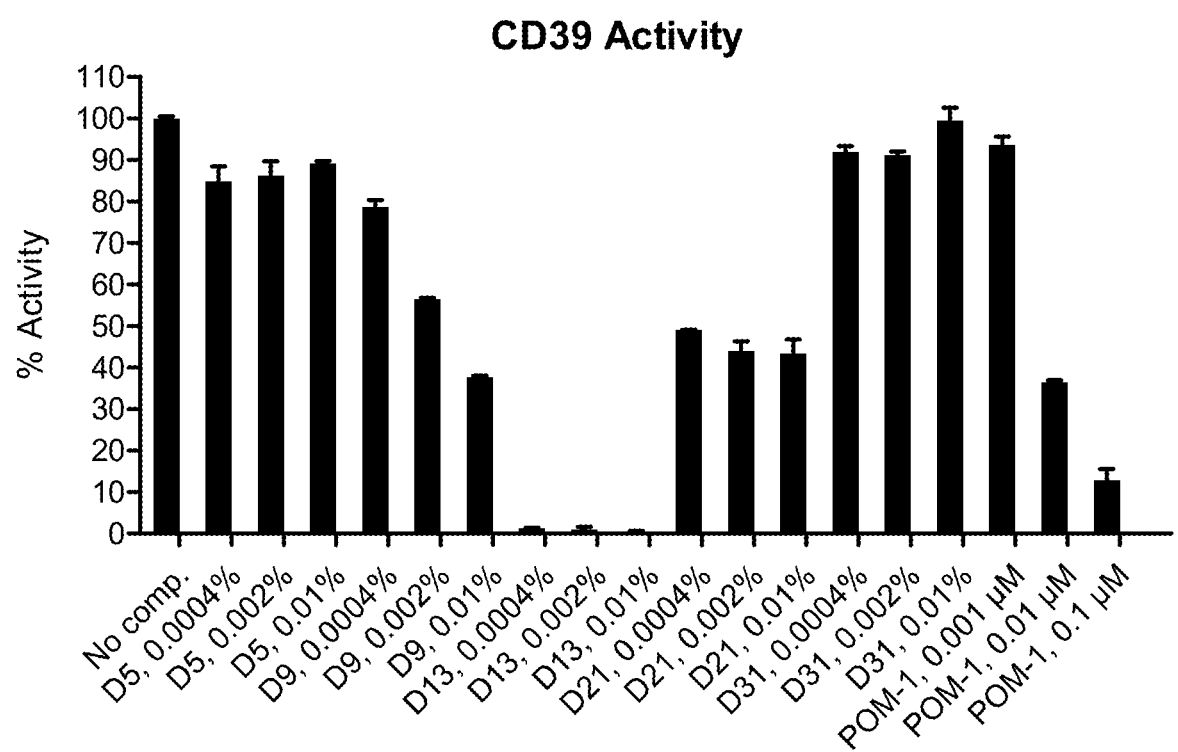
FIG. 29 is a graph depicting exemplary results for CD39 inhibition using further compositions according to the inventive subject matter.

Tables 70-72 and FIGS. 27-29 show corresponding results for the colored fractions. Here, Table 70 shows results for JAK1 inhibition using colored fractions of the representative composition. Table 71 shows results for JAK2 inhibition using colored fractions of the representative composition, and Table 72 shows results for JAK3 inhibition using colored fractions of the representative composition. Table 73 is a summary table of the results in Tables 70-72. Notably, a synergistic effect on inhibition against all three JAK kinases was observed at high concentrations where all colored fractions were used together in the representative composition as compared to individual colored fractions. Moreover, it should once more be noted that the compositions presented herein had similar inhibitory properties as compared to the reference compound.

TABLE 70

| Compounds | Kinase Activity Luminescence | | % Activity | |
|---|---|---|---|---|
| | Repeat1 | Repeat2 | Repeat1 | Repeat2 |
| No Compound | 19821 | 17710 | 95 | 105 |
| DC-5, 0.0004% | 20319 | 18662 | 92 | 101 |
| DC-5, 0.002% | 21569 | 20952 | 86 | 89 |
| DC-5, 0.01% | 27118 | 24076 | 59 | 74 |
| DC-9, 0.0004% | 22093 | 20295 | 84 | 93 |
| DC-9, 0.002% | 31746 | 29312 | 37 | 49 |
| DC-9, 0.01% | 37123 | 35475 | 10 | 18 |
| DC-13, 0.0004% | 27065 | 25415 | 59 | 68 |
| DC-13, 0.002% | 37759 | 34432 | 7 | 24 |
| DC-13, 0.01% | 36702 | 35308 | 12 | 19 |
| DC-21, 0.0004% | 16635 | 19342 | 110 | 97 |
| DC-21, 0.002% | 17067 | 20286 | 108 | 93 |
| DC-21, 0.01% | 23118 | 25700 | 79 | 66 |
| Staurosporine, 1 nM | 21164 | 24810 | 88 | 70 |
| Staurosporine, 10 nM | 28640 | 32000 | 52 | 35 |
| Staurosporine, 100 nM | 36908 | 39509 | 11 | 0 |
| Background | 39443 | 39051 | | |

TABLE 71

| Compounds | Kinase Activity Luminescence | | % Activity | |
|---|---|---|---|---|
| | Repeat1 | Repeat2 | Repeat1 | Repeat2 |
| No Compound | 5301 | 6612 | 102 | 98 |
| DC-5, 0.0004% | 6760 | 6751 | 98 | 98 |
| DC-5, 0.002% | 7887 | 9950 | 94 | 88 |
| DC-5, 0.01% | 9442 | 8832 | 89 | 91 |
| DC-9, 0.0004% | 17918 | 16309 | 63 | 68 |
| DC-9, 0.002% | 33289 | 32043 | 16 | 20 |
| DC-9, 0.01% | 34796 | 35989 | 12 | 8 |
| DC-13, 0.0004% | 30946 | 29748 | 24 | 27 |
| DC-13, 0.002% | 35743 | 34642 | 9 | 12 |
| DC-13, 0.01% | 36184 | 36167 | 7 | 8 |
| DC-21, 0.0004% | 6344 | 8335 | 99 | 93 |
| DC-21, 0.002% | 7862 | 9809 | 94 | 88 |
| DC-21, 0.01% | 13577 | 16488 | 77 | 68 |
| Staurosporine, 1 nM | 9482 | 10430 | 89 | 86 |
| Staurosporine, 10 nM | 17529 | 16180 | 65 | 69 |
| Staurosporine, 100 nM | 34660 | 34762 | 12 | 12 |
| Background | 39026 | 38243 | | |

TABLE 72

| Compounds | Kinase Activity Luminescence | | % Activity | |
|---|---|---|---|---|
| | Repeat1 | Repeat2 | Repeat1 | Repeat2 |
| No Compound | 16444 | 18933 | 106 | 94 |
| DC-5, 0.0004% | 18578 | 17845 | 96 | 99 |
| DC-5, 0.002% | 19889 | 20404 | 89 | 87 |
| DC-5, 0.01% | 22322 | 22047 | 78 | 79 |
| DC-9, 0.0004% | 30974 | 32880 | 37 | 27 |
| DC-9, 0.002% | 34085 | 35077 | 22 | 17 |
| DC-9, 0.01% | 34611 | 35273 | 19 | 16 |
| DC-13, 0.0004% | 34002 | 34554 | 22 | 19 |
| DC-13, 0.002% | 35870 | 36421 | 13 | 11 |
| DC-13, 0.01% | 36418 | 36584 | 11 | 10 |
| DC-21, 0.0004% | 16774 | 19477 | 104 | 91 |
| DC-21, 0.002% | 18739 | 21558 | 95 | 82 |
| DC-21, 0.01% | 23945 | 29444 | 70 | 44 |
| Staurosporine, 1 nM | 21050 | 24827 | 84 | 66 |
| Staurosporine, 10 nM | 32876 | 34538 | 27 | 20 |
| Staurosporine, 100 nM | 37496 | 39233 | 5 | 0 |
| Background | 39074 | 38166 | | |

TABLE 73

| Compounds | % Inhibition | | |
|---|---|---|---|
| | JAK1 | JAK2 | JAK3 |
| DC-5, 0.0004% | 4 | 2 | 2 |
| DC-5, 0.002% | 12 | 9 | 12 |
| DC-5, 0.01% | 33 | 10 | 21 |
| DC-9, 0.0004% | 12 | 34 | 68 |
| DC-9, 0.002% | 57 | 82 | 81 |
| DC-9, 0.01% | 86 | 90 | 82 |
| DC-13, 0.0004% | 36 | 75 | 79 |
| DC-13, 0.002% | 85 | 89 | 88 |
| DC-13, 0.01% | 84 | 92 | 90 |
| DC-21, 0.0004% | 0 | 4 | 2 |
| DC-21, 0.002% | 0 | 9 | 12 |
| DC-21, 0.01% | 28 | 28 | 43 |
| Staurosporine, 1 nM | 21 | 12 | 25 |
| Staurosporine, 10 nM | 56 | 33 | 77 |
| Staurosporine, 100 nM | 94 | 88 | 97 |

CD39:

In further experiments, the inventor sought to determine whether the representative compositions had an effect on the enzymatic activity of recombinant human CD39 using an in vitro enzymatic assay.

Reagents used are shown in Tables 74-77 below and tested as stated unless indicated otherwise (*POM-1 was used as reference compound). Table 74 shows the representative composition at standard concentrations, and Table 75 shows the representative composition at low concentrations. Table 76 shows colored fractions of the representative composition at standard concentrations. Here, D5 is the Yellow Blend, D9 is the Purple Blend, D21 is the Green Blend, D13 is the Red Blend, and D31 is CBD. As before, the red blend included Apple Extract, Pomegranate Extract, Tomato Powder, Beet; the green blend included Olive Extract, Rosemary Extract, Green Coffee Bean Extract, Kale; the orange/yellow blend included Onion Extract, Ginger Extract, Grapefruit Extract, Carrot; and the purple/blue blend included Grape, Blueberry Extract, Currant, Elderberry. Table 77 lists CD39.

100 µl of Colorimetric Detection Reagent was added to the reaction mix. After a 15 minutes incubation, absorbance was measured using a Tecan plate reader at 630 nm.

Data Analysis: Enzyme activity assays were performed in duplicates at each concentration. The Absorbance intensity data were analyzed and compared. In the absence of the compound, the intensity in each data set was defined as 100% (Ce) activity. In the absence of enzyme, the intensity in each data set was defined as 0% (C0) activity. The percent activity in the presence of each compound was calculated according to the following equation: % activity=(C−C0)/(Ce−C0), where C=the intensity in the presence of the compound (all percent activities below zero were shown zero in the table).

Remarkably high and significant inhibitory activity was found for CD39 across all tested concentrations as is shown in Tables 77-78 below, with Table 78 and FIG. 27 depicting the results for standard concentrations and Table 79 and FIG. 28 showing results for low concentrations. As can be readily seen from the results, inhibition relative to the reference inhibitor was unexpectedly strong relative to known reference inhibitor POM-1. Notably, the IC50 concentration for the composition was at 0.000044%. When tested for inhibitory activity for the colored fractions, the inhibitory activity partitioned partially, but not completely, to selected fractions as can be seen from the results in Table 80 and FIG. 29.

TABLE 74

| Compound | Form Supplied | Stock Conc. | Dissolving Solvent | Test Range |
| --- | --- | --- | --- | --- |
| HP Color Blend lot#33890000X11020 | Powder | 1% (w/v) | 70% EtOH | 0.0004, 0.002 and 0.01% |
| POM-1* | Powder | 1 mM | Water | 0.001, 0.01 and 0.1 µM |

TABLE 75

| Sample | Form Supplied | Stock Conc. | Dissolving Solvent | Test Range |
| --- | --- | --- | --- | --- |
| HP Color Blend lot#33890000X11020 | Powder | 1% (w/v) | 70% EtOH | 0.00000046, 0.000014, 0.00004, 0.00013, and 0.0004% |
| POM-1* | Powder | 1 mM | Water | 0.001, 0.01 and 0.1 µM |

TABLE 76

| Sample | Form Supplied | Stock Conc. | Dissolving Solvent | Test Range |
| --- | --- | --- | --- | --- |
| D5 | Powder | 1% (w/v) | 70% EtOH | 0.0004, 0.002 and 0.01% |
| D9 | Powder | 1% (w/v) | 70% EtOH | 0.0004, 0.002 and 0.01% |
| D13 | Powder | 1% (w/v) | 70% EtOH | 0.0004, 0.002 and 0.01% |
| D21 | Powder | 1% (w/v) | 70% EtOH | 0.0004, 0.002 and 0.01% |
| D31 | Powder | 1% (w/v) | 70% EtOH | 0.0004, 0.002 and 0.01% |
| POM-1* | Powder | 1 mM | Water | 0.001, 0.01 and 0.1 µM |
| AMPCP* | Powder | 100 mM | Water | 1, 10 and 100 µM |

TABLE 77

| Assay | Catalog # | Enzyme Lot # | Enzyme Used (ng)/Reaction | Substrate |
| --- | --- | --- | --- | --- |
| CD39 | 71284 | 180406 | 10 | 70 µM ATP |

Assay Conditions: In general, all assays points were done by following the CD39 and CD73 Inhibitor Screening Assay Kit protocol (BPS Bioscience, #79278 and 72055, respectively). The CD39 enzymatic reactions were conducted in duplicate at room temperature for 30 minutes in a 50 µl mixture containing assay buffer, ATP, CD39 enzymes, and the test compound. Test compounds were preincubated with the enzyme for 30 minutes. Reactions were started by addition of the substrate. The 50 µl reactions were carried out in a 96-well transparent plate. After enzymatic reactions,

TABLE 78

| Condition | Net absorbance | | Activity (%) | | CD39 Inhibition (%) |
| --- | --- | --- | --- | --- | --- |
| | Rep. 1 | Rep.2 | Rep. 1 | Rep.2 | |
| No compound | 0.51 | 0.55 | 95 | 105 | |
| HP Color Blend, 0.0004% | 0.01 | 0.01 | 1 | 1 | 99 |
| HP Color Blend, 0.002% | 0.01 | 0.01 | 2 | 2 | 98 |
| HP Color Blend, 0.01% | 0.02 | 0.01 | 3 | 2 | 98 |
| POM-1, 0.001 µM | 0.42 | 0.41 | 79 | 78 | 21 |
| POM-1, 0.01 µM | 0.26 | 0.30 | 49 | 56 | 47 |
| POM-1, 0.1 µM | 0.08 | 0.10 | 14 | 19 | 84 |
| Blank | 0.00 | 0.00 | | | |

TABLE 79

| Condition | Net absorbance | | Activity (%) | | Inhibition (%) |
| --- | --- | --- | --- | --- | --- |
| | Rep. 1 | Rep.2 | Rep. 1 | Rep.2 | |
| No compound | 0.289 | 0.277 | 102 | 98 | |
| HP Color Blend, 0.0000046% | 0.247 | 0.227 | 87 | 80 | 16 |
| HP Color Blend, 0.000014% | 0.236 | 0.226 | 83 | 80 | 18 |
| HP Color Blend, 0.000044% | 0.138 | 0.149 | 48 | 53 | 49 |
| HP Color Blend, 0.00013% | 0.040 | 0.043 | 14 | 15 | 85 |
| HP Color Blend, 0.0004% | 0.025 | 0.024 | 8 | 8 | 92 |
| POM-1, 0.001 µM | 0.281 | 0.254 | 99 | 90 | 5 |
| POM-1, 0.01 µM | 0.154 | 0.145 | 54 | 51 | 47 |
| POM-1, 0.1 µM | 0.073 | 0.073 | 26 | 26 | 74 |
| Blank | 0.001 | 0.001 | | | |

TABLE 80

| Condition | Net absorbance Rep. 1 | Net absorbance Rep.2 | Activity (%) Rep. 1 | Activity (%) Rep.2 | Inhibition (%) |
|---|---|---|---|---|---|
| No compound | 0.54 | 0.53 | 100 | 100 | |
| D5, 0.0004% | 0.48 | 0.44 | 88 | 81 | 15 |
| D5, 0.002% | 0.48 | 0.44 | 90 | 83 | 14 |
| D5, 0.01% | 0.48 | 0.48 | 90 | 89 | 11 |
| D9, 0.0004% | 0.43 | 0.41 | 80 | 77 | 21 |
| D9, 0.002% | 0.30 | 0.31 | 56 | 57 | 44 |
| D9, 0.01% | 0.20 | 0.21 | 37 | 38 | 62 |
| D13, 0.0004% | 0.01 | 0.01 | 1 | 1 | 99 |
| D13, 0.002% | 0.00 | 0.01 | 0 | 2 | 99 |
| D13, 0.01% | 0.01 | 0.00 | 1 | 0 | 99 |
| D21, 0.0004% | 0.26 | 0.26 | 49 | 49 | 51 |
| D21, 0.002% | 0.23 | 0.25 | 42 | 46 | 56 |
| D21, 0.01% | 0.25 | 0.22 | 47 | 40 | 57 |
| D31, 0.0004% | 0.50 | 0.49 | 93 | 91 | 8 |
| D31, 0.002% | 0.48 | 0.49 | 90 | 92 | 9 |
| D31, 0.01% | 0.52 | 0.55 | 96 | 103 | 1 |
| POM-1, 0.001 µM | 0.51 | 0.49 | 96 | 92 | 6 |
| POM-1, 0.01 µM | 0.19 | 0.20 | 36 | 37 | 64 |
| POM-1, 0.1 µM | 0.08 | 0.06 | 16 | 10 | 87 |
| Blank | 0.00 | 0.00 | | | |

Figure 30:
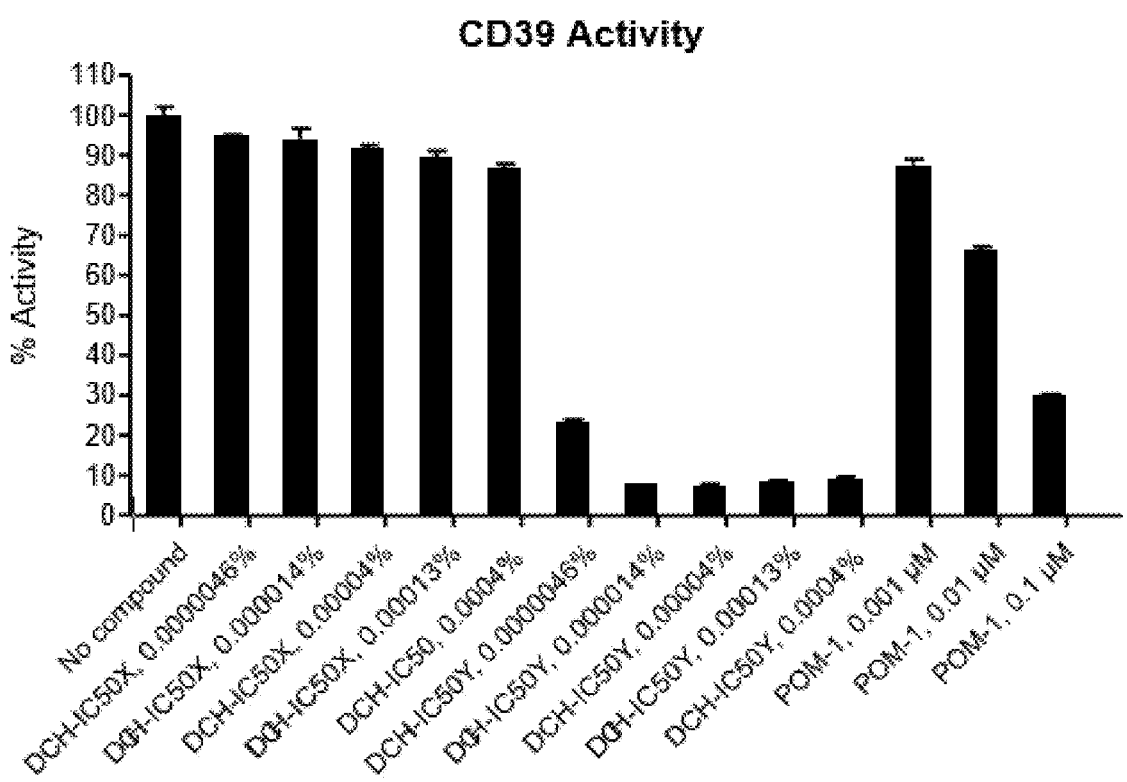
FIG. 30 is a graph depicting exemplary results for CD39 inhibition using selected compositions according to the inventive subject matter.

The inventor then further investigated whether one or more specific plant materials and their polyphenols were associated with the inhibitory activity against CD39. To that end, the inventor tested two components of the red colored blend: Apple Extract (DCH-IC50X) and Pomegranate extract (DCH-IC50Y) at the low concentration ranges as shown in Table 81 with otherwise identical assay conditions. Results are shown in Table 82 and FIG. 30.

TABLE 81

| Sample | Form Supplied | Stock Conc. | Dissolving Solvent | Test Range |
|---|---|---|---|---|
| DCH-IC50X (Apple Extract of RED Blend) | Powder | 1% (w/v) | 70% EtOH | 0.0000046, 0.000014, 0.00004, 0.00013, and 0.0004% |
| DCH-IC50Y (Pomegranate Extract of RED Blend) | Powder | 1% (w/v) | 70% EtOH | |
| POM-1* | Powder | 1 mM | Water | 0.001, 0.01 and 0.1 µM |

TABLE 82

| Condition | Net absorbance Rep. 1 | Net absorbance Rep.2 | Activity (%) Rep. 1 | Activity (%) Rep.2 | Inhibition (%) |
|---|---|---|---|---|---|
| No compound | 0.30 | 0.29 | 102 | 98 | 0 |
| DCH-IC50X, 0.0000046% | 0.28 | 0.28 | 95 | 95 | 5 |
| DCH-IC50X, 0.000014% | 0.28 | 0.27 | 97 | 92 | 6 |
| DCH-IC50X, 0.00004% | 0.27 | 0.27 | 92 | 91 | 8 |
| DCH-IC50X, 0.00013% | 0.27 | 0.26 | 91 | 88 | 11 |
| DCH-IC50X, 0.0004% | 0.25 | 0.26 | 85 | 88 | 13 |
| DCH-IC50Y, 0.0000046% | 0.07 | 0.07 | 22 | 24 | 77 |
| DCH-IC50Y, 0.000014% | 0.03 | 0.03 | 8 | 8 | 92 |
| DCH-IC50Y, 0.00004% | 0.03 | 0.03 | 7 | 8 | 92 |
| DCH-IC50Y, 0.00013% | 0.03 | 0.03 | 8 | 9 | 91 |
| DCH-IC50Y, 0.0004% | 0.03 | 0.03 | 9 | 10 | 91 |
| POM-1, 0.001 µM | 0.25 | 0.26 | 86 | 89 | 13 |
| POM-1, 0.01 µM | 0.20 | 0.19 | 67 | 66 | 33 |
| POM-1, 0.1 µM | 0.09 | 0.09 | 30 | 29 | 70 |
| Blank | 0.01 | 0.00 | | | |

In still further experiments, the inventor also investigated whether CD39 could also be inhibited by a multivitamin mix. To that end, a comparative experiment was conducted between a multivitamin mix (denoted as DCH-TIV-1.0 (Adult Centrum Multivitamin)) and the representative composition (denoted as DCH-TIC-0.5) using the same experimental procedure for CD39 as described above. The compositions are shown in Table 83.

TABLE 83

| Sample | Form Supplied | Stock Conc. | Dissolving Solvent | Test Range |
|---|---|---|---|---|
| DCH-TIC-0.5 | Powder | 1% (w/v) | 70% EtOH | 0.004, 0.02 and 0.1% |
| DCH-TIV-1.0 (Adult Centrum Multivitamin) | Powder | 1% (w/v) | 70% EtOH | 0.004, 0.02 and 0.1% |
| POM-1* | Solution | 1 mM | Water | 0.001, 0.01 and 0.1 µM |

Figure 31:
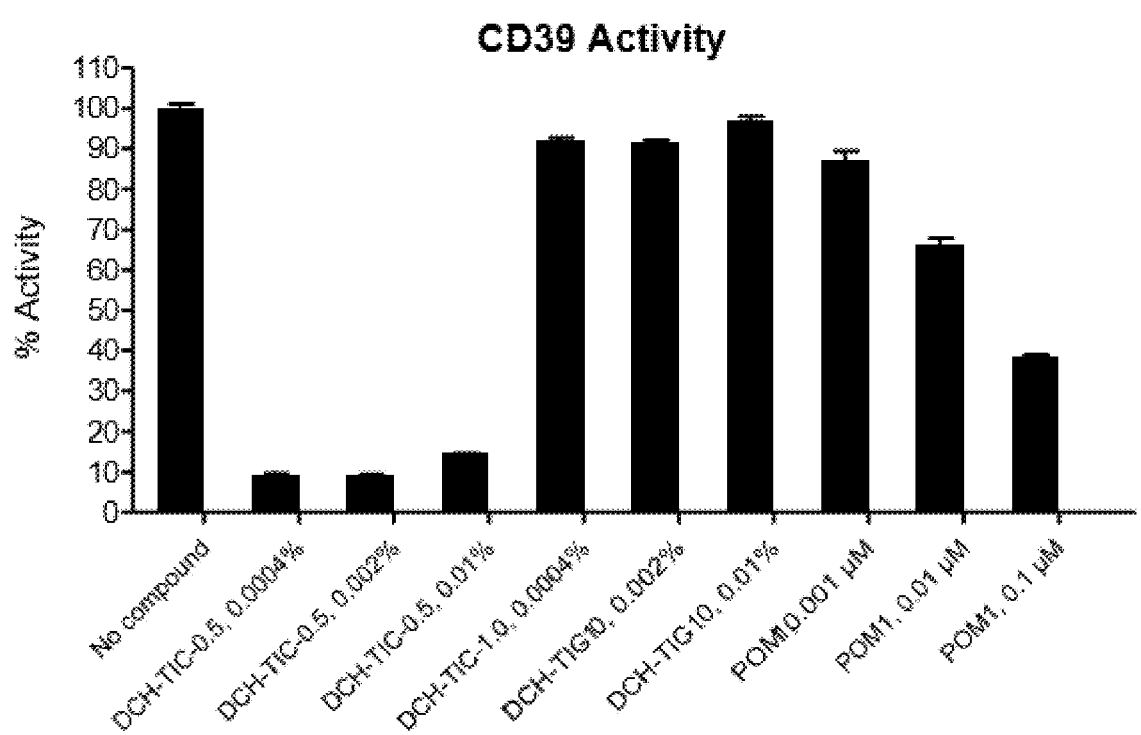
FIG. 31 is a graph depicting exemplary results for CD39 inhibition using a composition according to the inventive subject matter and a known multivitamin composition.

The results for this comparison are shown in Table 84 and FIG. 31. As can be clearly seen form the results, the representative composition had very strong inhibitory effect on CD39 whereas the multivitamin composition had substantially no significant inhibitory effect.

TABLE 84

| Condition | Net Signal (Absorbance) Repeat 1 | Net Signal (Absorbance) Repeat 2 | Activity (%) Repeat 1 | Activity (%) Repeat 2 | Inhibition (%) |
|---|---|---|---|---|---|
| No compound | 0.32 | 0.32 | 99 | 101 | 0 |
| DCH-TIC-0.5, 0.0004% | 0.04 | 0.04 | 9 | 10 | 90 |
| DCH-TIC-0.5, 0.002% | 0.04 | 0.04 | 10 | 9 | 91 |
| DCH-TIC-0.5, 0.01% | 0.05 | 0.05 | 15 | 15 | 85 |
| DCH-TIV-1.0, 0.0004% | 0.30 | 0.30 | 93 | 92 | 8 |
| DCH-TIV-1.0, 0.002% | 0.30 | 0.29 | 92 | 91 | 8 |
| DCH-TIV-1.0, 0.01% | 0.31 | 0.31 | 96 | 98 | 3 |
| POM-1, 0.001 µM | 0.27 | 0.29 | 85 | 89 | 13 |
| POM-1, 0.01 µM | 0.21 | 0.22 | 65 | 68 | 34 |
| POM-1, 0.1 µM | 0.13 | 0.13 | 39 | 38 | 61 |
| Blank | 0.01 | 0.01 | | | |

CD73:

In still further experiments, the inventor further sought to determine whether the representative compositions had an effect on the enzymatic activity of recombinant human CD73 using an in vitro enzymatic assay.

Reagents used are shown in Tables 85-89 below and tested as stated unless indicated otherwise (*AMPCP or Quercetin were used as reference compound). Table 85 shows the representative composition at standard concentrations, and Table 86 shows colored fractions of the representative composition at standard concentrations. Here, D5 is the Yellow Blend, D9 is the Purple Blend, D21 is the Green Blend, D13 is the Red Blend, and D31 is CBD. As before, the red blend included Apple Extract, Pomegranate Extract, Tomato Powder, Beet; the green blend included Olive Extract, Rosemary Extract, Green Coffee Bean Extract, Kale; the orange/yellow blend included Onion Extract, Ginger Extract, Grapefruit Extract, Carrot; and the purple/blue blend included Grape, Blueberry Extract, Currant, Elderberry. Table 87 lists CD73.

TABLE 85

| Compound | Form Supplied | Stock Conc. | Dissolving Solvent | Test Range |
|---|---|---|---|---|
| HP Color Blend lot#33890000X11020 | Powder | 1% (w/v) | 70% EtOH | 0.0004, 0.002 and 0.01% |
| Quercetin* | Powder | 100 mM | Water | 1, 10 and 100 µM |

TABLE 86

| Sample | Form Supplied | Stock Conc. Solvent | Dissolving | Test Range |
|---|---|---|---|---|
| D5 | Powder | 1% (w/v) | 70% EtOH | 0.0004, 0.002 and 0.01% |
| D9 | Powder | 1% (w/v) | 70% EtOH | 0.0004, 0.002 and 0.01% |
| D13 | Powder | 1% (w/v) | 70% EtOH | 0.0004, 0.002 and 0.01% |
| D21 | Powder | 1% (w/v) | 70% EtOH | 0.0004, 0.002 and 0.01% |
| D31 | Powder | 1% (w/v) | 70% EtOH | 0.0004, 0.002 and 0.01% |
| AMPCP* | Powder | 100 mM | Water | 1, 10 and 100 µM |

TABLE 87

| Assay | Catalog # | Enzyme Lot # | Enzyme Used (ng)/Reaction | Substrate |
|---|---|---|---|---|
| CD73 | 71184 | 190123 | 3 | 100 µM ADP |

Assay Conditions: In general, all assays points were done by following the CD39 and CD73 Inhibitor Screening Assay Kit protocol (BPS Bioscience, #79278 and 72055, respectively). The CD73 enzymatic reactions were conducted in duplicate at room temperature for 30 minutes in a 50 µl mixture containing assay buffer, ADP, CD73 enzymes, and the test compound. Test compounds were preincubated with the enzyme for 30 minutes. Reactions were started by addition of the substrate. The 50 µl reactions were carried out in a 96-well transparent plate. After enzymatic reactions, 100 µl of Colorimetric Detection Reagent was added to the reaction mix. After a 15 minutes incubation, absorbance was measured using a Tecan plate reader at 630 nm.

Data Analysis: Enzyme activity assays were performed in duplicates at each concentration. The Absorbance intensity data were analyzed and compared. In the absence of the compound, the intensity in each data set was defined as 100% (Ce) activity. In the absence of enzyme, the intensity in each data set was defined as 0% (C0) activity. The percent activity in the presence of each compound was calculated according to the following equation: % activity=(C−C0)/(Ce−C0), where C=the intensity in the presence of the compound (all percent activities below zero were shown zero in the table).

Figure 32:
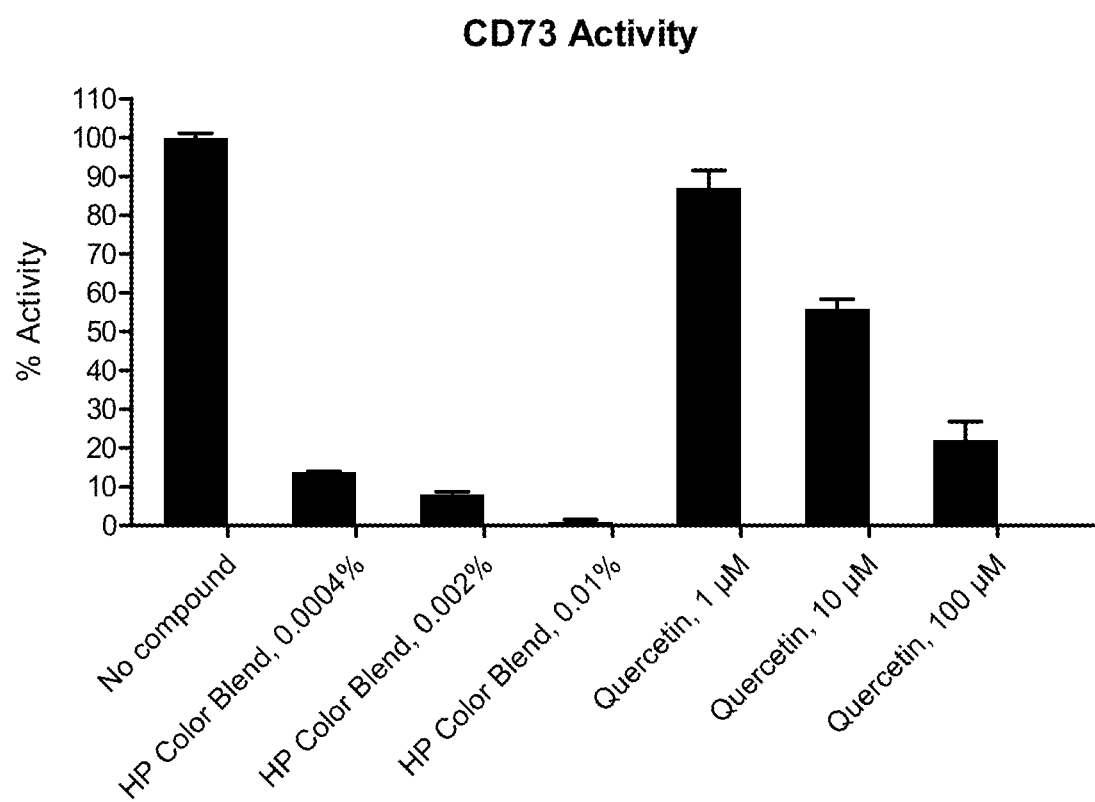
FIG. 32 is a graph depicting exemplary results for CD73 inhibition using a composition according to the inventive subject matter.
Figure 33:
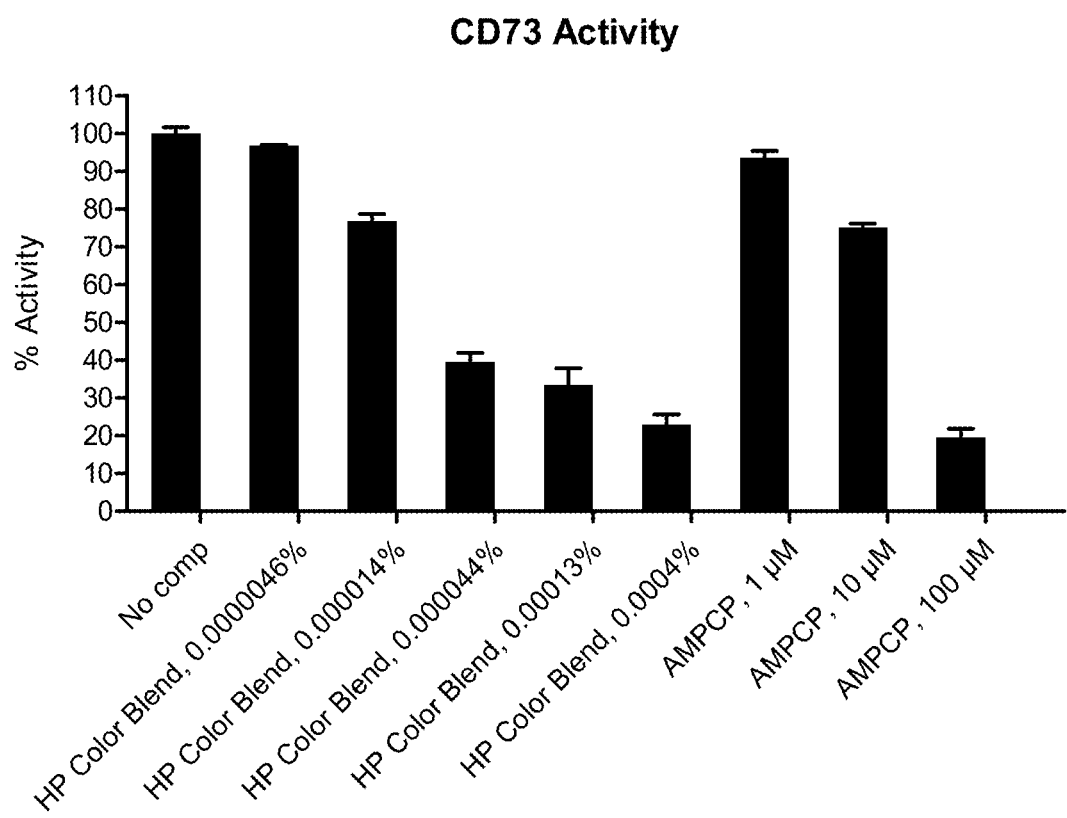
FIG. 33 is a graph depicting exemplary results for CD73 inhibition using a composition at low concentrations according to the inventive subject matter.
Figure 34:
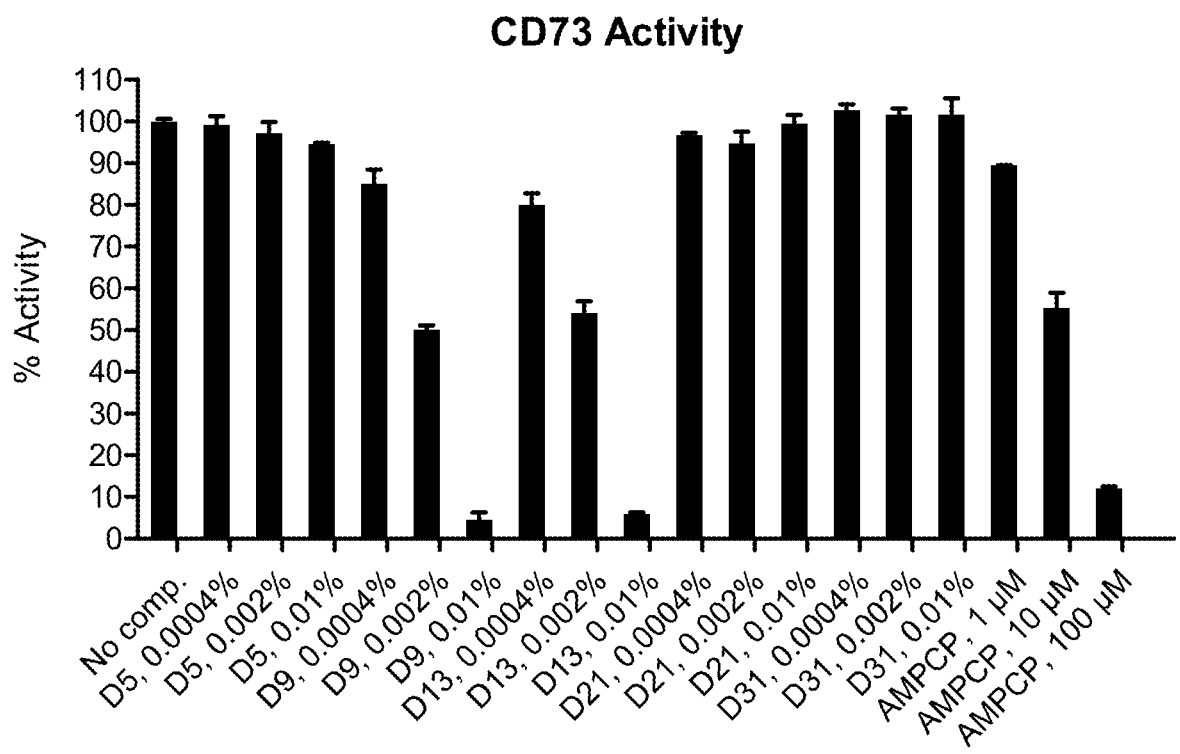
FIG. 34 is a graph depicting exemplary results for CD73 inhibition using further compositions according to the inventive subject matter.

As can be see form the results in Tables 88-90, the inhibition of CD73 by the representative composition and its fractions was remarkably high, especially in comparison to the current reference standard. Table 88 and FIG. 32 show the results for CD73 inhibition at standard concentrations and Table 89 and FIG. 33 show the results for CD73 inhibition at low concentrations. Here, the IC50 of the representative composition is at about 0.000044%. Moreover, as can be taken from these results and the results for the colored fractions as shown in Table 90 and FIG. 34, a strong synergy of the colored fractions when used in combination (as in the representative composition) was observed with respect to CD73 inhibition.

TABLE 88

| Condition | Net absorbance Rep. 1 | Net absorbance Rep.2 | Activity (%) Rep. 1 | Activity (%) Rep.2 | CD73 Inhibition (%) |
|---|---|---|---|---|---|
| No compound | 0.44 | 0.43 | 101 | 99 | |
| HP Color Blend, 0.0004% | 0.06 | 0.06 | 14 | 14 | 86 |
| HP Color Blend, 0.002% | 0.03 | 0.04 | 7 | 9 | 92 |
| HP Color Blend, 0.01% | 0.01 | 0.00 | 2 | 1 | 99 |
| Quercetin, 1 µM | 0.40 | 0.36 | 92 | 82 | 13 |
| Quercetin, 10 µM | 0.23 | 0.25 | 53 | 58 | 44 |
| Quercetin, 100 µM | 0.12 | 0.08 | 27 | 17 | 78 |
| Blank | 0.00 | 0.00 | | | |

TABLE 89

| Condition | Net absorbance Rep. 1 | Net absorbance Rep.2 | Activity (%) Rep. 1 | Activity (%) Rep.2 | Inhibition (%) |
|---|---|---|---|---|---|
| No compound | 0.408 | 0.395 | 102 | 98 | |
| HP Color Blend, 0.0000046% | 0.389 | 0.388 | 97 | 97 | 3 |
| HP Color Blend, 0.000014% | 0.301 | 0.316 | 75 | 79 | 23 |
| HP Color Blend, 0.000044% | 0.169 | 0.150 | 42 | 37 | 60 |
| HP Color Blend, 0.00013% | 0.117 | 0.153 | 29 | 38 | 67 |
| HP Color Blend, 0.0004% | 0.104 | 0.083 | 26 | 20 | 77 |
| AMPCP, 1 µM | 0.368 | 0.383 | 92 | 96 | 6 |
| AMPCP, 10 µM | 0.298 | 0.306 | 74 | 76 | 25 |
| AMPCP, 100 µM | 0.071 | 0.089 | 17 | 22 | 80 |
| Blank | 0.001 | 0.002 | | | |

TABLE 90

| Condition | Net absorbance Rep. 1 | Net absorbance Rep.2 | Activity (%) Rep. 1 | Activity (%) Rep.2 | Inhibition (%) |
|---|---|---|---|---|---|
| No compound | 0.33 | 0.34 | 99 | 101 | |
| D5, 0.0004% | 0.34 | 0.33 | 101 | 97 | 1 |
| D5, 0.002% | 0.33 | 0.32 | 100 | 94 | 3 |
| D5, 0.01% | 0.32 | 0.32 | 95 | 94 | 5 |
| D9, 0.0004% | 0.30 | 0.27 | 88 | 82 | 15 |
| D9, 0.002% | 0.17 | 0.17 | 49 | 51 | 50 |
| D9, 0.01% | 0.01 | 0.02 | 3 | 6 | 95 |
| D13, 0.0004% | 0.28 | 0.26 | 83 | 77 | 20 |
| D13, 0.002% | 0.17 | 0.19 | 51 | 57 | 46 |
| D13, 0.01% | 0.02 | 0.02 | 6 | 5 | 94 |
| D21, 0.0004% | 0.33 | 0.32 | 97 | 96 | 3 |
| D21, 0.002% | 0.33 | 0.31 | 98 | 92 | 5 |
| D21, 0.01% | 0.33 | 0.34 | 97 | 102 | 1 |
| D31, 0.0004% | 0.35 | 0.34 | 104 | 101 | 0 |
| D31, 0.002% | 0.35 | 0.34 | 103 | 100 | 0 |
| D31, 0.01% | 0.35 | 0.33 | 106 | 98 | 0 |
| AMPCP, 1 µM | 0.30 | 0.30 | 89 | 89 | 11 |
| AMPCP, 10 µM | 0.18 | 0.20 | 52 | 59 | 45 |
| AMPCP, 100 µM | 0.04 | 0.04 | 13 | 12 | 88 |
| Blank | 0.01 | 0.00 | | | |

To further investigate whether CD73 could also be inhibited by a multivitamin formulation, the inventor performed comparative experiments between the representative composition and a multivitamin composition using the same test procedure as outlined above. Table 91 lists the reagents used in this experiment (DCH-TIV-0.5 denotes the representative composition, and DCH-TIV-1.0 denotes Adult Centrum Multivitamin).

TABLE 91

| Sample | Form Supplied | Stock Conc. | Dissolving Solvent | Test Range |
|---|---|---|---|---|
| DCH-TIV-0.5 | Powder | 1% (w/v) | 70% EtOH | 0.004, 0.02 and 0.1% |
| DCH-TIV-1.0 (AdultCentrum Multivitamin) | Powder | 1% (w/v) | 70% EtOH | 0.004, 0.02 and 0.1% |
| AMPCP* | Powder | 10 mM | Water | 0.1, 1 and 10 µM |

Figure 35:
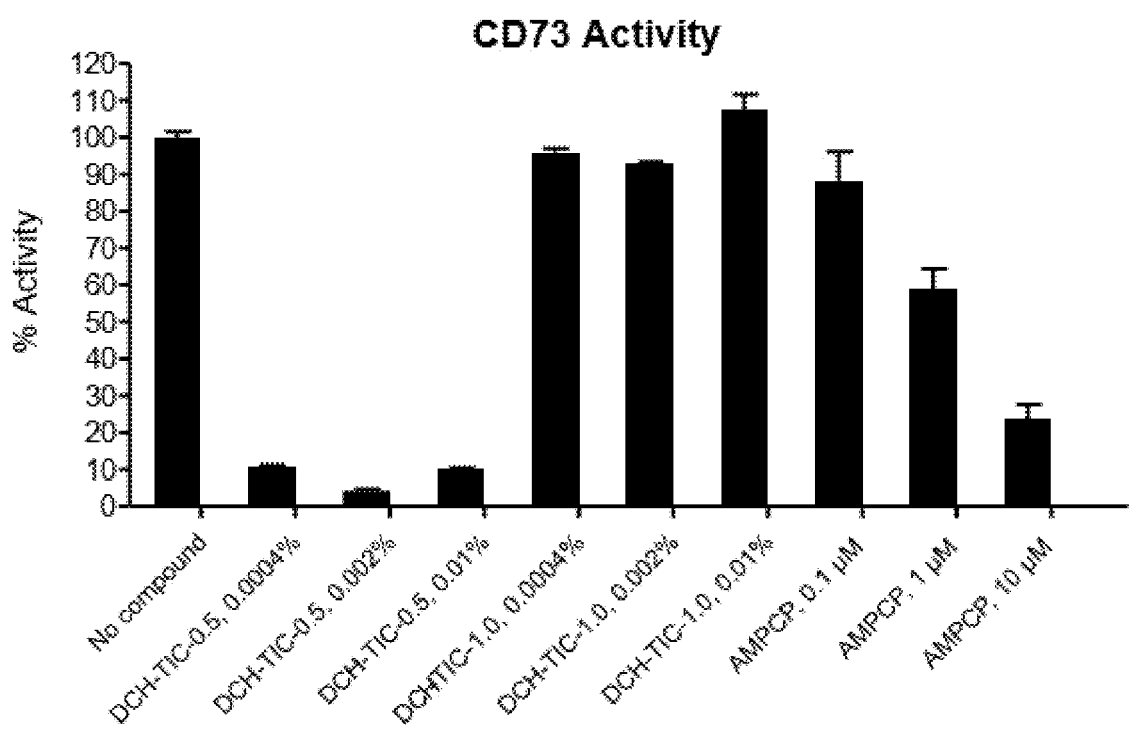
FIG. 35 is a graph depicting exemplary results for CD73 inhibition using a composition according to the inventive subject matter and a known multivitamin composition.

As can be readily seen form the results in Table 92 and FIG. 35 the representative composition had substantial inhibitory activity with regard to CD73, however, only minor inhibitory activity with the multivitamin composition was observed.

TABLE 92

| Condition | Net Signal (Absorbance) | | Activity (%) | | Inhibition (%) |
|---|---|---|---|---|---|
| | Repeat 1 | Repeat 2 | Repeat 1 | Repeat 2 | |
| No compound | 0.18 | 0.17 | 101 | 99 | 0 |
| DCH-TIV-0.5, 0.0004% | 0.02 | 0.02 | 10 | 11 | 89 |
| DCH-TIV-0.5, 0.002% | 0.01 | 0.01 | 4 | 5 | 96 |
| DCH-TIV-0.5, 0.01% | 0.02 | 0.02 | 10 | 10 | 90 |
| DCH-TIV-1.0, 0.0004% | 0.17 | 0.17 | 97 | 95 | 4 |
| DCH-TIV-1.0, 0.002% | 0.17 | 0.16 | 93 | 92 | 7 |
| DCH-TIV-1.0, 0.01% | 0.20 | 0.18 | 112 | 103 | 0 |
| AMPCP, 0.1 µM | 0.14 | 0.17 | 81 | 96 | 12 |
| AMPCP, 1 µM | 0.09 | 0.11 | 53 | 64 | 41 |
| AMPCP, 10 µM | 0.04 | 0.05 | 20 | 28 | 76 |
| Blank | 0.00 | 0.00 | | | |

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical or nutraceutical composition refers to both direct and indirect administration of the pharmaceutical or nutraceutical composition, wherein direct administration of the pharmaceutical or nutraceutical composition is typically performed by a health care professional (e.g., physician, nurse, dietitian, etc.), and wherein indirect administration includes a step of providing or making available the pharmaceutical or nutraceutical composition to the health care professional or individual in need thereof for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:
1. A nutritional composition, comprising:
a nutritionally acceptable carrier in combination with a plurality of chemically distinct polyphenol-containing plant materials having a red color, a green color, an orange-yellow color, and a purple-blue color;
    wherein the red colored plant materials comprise an apple extract, a pomegranate extract, a tomato powder, and a beet root powder;
    wherein the green colored plant materials comprise an olive extract, a rosemary extract, a green coffee bean extract, and a kale powder;
    wherein the orange-yellow colored plant materials comprise an onion extract, a ginger extract, a grapefruit extract, and a carrot powder;
    wherein the purple-blue colored plant materials comprise a grape extract, a blueberry extract, a currant powder, and an elderberry powder; and
wherein the combination of plant materials is a synergistic combination with respect to inhibition of at least one biochemical marker selected from the group consisting of BACE1, CD38, CD73, CDK5, JAK1, JAK2, and JAK3.

2. The composition of claim 1 wherein the combination of plant materials is a synergistic combination with respect to inhibition of BACE1, CD38, and CD73.

3. The composition of claim 1 wherein the composition further inhibits at least one additional biochemical marker selected from the group consisting of ARG-1, ARG-2, SIRT-1, CD39, IDO1, IDO2, NAMPT, PCSK9, CD47, and Cathepsin S.

4. The composition of claim 1 wherein the composition further inhibits Keap/Nrf2 binding and/or ACE2/Spike binding.

5. The composition of claim 1 wherein the composition is formulated in single dosage units for oral administration.

6. The composition of claim 5 wherein the dosage unit contains between 50 and 1,000 mg of the composition.

7. The composition of claim 5 wherein the dosage unit is formulated as a capsule, a gummy, or a powder.

8. The composition of claim 5 wherein the composition further comprises a vitamin, a dietary trace element or mineral, a nicotinamide riboside, a probiotic, and/or a prebiotic.

9. The composition of claim 1 wherein the composition is effective to treat and/or reduce a symptom of inflammatory condition, a cardiovascular condition, a neurological condition, a metabolic condition, and a cancer.

10. The composition of claim 1 wherein the apple extract, the pomegranate extract, the olive extract, the rosemary extract, the green coffee bean extract, the onion extract, the ginger extract, the grapefruit extract, the grape extract, and the blueberry extract are ethanol extracts or ethanol/water extracts.

11. A method of supporting health of an individual, comprising administering to the individual a composition according to claim 1.

12. The method of claim 11 wherein the composition is administered to thereby provide immune support, metabolic support, support longevity, support central nervous system (CNS) function, reduce an inflammatory response, reduce effects of cardiovascular disease, and reduce the rate of amyloid beta plaque formation.

13. The method of claim 11 wherein the composition is orally administered over at least 30 days and/or at a daily dose of between 50 and 1,000 mg.

14. The method of claim 11 further comprising co-administering a vitamin, a dietary trace element or mineral, a nicotinamide riboside, a probiotic, and/or a prebiotic, optionally wherein the dietary trace element or mineral, the nicotinamide riboside, the probiotic, and/or the prebiotic are co-administered in the same dosage unit.

* * * * *